US009326876B2

(12) United States Patent
Acosta et al.

(10) Patent No.: US 9,326,876 B2
(45) Date of Patent: *May 3, 2016

(54) APPARATUS AND METHODS FOR DELIVERY OF MULTIPLE DISTRIBUTED STENTS

(71) Applicant: J.W. MEDICAL SYSTEMS LTD., Weihai Shandong (CN)

(72) Inventors: Pablo Acosta, Newark, CA (US); Bernard Andreas, Redwood City, CA (US); Steve Landreville, Mountain View, CA (US); David W. Snow, San Carlos, CA (US)

(73) Assignee: J.W. Medical Systems Ltd., Weihai Shandong (CN)

( * ) Notice: Subject to any disclaimer, the term of this patent is extended or adjusted under 35 U.S.C. 154(b) by 19 days.

This patent is subject to a terminal disclaimer.

(21) Appl. No.: 14/258,129

(22) Filed: Apr. 22, 2014

(65) Prior Publication Data

US 2014/0228931 A1    Aug. 14, 2014

Related U.S. Application Data

(60) Division of application No. 13/037,140, filed on Feb. 28, 2011, now Pat. No. 8,702,781, which is a (Continued)

(51) Int. Cl.
*A61F 2/06* (2013.01)
*A61F 2/966* (2013.01)
(Continued)

(52) U.S. Cl.
CPC . *A61F 2/966* (2013.01); *A61F 2/82* (2013.01); *A61F 2/91* (2013.01); *A61F 2/915* (2013.01);
(Continued)

(58) Field of Classification Search
CPC ............ A61F 2/966; A61F 2/82; A61F 2/91; A61F 2/915; A61F 2/95; A61F 2/958; A61F 2/0095; A61F 2002/826; A61F 2002/828; A61F 2002/91508; A61F 2002/91516; A61F 2002/91525; A61F 2002/91533; A61F 2002/91541; A61F 2002/9155; A61F 2002/91558; A61F 2002/91591; A61F 2002/9505; A61F 2002/9583; A61F 2210/0033; A61F 2210/0042; A61F 2250/006; A61F 2250/0071; A61M 25/0068; A61M 25/0075; A61M 25/008; A61M 25/0082; A61M 25/10; A61M 25/104; A61M 2025/0681; H01Q 3/2676
USPC ........................................................ 606/1.11
See application file for complete search history.

(56) References Cited

U.S. PATENT DOCUMENTS 4,069,825 A    1/1978 Akiyama
4,468,224 A    8/1984 Enzmann et al.
(Continued)

FOREIGN PATENT DOCUMENTS

CN    1856280 A    1/2006
CN    104068951    10/2014
(Continued)

OTHER PUBLICATIONS

Extended European Search Report of EP Patent Application No. 08746459, dated Oct. 16, 2014, 6 pages.
(Continued)

*Primary Examiner* — Katrina Stransky
(74) *Attorney, Agent, or Firm* — Kilpatrick Townsend & Stockton LLP

(57) ABSTRACT

Delivery catheters and systems are adapted for delivering multiple discreet prostheses in body lumens. An exemplary delivery catheter comprises a sheath, a pusher for moving the prostheses relative to the sheath, and a valve member for selectively retaining the prostheses in the sheath. For balloon expandable stents, an elongated shaft and an expandable member are slidably disposed in the sheath, and the prostheses are positionable on the expandable member for deployment in the body lumen. The valve member allows a selected number of prostheses to be deployed from the sheath while retaining other prostheses within the sheath.

15 Claims, 35 Drawing Sheets

Related U.S. Application Data continuation of application No. 11/538,904, filed on Oct. 5, 2006, now Pat. No. 7,922,755, which is a division of application No. 10/412,714, filed on Apr. 10, 2003, now Pat. No. 7,137,993, which is a continuation-in-part of application No. 10/306,813, filed on Nov. 27, 2002, now abandoned.

(60) Provisional application No. 60/364,389, filed on Mar. 13, 2002, provisional application No. 60/336,967, filed on Dec. 3, 2001.

(51) Int. Cl.
| | |
|---|---|
| A61F 2/91 | (2013.01) |
| A61F 2/915 | (2013.01) |
| A61F 2/95 | (2013.01) |
| A61F 2/958 | (2013.01) |
| A61M 25/00 | (2006.01) |
| H01Q 3/26 | (2006.01) |
| A61F 2/00 | (2006.01) |
| A61F 2/82 | (2013.01) |
| A61M 25/10 | (2013.01) |
| A61M 25/06 | (2006.01) |

(52) U.S. Cl.
CPC . *A61F 2/95* (2013.01); *A61F 2/958* (2013.01); *A61M 25/0068* (2013.01); *A61M 25/0075* (2013.01); *H01Q 3/2676* (2013.01); *A61F 2/0095* (2013.01); *A61F 2002/826* (2013.01); *A61F 2002/828* (2013.01); *A61F 2002/9155* (2013.01); *A61F 2002/91508* (2013.01); *A61F 2002/91516* (2013.01); *A61F 2002/91525* (2013.01); *A61F 2002/91533* (2013.01); *A61F 2002/91541* (2013.01); *A61F 2002/91558* (2013.01); *A61F 2002/91591* (2013.01); *A61F 2002/9505* (2013.01); *A61F 2002/9583* (2013.01); *A61F 2210/0033* (2013.01); *A61F 2210/0042* (2013.01); *A61F 2250/006* (2013.01); *A61F 2250/0071* (2013.01); *A61M 25/008* (2013.01); *A61M 25/0082* (2013.01); *A61M 25/10* (2013.01); *A61M 25/104* (2013.01); *A61M 2025/0681* (2013.01)

(56) References Cited

U.S. PATENT DOCUMENTS

| | | | |
|---|---|---|---|
| 4,512,338 | A | 4/1985 | Balko |
| 4,564,014 | A | 1/1986 | Fogarty et al. |
| 4,580,568 | A | 4/1986 | Gianturco |
| 4,681,110 | A | 7/1987 | Wiktor |
| 4,690,684 | A | 9/1987 | McGreevy et al. |
| 4,733,665 | A | 3/1988 | Palmaz |
| 4,739,762 | A | 4/1988 | Palmaz |
| 4,748,982 | A | 6/1988 | Horzewski et al. |
| 4,762,129 | A | 8/1988 | Bonzel |
| 4,770,176 | A | 9/1988 | McGreevy et al. |
| 4,775,337 | A | 10/1988 | Van Wagener et al. |
| 4,776,337 | A | 10/1988 | Palmaz |
| 4,886,062 | A | 12/1989 | Wiktor |
| 4,891,225 | A | 1/1990 | Langer et al. |
| 4,950,227 | A | 8/1990 | Savin et al. |
| 4,988,356 | A | 1/1991 | Crittenden et al. |
| 4,994,066 | A | 2/1991 | Voss |
| 4,994,069 | A | 2/1991 | Ritchart et al. |
| 4,994,298 | A | 2/1991 | Yasuda |
| 5,013,318 | A | 5/1991 | Spranza, III |
| 5,026,377 | A * | 6/1991 | Burton et al. ............... 606/108 |
| 5,035,706 | A | 7/1991 | Giantureo et al. |
| 5,040,548 | A | 8/1991 | Yock |
| 5,061,273 | A | 10/1991 | Yock |
| 5,064,435 | A | 11/1991 | Porter |
| 5,092,877 | A | 3/1992 | Pinchuk |
| 5,102,417 | A | 4/1992 | Palmaz |
| 5,104,404 | A | 4/1992 | Wolff |
| 5,122,154 | A | 6/1992 | Rhodes |
| 5,135,535 | A | 8/1992 | Kramer |
| 5,158,548 | A | 10/1992 | Lau et al. |
| 5,171,222 | A | 12/1992 | Euteneuer et al. |
| 5,192,297 | A | 3/1993 | Hull |
| 5,195,984 | A | 3/1993 | Schatz |
| 5,201,757 | A | 4/1993 | Heyn et al. |
| 5,217,495 | A | 6/1993 | Kaplan et al. |
| 5,219,355 | A | 6/1993 | Parodi et al. |
| 5,226,913 | A | 7/1993 | Pinchuk |
| 5,246,421 | A | 9/1993 | Saab |
| 5,261,887 | A | 11/1993 | Walker |
| 5,273,536 | A | 12/1993 | Savas |
| 5,282,823 | A | 2/1994 | Schwartz et al. |
| 5,282,824 | A | 2/1994 | Gianturco |
| 5,300,085 | A | 4/1994 | Yock |
| 5,312,415 | A | 5/1994 | Palermo |
| 5,328,469 | A | 7/1994 | Coletti |
| 5,334,187 | A | 8/1994 | Fischell et al. |
| 5,391,172 | A | 2/1995 | Williams et al. |
| 5,421,955 | A | 6/1995 | Lau et al. |
| 5,443,498 | A | 8/1995 | Fontaine |
| 5,445,646 | A | 8/1995 | Euteneuer et al. |
| 5,456,713 | A | 10/1995 | Chuter |
| 5,458,615 | A | 10/1995 | Klemm et al. |
| 5,470,315 | A | 11/1995 | Adams |
| 5,478,349 | A | 12/1995 | Nicholas |
| 5,484,444 | A | 1/1996 | Braunschweiler et al. |
| 5,490,837 | A | 2/1996 | Blaeser et al. |
| 5,496,346 | A | 3/1996 | Horzewski et al. |
| 5,501,227 | A | 3/1996 | Yock |
| 5,507,768 | A | 4/1996 | Lau et al. |
| 5,507,771 | A | 4/1996 | Gianturco |
| 5,514,093 | A | 5/1996 | Ellis et al. |
| 5,514,154 | A | 5/1996 | Lau et al. |
| 5,522,882 | A | 6/1996 | Gaterud et al. |
| 5,527,354 | A | 6/1996 | Fontaine et al. |
| 5,531,735 | A | 7/1996 | Thompson |
| 5,533,968 | A | 7/1996 | Muni et al. |
| 5,534,007 | A | 7/1996 | St. Germain et al. |
| 5,545,209 | A | 8/1996 | Roberts et al. |
| 5,549,551 | A | 8/1996 | Peacock, III et al. |
| 5,549,563 | A | 8/1996 | Kronner |
| 5,549,635 | A | 8/1996 | Solar |
| 5,554,181 | A | 9/1996 | Das |
| 5,562,725 | A | 10/1996 | Schmitt et al. |
| 5,571,086 | A | 11/1996 | Kaplan et al. |
| 5,591,195 | A | 1/1997 | Taheri et al. |
| 5,593,412 | A | 1/1997 | Martinez et al. |
| 5,607,444 | A | 3/1997 | Lam |
| 5,607,463 | A | 3/1997 | Schwartz et al. |
| 5,628,755 | A | 5/1997 | Heller et al. |
| 5,628,775 | A | 5/1997 | Jackson et al. |
| 5,634,928 | A | 6/1997 | Fischell et al. |
| 5,639,274 | A | 6/1997 | Fischell et al. |
| 5,662,675 | A | 9/1997 | Polanskyj Stockert et al. |
| 5,662,703 | A | 9/1997 | Yurek et al. |
| 5,670,161 | A | 9/1997 | Healy et al. |
| 5,676,654 | A | 10/1997 | Ellis et al. |
| 5,683,451 | A | 11/1997 | Lenker et al. |
| 5,690,644 | A | 11/1997 | Yurek et al. |
| 5,693,085 | A | 12/1997 | Buirge et al. |
| 5,697,948 | A | 12/1997 | Marin et al. |
| 5,697,971 | A | 12/1997 | Fischell et al. |
| 5,702,418 | A | 12/1997 | Ravenscroft |
| 5,702,419 | A | 12/1997 | Berry et al. |
| 5,709,701 | A | 1/1998 | Parodi |
| 5,716,393 | A | 2/1998 | Lindenberg et al. |
| 5,722,669 | A | 3/1998 | Shimizu et al. |
| 5,723,003 | A | 3/1998 | Winston et al. |
| 5,735,869 | A | 4/1998 | Fernandez-Aceytuno |
| 5,741,323 | A | 4/1998 | Pathak et al. |
| 5,749,848 | A | 5/1998 | Jang et al. |
| 5,749,890 | A | 5/1998 | Shaknovich |
| 5,749,921 | A | 5/1998 | Lenker et al. |

(56) References Cited

U.S. PATENT DOCUMENTS

| | | |
|---|---|---|
| 5,755,697 A | 5/1998 | Jones et al. |
| 5,755,772 A | 5/1998 | Evans et al. |
| 5,755,776 A | 5/1998 | Al-Saadon |
| 5,755,781 A | 5/1998 | Jayaraman |
| 5,769,882 A | 6/1998 | Fogarty et al. |
| 5,772,669 A | 6/1998 | Vrba |
| 5,776,141 A | 7/1998 | Klein et al. |
| 5,792,144 A | 8/1998 | Fischell et al. |
| 5,797,951 A | 8/1998 | Mueller et al. |
| 5,800,519 A | 9/1998 | Sandock |
| 5,807,398 A | 9/1998 | Shaknovich |
| 5,824,040 A | 10/1998 | Cox et al. |
| 5,824,041 A | 10/1998 | Lenker et al. |
| 5,833,694 A | 11/1998 | Poncet |
| 5,836,964 A | 11/1998 | Richter et al. |
| 5,843,090 A | 12/1998 | Schuetz |
| 5,843,092 A | 12/1998 | Heller et al. |
| 5,855,563 A | 1/1999 | Kaplan et al. |
| 5,858,556 A | 1/1999 | Eckert et al. |
| 5,870,381 A | 2/1999 | Kawasaki et al. |
| 5,879,370 A | 3/1999 | Fischell et al. |
| 5,891,190 A | 4/1999 | Boneau |
| 5,895,398 A | 4/1999 | Wensel et al. |
| 5,899,935 A | 5/1999 | Ding |
| 5,902,332 A | 5/1999 | Schatz |
| 5,919,175 A | 7/1999 | Sirhan |
| 5,921,971 A | 7/1999 | Agro et al. |
| 5,922,020 A | 7/1999 | Klein et al. |
| 5,941,869 A | 8/1999 | Patterson et al. |
| 5,951,585 A | 9/1999 | Cathcart et al. |
| 5,961,536 A | 10/1999 | Mickley et al. |
| 5,965,879 A | 10/1999 | Leviton |
| 5,968,069 A | 10/1999 | Dusbabek et al. |
| 5,972,027 A | 10/1999 | Johnson |
| 5,976,107 A | 11/1999 | Mertens et al. |
| 5,976,155 A | 11/1999 | Foreman et al. |
| 5,980,484 A | 11/1999 | Ressemann et al. |
| 5,980,486 A | 11/1999 | Enger |
| 5,980,514 A | 11/1999 | Kupiecki et al. |
| 5,980,552 A | 11/1999 | Pinchasik et al. |
| 5,984,957 A | 11/1999 | Laptewicz, Jr. et al. |
| 5,989,280 A | 11/1999 | Euteneuer et al. |
| 5,993,484 A | 11/1999 | Shmulewitz |
| 5,997,563 A | 12/1999 | Kretzers et al. |
| 6,004,328 A | 12/1999 | Solar |
| 6,007,517 A | 12/1999 | Anderson |
| 6,010,530 A | 1/2000 | Goicoechea |
| 6,022,359 A | 2/2000 | Frantzen |
| 6,022,374 A | 2/2000 | Imran |
| 6,027,519 A | 2/2000 | Stanford |
| 6,033,434 A | 3/2000 | Borghi |
| 6,036,725 A | 3/2000 | Avellanet |
| 6,039,721 A | 3/2000 | Johnson et al. |
| 6,042,589 A | 3/2000 | Marianne |
| 6,050,999 A | 4/2000 | Paraschac et al. |
| 6,056,722 A | 5/2000 | Jayaraman |
| 6,063,111 A | 5/2000 | Hieshima et al. |
| 6,066,155 A | 5/2000 | Amann et al. |
| 6,068,655 A | 5/2000 | Seguin et al. |
| 6,070,589 A | 6/2000 | Keith et al. |
| 6,090,063 A | 7/2000 | Makower et al. |
| 6,090,136 A | 7/2000 | McDonald et al. |
| 6,102,942 A | 8/2000 | Ahari |
| 6,106,530 A | 8/2000 | Harada |
| RE36,857 E | 9/2000 | Euteneuer et al. |
| 6,120,477 A | 9/2000 | Campbell et al. |
| 6,120,522 A | 9/2000 | Vrba et al. |
| 6,123,712 A | 9/2000 | Di Caprio et al. |
| 6,123,723 A | 9/2000 | Konya et al. |
| 6,126,685 A | 10/2000 | Lenker et al. |
| 6,129,756 A | 10/2000 | Kugler |
| 6,132,460 A | 10/2000 | Thompson |
| 6,139,572 A | 10/2000 | Campbell et al. |
| 6,143,016 A | 11/2000 | Bleam et al. |
| 6,165,167 A | 12/2000 | Delaloye |
| 6,165,210 A | 12/2000 | Lau et al. |
| 6,171,334 B1 | 1/2001 | Cox |
| 6,179,878 B1 | 1/2001 | Duering |
| 6,183,509 B1 | 2/2001 | Dibie |
| 6,187,034 B1 | 2/2001 | Frantzen |
| 6,190,402 B1 | 2/2001 | Horton et al. |
| 6,196,995 B1 | 3/2001 | Fagan |
| 6,200,337 B1 | 3/2001 | Moriuchi et al. |
| 6,217,585 B1 | 4/2001 | Houser et al. |
| 6,238,991 B1 | 5/2001 | Suzuki |
| 6,241,691 B1 | 6/2001 | Ferrera et al. |
| 6,241,758 B1 | 6/2001 | Cox |
| 6,248,122 B1 | 6/2001 | Klumb et al. |
| 6,251,132 B1 | 6/2001 | Ravenscroft et al. |
| 6,251,134 B1 | 6/2001 | Alt et al. |
| 6,254,612 B1 | 7/2001 | Hieshima |
| 6,254,628 B1 | 7/2001 | Wallace et al. |
| 6,258,117 B1 | 7/2001 | Camrud et al. |
| 6,264,688 B1 | 7/2001 | Herklotz et al. |
| 6,267,783 B1 | 7/2001 | Letendre et al. |
| 6,270,524 B1 | 8/2001 | Kim |
| 6,273,895 B1 | 8/2001 | Pinchuk et al. |
| 6,273,911 B1 | 8/2001 | Cox et al. |
| 6,273,913 B1 | 8/2001 | Wright et al. |
| 6,287,291 B1 | 9/2001 | Bigus et al. |
| 6,312,458 B1 | 11/2001 | Golds |
| 6,315,794 B1 | 11/2001 | Richter |
| 6,319,277 B1 | 11/2001 | Rudnick et al. |
| 6,322,586 B1 | 11/2001 | Monroe et al. |
| 6,325,823 B1 | 12/2001 | Horzewski et al. |
| 6,334,871 B1 | 1/2002 | Dor et al. |
| 6,340,366 B2 | 1/2002 | Wijay |
| 6,344,272 B1 | 2/2002 | Oldenburg et al. |
| 6,348,065 B1 | 2/2002 | Brown et al. |
| 6,350,252 B2 | 2/2002 | Ray et al. |
| 6,350,277 B1 | 2/2002 | Kocur |
| 6,357,104 B1 | 3/2002 | Myers |
| 6,361,558 B1 | 3/2002 | Hieshima et al. |
| 6,375,676 B1 | 4/2002 | Cox |
| 6,379,365 B1 | 4/2002 | Diaz |
| 6,383,171 B1 | 5/2002 | Gifford et al. |
| 6,394,995 B1 | 5/2002 | Solar et al. |
| 6,409,753 B1 | 6/2002 | Brown et al. |
| 6,415,696 B1 | 7/2002 | Erickeson et al. |
| 6,416,543 B1 | 7/2002 | Hilaire et al. |
| 6,419,693 B1 | 7/2002 | Fariabi |
| 6,425,898 B1 | 7/2002 | Wilson et al. |
| 6,428,811 B1 | 8/2002 | West et al. |
| 6,451,025 B1 | 9/2002 | Jervis |
| 6,451,050 B1 | 9/2002 | Rudakov et al. |
| 6,464,720 B2 | 10/2002 | Boatman et al. |
| 6,468,298 B1 | 10/2002 | Pelton |
| 6,468,299 B2 | 10/2002 | Stack et al. |
| 6,485,510 B1 | 11/2002 | Camrud et al. |
| 6,488,694 B1 | 12/2002 | Lau et al. |
| 6,488,702 B1 | 12/2002 | Besselink |
| 6,511,468 B1 | 1/2003 | Cragg et al. |
| 6,520,986 B2 | 2/2003 | Martin et al. |
| 6,520,987 B1 | 2/2003 | Plante |
| 6,527,789 B1 | 3/2003 | Lau et al. |
| 6,527,799 B2 | 3/2003 | Shanley |
| 6,530,944 B2 | 3/2003 | West et al. |
| 6,540,777 B2 | 4/2003 | Stenzel |
| 6,551,350 B1 | 4/2003 | Thornton et al. |
| 6,555,157 B1 | 4/2003 | Hossainy |
| 6,558,415 B2 | 5/2003 | Thompson |
| 6,562,067 B2 | 5/2003 | Mathis |
| 6,565,599 B1 | 5/2003 | Hong et al. |
| 6,569,180 B1 | 5/2003 | Sirhan et al. |
| 6,575,993 B1 | 6/2003 | Yock |
| 6,579,305 B1 | 6/2003 | Lashinski |
| 6,579,309 B1 | 6/2003 | Loos et al. |
| 6,582,394 B1 | 6/2003 | Reiss et al. |
| 6,582,460 B1 | 6/2003 | Cryer |
| 6,585,756 B1 | 7/2003 | Strecker |
| 6,589,273 B1 | 7/2003 | McDermott |
| 6,592,549 B2 | 7/2003 | Gerdts et al. |
| 6,599,296 B1 | 7/2003 | Gillick et al. |
| 6,599,314 B2 | 7/2003 | Mathis |

(56) References Cited

U.S. PATENT DOCUMENTS

| | | |
|---|---|---|
| 6,602,226 B1 | 8/2003 | Smith et al. |
| 6,602,282 B1 | 8/2003 | Yan |
| 6,605,062 B1 | 8/2003 | Hurley et al. |
| 6,605,109 B2 | 8/2003 | Fiedler |
| 6,607,553 B1 | 8/2003 | Healy et al. |
| 6,613,074 B1 | 9/2003 | Mitelberg et al. |
| 6,629,992 B2 | 10/2003 | Bigus et al. |
| 6,645,517 B2 | 11/2003 | West |
| 6,645,547 B1 | 11/2003 | Shekalim et al. |
| 6,656,212 B2 | 12/2003 | Ravenscroft et al. |
| 6,660,031 B2 | 12/2003 | Tran et al. |
| 6,660,381 B2 | 12/2003 | Halas et al. |
| 6,663,660 B2 | 12/2003 | Dusbabek et al. |
| 6,666,883 B1 | 12/2003 | Seguin et al. |
| 6,676,693 B1 | 1/2004 | Belding et al. |
| 6,676,695 B2 | 1/2004 | Solem |
| 6,679,909 B2 | 1/2004 | McIntosh et al. |
| 6,685,730 B2 | 2/2004 | West et al. |
| 6,692,465 B2 | 2/2004 | Kramer |
| 6,699,280 B2 | 3/2004 | Camrud et al. |
| 6,699,281 B2 | 3/2004 | Vallana et al. |
| 6,699,724 B1 | 3/2004 | West et al. |
| 6,702,843 B1 | 3/2004 | Brown |
| 6,709,379 B1 | 3/2004 | Brandau et al. |
| 6,709,440 B2 | 3/2004 | Callol et al. |
| 6,712,827 B2 | 3/2004 | Ellis et al. |
| 6,712,845 B2 | 3/2004 | Hossainy |
| 6,723,071 B2 | 4/2004 | Gerdts et al. |
| 6,736,842 B2 | 5/2004 | Healy et al. |
| 6,743,219 B1 | 6/2004 | Dwyer et al. |
| 6,743,251 B1 | 6/2004 | Eder |
| 6,761,734 B2 | 7/2004 | Suhr |
| 6,776,771 B2 | 8/2004 | van Moorlegem et al. |
| 6,778,316 B2 | 8/2004 | Halas et al. |
| 6,790,227 B2 | 9/2004 | Burgermeister |
| 6,800,065 B2 | 10/2004 | Duane et al. |
| 6,825,203 B2 | 11/2004 | Pasternak et al. |
| 6,837,901 B2 | 1/2005 | Rabkin et al. |
| 6,849,084 B2 | 2/2005 | Rabkin et al. |
| 6,852,252 B2 | 2/2005 | Halas et al. |
| 6,855,125 B2 | 2/2005 | Shanley |
| 6,858,034 B1 | 2/2005 | Hijlkema et al. |
| 6,878,161 B2 | 4/2005 | Lenker |
| 6,884,257 B1 | 4/2005 | Cox |
| 6,893,417 B2 | 5/2005 | Gribbons et al. |
| 6,896,695 B2 | 5/2005 | Mueller et al. |
| 6,899,728 B1 | 5/2005 | Phillips et al. |
| 6,908,624 B2 | 6/2005 | Hossainy et al. |
| 6,913,619 B2 | 7/2005 | Brown et al. |
| 6,918,928 B2 | 7/2005 | Wolinsky et al. |
| 6,939,376 B2 | 9/2005 | Shulz et al. |
| 6,945,989 B1 | 9/2005 | Betelia et al. |
| 6,945,995 B2 | 9/2005 | Nicholas |
| 6,951,053 B2 | 10/2005 | Padilla et al. |
| 6,962,603 B1 | 11/2005 | Brown et al. |
| 6,964,676 B1 | 11/2005 | Gerberding et al. |
| 6,991,646 B2 | 1/2006 | Clerc et al. |
| 6,994,721 B2 | 2/2006 | Israel |
| 7,004,964 B2 | 2/2006 | Thompson et al. |
| 7,005,454 B2 | 2/2006 | Brocchini et al. |
| 7,022,132 B2 | 4/2006 | Kocur |
| 7,029,493 B2 | 4/2006 | Majercak et al. |
| 7,037,327 B2 | 5/2006 | Salmon et al. |
| 7,090,694 B1 | 8/2006 | Morris et al. |
| 7,101,840 B2 | 9/2006 | Brocchini et al. |
| 7,131,993 B2 | 11/2006 | Gregorich |
| 7,137,993 B2 | 11/2006 | Acosta et al. |
| 7,141,063 B2 | 11/2006 | White et al. |
| 7,147,655 B2 | 12/2006 | Chermoni |
| 7,147,656 B2 | 12/2006 | Andreas et al. |
| 7,169,172 B2 | 1/2007 | Levine et al. |
| 7,169,174 B2 | 1/2007 | Fischell et al. |
| 7,172,620 B2 | 2/2007 | Gilson |
| 7,175,654 B2 | 2/2007 | Bonsignore et al. |
| 7,182,779 B2 | 2/2007 | Acosta et al. |
| 7,192,440 B2 | 3/2007 | Andreas et al. |
| 7,208,001 B2 | 4/2007 | Coyle et al. |
| 7,208,002 B2 | 4/2007 | Shelso |
| 7,220,275 B2 | 5/2007 | Davidson et al. |
| 7,220,755 B2 | 5/2007 | Betts et al. |
| 7,223,283 B2 | 5/2007 | Chouinard |
| 7,238,197 B2 | 7/2007 | Sequin et al. |
| 7,241,308 B2 | 7/2007 | Andreas et al. |
| 7,244,336 B2 | 7/2007 | Fischer et al. |
| 7,270,668 B2 | 9/2007 | Andreas et al. |
| 7,294,146 B2 | 11/2007 | Chew et al. |
| 7,300,456 B2 | 11/2007 | Andreas et al. |
| 7,309,350 B2 | 12/2007 | Landreville et al. |
| 7,314,480 B2 | 1/2008 | Eidenschink et al. |
| 7,320,702 B2 | 1/2008 | Hammersmark et al. |
| 7,323,006 B2 | 1/2008 | Andreas et al. |
| 7,326,236 B2 | 2/2008 | Andreas et al. |
| 7,351,255 B2 | 4/2008 | Andreas |
| 7,402,168 B2 | 7/2008 | Sanderson et al. |
| 7,534,449 B2 | 5/2009 | Saltzman et al. |
| 7,699,886 B2 | 4/2010 | Sugimoto |
| 7,824,439 B2 | 11/2010 | Toyokawa |
| 7,892,273 B2 | 2/2011 | George et al. |
| 7,892,274 B2 | 2/2011 | Will et al. |
| 7,905,913 B2 | 3/2011 | Chew et al. |
| 7,918,881 B2 | 4/2011 | Andreas et al. |
| 7,922,755 B2 | 4/2011 | Acosta et al. |
| 7,938,851 B2 | 5/2011 | Olson et al. |
| 7,938,852 B2 | 5/2011 | Andreas et al. |
| 7,993,388 B2 | 8/2011 | Lee et al. |
| 8,016,870 B2 | 9/2011 | Chew et al. |
| 8,070,789 B2 | 12/2011 | Will et al. |
| 8,070,794 B2 | 12/2011 | Issenmann |
| 8,157,851 B2 | 4/2012 | Andreas |
| 8,257,427 B2 | 9/2012 | Andersen et al. |
| 8,282,680 B2 | 10/2012 | Kao et al. |
| 8,317,850 B2 | 11/2012 | Kusleika |
| 8,317,859 B2 | 11/2012 | Snow et al. |
| 8,460,358 B2 | 6/2013 | Andreas et al. |
| 8,486,132 B2 | 7/2013 | Snow et al. |
| 8,585,747 B2 | 11/2013 | Andreas et al. |
| 8,702,781 B2 * | 4/2014 | Acosta et al. ............ 623/1.11 |
| 8,740,968 B2 | 6/2014 | Kao et al. |
| 2001/0001824 A1 | 5/2001 | Wu |
| 2001/0020154 A1 | 9/2001 | Bigus et al. |
| 2001/0020173 A1 | 9/2001 | Klumb et al. |
| 2001/0020181 A1 | 9/2001 | Layne |
| 2001/0035902 A1 | 11/2001 | Iddan et al. |
| 2001/0044595 A1 | 11/2001 | Reydel et al. |
| 2001/0044632 A1 | 11/2001 | Daniel et al. |
| 2001/0049547 A1 | 12/2001 | Moore |
| 2001/0049549 A1 | 12/2001 | Boylan et al. |
| 2001/0051822 A1 | 12/2001 | Stack et al. |
| 2002/0007212 A1 | 1/2002 | Brown et al. |
| 2002/0032457 A1 | 3/2002 | Sirhan et al. |
| 2002/0035395 A1 | 3/2002 | Sugimoto |
| 2002/0037358 A1 | 3/2002 | Barry et al. |
| 2002/0045914 A1 | 4/2002 | Roberts et al. |
| 2002/0052642 A1 | 5/2002 | Cox et al. |
| 2002/0087186 A1 | 7/2002 | Shelso |
| 2002/0091439 A1 | 7/2002 | Baker et al. |
| 2002/0092536 A1 | 7/2002 | LaFontaine et al. |
| 2002/0107560 A1 | 8/2002 | Richter |
| 2002/0111671 A1 | 8/2002 | Stenzel |
| 2002/0123786 A1 | 9/2002 | Gittings et al. |
| 2002/0123792 A1 | 9/2002 | Burgermeister |
| 2002/0128706 A1 | 9/2002 | Ospyka |
| 2002/0138132 A1 | 9/2002 | Brown |
| 2002/0151924 A1 | 10/2002 | Shiber |
| 2002/0151955 A1 | 10/2002 | Tran et al. |
| 2002/0156496 A1 | 10/2002 | Chermoni |
| 2002/0165599 A1 | 11/2002 | Nasralla |
| 2002/0168317 A1 | 11/2002 | Daighighian et al. |
| 2002/0177890 A1 | 11/2002 | Lenker |
| 2002/0183763 A1 | 12/2002 | Callol et al. |
| 2002/0188343 A1 | 12/2002 | Mathis |
| 2002/0188347 A1 | 12/2002 | Mathis |
| 2002/0193873 A1 | 12/2002 | Brucker et al. |
| 2003/0013266 A1 | 1/2003 | Fukuda et al. |

(56) References Cited

U.S. PATENT DOCUMENTS

| | | |
|---|---|---|
| 2003/0045923 A1 | 3/2003 | Bashiri et al. |
| 2003/0093143 A1 | 5/2003 | Zhao et al. |
| 2003/0097169 A1 | 5/2003 | Brucker et al. |
| 2003/0105511 A1 | 6/2003 | Welsh et al. |
| 2003/0114912 A1 | 6/2003 | Sequin et al. |
| 2003/0114919 A1 | 6/2003 | McQuiston et al. |
| 2003/0114922 A1 | 6/2003 | Iwasaka et al. |
| 2003/0125791 A1 | 7/2003 | Sequin et al. |
| 2003/0125800 A1 | 7/2003 | Shulze et al. |
| 2003/0125802 A1 | 7/2003 | Callol et al. |
| 2003/0135259 A1 | 7/2003 | Simso |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0139798 A1 | 7/2003 | Brown et al. |
| 2003/0163085 A1 | 8/2003 | Tanner et al. |
| 2003/0163155 A1 | 8/2003 | Haverkost et al. |
| 2003/0176909 A1 | 9/2003 | Kusleika |
| 2003/0191516 A1 | 10/2003 | Weldon et al. |
| 2003/0195609 A1 | 10/2003 | Berenstein |
| 2003/0199821 A1 | 10/2003 | Gerdts et al. |
| 2003/0204238 A1 | 10/2003 | Tedeschi |
| 2003/0208223 A1 | 11/2003 | Kleiner |
| 2003/0212447 A1 | 11/2003 | Euteneuer |
| 2003/0225446 A1 | 12/2003 | Hartley |
| 2004/0015224 A1 | 1/2004 | Armstrong et al. |
| 2004/0024450 A1 | 2/2004 | Shulze et al. |
| 2004/0030380 A1 | 2/2004 | Shulze et al. |
| 2004/0044395 A1 | 3/2004 | Nelson |
| 2004/0047909 A1 | 3/2004 | Ragheb et al. |
| 2004/0073290 A1 | 4/2004 | Chouinard |
| 2004/0087965 A1 | 5/2004 | Levine et al. |
| 2004/0088044 A1 | 5/2004 | Brown et al. |
| 2004/0093061 A1 | 5/2004 | Acosta et al. |
| 2004/0093067 A1 | 5/2004 | Israel |
| 2004/0093077 A1 | 5/2004 | White et al. |
| 2004/0098081 A1 | 5/2004 | Landreville et al. |
| 2004/0106979 A1 | 6/2004 | Goicoechea |
| 2004/0111145 A1 | 6/2004 | Serino et al. |
| 2004/0117008 A1 | 6/2004 | Wnendt et al. |
| 2004/0138737 A1 | 7/2004 | Davidson et al. |
| 2004/0143322 A1 | 7/2004 | Litvack et al. |
| 2004/0176832 A1 | 9/2004 | Hartley et al. |
| 2004/0181239 A1 | 9/2004 | Dorn et al. |
| 2004/0186551 A1 | 9/2004 | Kao et al. |
| 2004/0193245 A1 | 9/2004 | Deem et al. |
| 2004/0215165 A1 | 10/2004 | Coyle et al. |
| 2004/0215312 A1 | 10/2004 | Andreas et al. |
| 2004/0215331 A1 | 10/2004 | Chew et al. |
| 2004/0230285 A1 | 11/2004 | Gifford, III et al. |
| 2004/0243217 A1 | 12/2004 | Andersen et al. |
| 2004/0249434 A1 | 12/2004 | Andreas et al. |
| 2004/0249435 A1 | 12/2004 | Andreas et al. |
| 2004/0249439 A1 | 12/2004 | Richter et al. |
| 2005/0004657 A1 | 1/2005 | Burgermeister |
| 2005/0010276 A1 | 1/2005 | Acosta et al. |
| 2005/0038494 A1 | 2/2005 | Eidenschink |
| 2005/0038505 A1 | 2/2005 | Shulze et al. |
| 2005/0049673 A1 | 3/2005 | Andreas et al. |
| 2005/0055077 A1 | 3/2005 | Marco et al. |
| 2005/0075716 A1 | 4/2005 | Yan |
| 2005/0080474 A1 | 4/2005 | Andreas et al. |
| 2005/0080475 A1 | 4/2005 | Andreas et al. |
| 2005/0085888 A1 | 4/2005 | Andreas et al. |
| 2005/0085897 A1 | 4/2005 | Bonsignore |
| 2005/0090846 A1 | 4/2005 | Pedersen et al. |
| 2005/0101624 A1 | 5/2005 | Betts et al. |
| 2005/0123451 A1 | 6/2005 | Nomura |
| 2005/0125051 A1 | 6/2005 | Eidenschink et al. |
| 2005/0131008 A1 | 6/2005 | Betts et al. |
| 2005/0133164 A1 | 6/2005 | Fischer et al. |
| 2005/0137622 A1 | 6/2005 | Griffin |
| 2005/0143827 A1 | 6/2005 | Globerman et al. |
| 2005/0149159 A1 | 7/2005 | Andreas et al. |
| 2005/0149168 A1 | 7/2005 | Gregorich |
| 2005/0165378 A1 | 7/2005 | Heinrich et al. |
| 2005/0171568 A1 | 8/2005 | Duffy |
| 2005/0182477 A1 | 8/2005 | White |
| 2005/0209674 A1 | 9/2005 | Kutscher et al. |
| 2005/0209676 A1 | 9/2005 | Kusleika |
| 2005/0209680 A1 | 9/2005 | Gale et al. |
| 2005/0222671 A1 | 10/2005 | Schaeffer et al. |
| 2005/0228477 A1 | 10/2005 | Grainger et al. |
| 2005/0245637 A1 | 11/2005 | Hossainy et al. |
| 2005/0249777 A1 | 11/2005 | Michal et al. |
| 2005/0278011 A1 | 12/2005 | Peckham |
| 2005/0288763 A1 | 12/2005 | Andreas et al. |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0173529 A1 | 8/2006 | Blank |
| 2006/0177476 A1 | 8/2006 | Saffran |
| 2006/0200223 A1 | 9/2006 | Andreas et al. |
| 2006/0206190 A1 | 9/2006 | Chermoni |
| 2006/0229700 A1 | 10/2006 | Acosta et al. |
| 2006/0229706 A1 | 10/2006 | Shulze et al. |
| 2006/0271150 A1 | 11/2006 | Andreas et al. |
| 2006/0271151 A1 | 11/2006 | McGarry et al. |
| 2006/0282147 A1 | 12/2006 | Andreas et al. |
| 2006/0282149 A1 | 12/2006 | Kao |
| 2006/0282150 A1 | 12/2006 | Olson et al. |
| 2006/0287726 A1 | 12/2006 | Segal et al. |
| 2007/0010869 A1 | 1/2007 | Sano |
| 2007/0027521 A1 | 2/2007 | Andreas et al. |
| 2007/0043419 A1 | 2/2007 | Nikolchev et al. |
| 2007/0067012 A1 | 3/2007 | George et al. |
| 2007/0088368 A1 | 4/2007 | Acosta et al. |
| 2007/0088420 A1 | 4/2007 | Andreas et al. |
| 2007/0088422 A1 | 4/2007 | Chew et al. |
| 2007/0100423 A1 | 5/2007 | Acosta et al. |
| 2007/0100424 A1 | 5/2007 | Chew et al. |
| 2007/0106365 A1 | 5/2007 | Andreas et al. |
| 2007/0118202 A1 | 5/2007 | Chermoni |
| 2007/0118203 A1 | 5/2007 | Chermoni |
| 2007/0118204 A1 | 5/2007 | Chermoni |
| 2007/0129733 A1 | 6/2007 | Will et al. |
| 2007/0135906 A1 | 6/2007 | Badylak et al. |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0219612 A1 | 9/2007 | Andreas et al. |
| 2007/0219613 A1 | 9/2007 | Kao et al. |
| 2007/0265637 A1 | 11/2007 | Andreas et al. |
| 2007/0270936 A1 | 11/2007 | Andreas et al. |
| 2007/0276461 A1 | 11/2007 | Andreas et al. |
| 2007/0281117 A1 | 12/2007 | Kaplan et al. |
| 2007/0292518 A1 | 12/2007 | Ludwig |
| 2008/0004690 A1 | 1/2008 | Robaina |
| 2008/0046067 A1 | 2/2008 | Toyokawa |
| 2008/0071345 A1 | 3/2008 | Hammersmark et al. |
| 2008/0077229 A1 | 3/2008 | Andreas et al. |
| 2008/0091257 A1 | 4/2008 | Andreas et al. |
| 2008/0097299 A1 | 4/2008 | Andreas et al. |
| 2008/0097574 A1 | 4/2008 | Andreas et al. |
| 2008/0125850 A1 | 5/2008 | Andreas et al. |
| 2008/0132989 A1 | 6/2008 | Snow et al. |
| 2008/0147162 A1 | 6/2008 | Andreas et al. |
| 2008/0177369 A1 | 7/2008 | Will et al. |
| 2008/0199510 A1 | 8/2008 | Ruane et al. |
| 2008/0208311 A1 | 8/2008 | Kao et al. |
| 2008/0208318 A1 | 8/2008 | Kao et al. |
| 2008/0234795 A1 | 9/2008 | Snow et al. |
| 2008/0234798 A1 | 9/2008 | Chew et al. |
| 2008/0234799 A1 | 9/2008 | Acosta et al. |
| 2008/0243225 A1 | 10/2008 | Satasiya et al. |
| 2008/0249607 A1 | 10/2008 | Webster et al. |
| 2008/0269865 A1 | 10/2008 | Snow et al. |
| 2009/0076584 A1 | 3/2009 | Mao et al. |
| 2009/0088832 A1 | 4/2009 | Chew et al. |
| 2009/0105686 A1 | 4/2009 | Snow et al. |
| 2009/0149863 A1 | 6/2009 | Andreas et al. |
| 2009/0228088 A1 | 9/2009 | Lowe et al. |
| 2009/0234428 A1 | 9/2009 | Snow et al. |
| 2009/0248137 A1 | 10/2009 | Andersen et al. |

(56) References Cited

U.S. PATENT DOCUMENTS

| | | |
|---|---|---|
| 2009/0248140 A1 | 10/2009 | Gerberding |
| 2009/0264979 A1 | 10/2009 | Kao et al. |
| 2009/0276030 A1 | 11/2009 | Kusleika |
| 2010/0004729 A1 | 1/2010 | Chew et al. |
| 2011/0022148 A1 | 1/2011 | Ruane et al. |
| 2011/0093056 A1 | 4/2011 | Kaplan et al. |
| 2011/0125248 A1 | 5/2011 | George et al. |
| 2011/0152996 A1 | 6/2011 | Snow et al. |
| 2013/0060321 A1 | 3/2013 | Kao et al. |
| 2013/0211494 A1 | 8/2013 | Snow et al. |
| 2014/0018899 A1 | 1/2014 | Snow et al. |
| 2014/0188205 A1 | 7/2014 | Andreas et al. |
| 2014/0236282 A1 | 8/2014 | Andreas et al. |

FOREIGN PATENT DOCUMENTS

| | | |
|---|---|---|
| DE | 1 953 1659 | 6/1997 |
| DE | 1 963 0469 | 1/1998 |
| DE | 199 50 756 | 8/2000 |
| DE | 101 03 000 | 8/2002 |
| EP | 0 203 945 B2 | 12/1986 |
| EP | 0 274 129 B1 | 7/1988 |
| EP | 0 282 143 A1 | 9/1988 |
| EP | 0 364 787 A1 | 4/1990 |
| EP | 0 505 686 | 9/1992 |
| EP | 0 533 960 | 3/1993 |
| EP | 0 596 145 | 5/1994 |
| EP | 0 696 447 A2 | 2/1996 |
| EP | 0 714 640 A1 | 6/1996 |
| EP | 0 797 963 A2 | 10/1997 |
| EP | 0 947 180 | 10/1999 |
| EP | 1 254 644 A1 | 11/2002 |
| EP | 1 258 230 | 11/2002 |
| EP | 1 266 638 B1 | 12/2002 |
| EP | 1 277 449 | 1/2003 |
| EP | 1 290 987 A2 | 3/2003 |
| EP | 1 318 765 A2 | 6/2003 |
| EP | 1 470 834 | 10/2004 |
| EP | 1 523 959 A2 | 4/2005 |
| EP | 1 523 960 A2 | 4/2005 |
| EP | 1 743 603 A2 | 1/2007 |
| GB | 2277875 A | 11/1994 |
| JP | 03-133446 | 6/1991 |
| JP | 07-132148 | 5/1995 |
| JP | 10-503663 | 4/1998 |
| JP | 10-295823 | 11/1998 |
| JP | 11-503056 T | 3/1999 |
| JP | 2935561 B2 | 8/1999 |
| JP | 2001-190687 | 7/2001 |
| JP | 2002-538932 T | 11/2002 |
| JP | 2004-121343 A | 4/2004 |
| WO | 94/27667 A1 | 12/1994 |
| WO | 95/26695 A2 | 10/1995 |
| WO | 95/29647 A2 | 11/1995 |
| WO | 96/26689 | 9/1996 |
| WO | 96/33677 | 10/1996 |
| WO | 96/37167 A1 | 11/1996 |
| WO | 96/39077 A1 | 12/1996 |
| WO | 97/10778 | 3/1997 |
| WO | 97/46174 | 12/1997 |
| WO | 97/48351 | 12/1997 |
| WO | 98/20810 | 5/1998 |
| WO | 98/37833 | 9/1998 |
| WO | 98/58600 | 12/1998 |
| WO | 99/01087 A1 | 1/1999 |
| WO | 99/47075 A1 | 9/1999 |
| WO | 99/65421 | 12/1999 |
| WO | 00/12832 A3 | 3/2000 |
| WO | 00/15151 A1 | 3/2000 |
| WO | 00/25841 | 5/2000 |
| WO | 00/32136 | 6/2000 |
| WO | 00/41649 | 7/2000 |
| WO | 00/50116 | 8/2000 |
| WO | 00/51525 A1 | 9/2000 |
| WO | 00/56237 | 9/2000 |
| WO | 00/62708 | 10/2000 |
| WO | 00/72780 | 12/2000 |
| WO | 01/26707 | 4/2001 |
| WO | 01/34063 | 5/2001 |
| WO | 01/70297 | 9/2001 |
| WO | 01/91918 A1 | 12/2001 |
| WO | 02/060344 | 8/2002 |
| WO | 02/071975 | 9/2002 |
| WO | 02/085253 A1 | 10/2002 |
| WO | 02/098326 A1 | 12/2002 |
| WO | 03/022178 A1 | 3/2003 |
| WO | 03/047651 | 6/2003 |
| WO | 03/051425 | 6/2003 |
| WO | 03/075797 | 9/2003 |
| WO | 2004/017865 | 3/2004 |
| WO | 2004/043299 A1 | 5/2004 |
| WO | 2004/043301 | 5/2004 |
| WO | 2004/043510 | 5/2004 |
| WO | 2004/052237 A2 | 6/2004 |
| WO | 2004/087006 | 10/2004 |
| WO | 2004/091441 | 10/2004 |
| WO | 2005/009295 A1 | 2/2005 |
| WO | 2005/013853 | 2/2005 |
| WO | 2005/023153 | 3/2005 |
| WO | 2006/036939 | 4/2006 |
| WO | 2006/047520 | 5/2006 |
| WO | 2007/035805 | 3/2007 |
| WO | 2007/053187 A2 | 5/2007 |
| WO | 2007/146411 | 12/2007 |
| WO | 2008/005111 | 1/2008 |
| WO | 2009/111203 A2 | 9/2009 |

OTHER PUBLICATIONS

Supplementary Partial European Search Report of EP Patent Application No. 05778125, dated Nov. 6, 2014, 4 pages.

International Search Report and Written Opinion of PCT Application No. PCT/US2009/034889 mailed Apr. 22, 2009, 12 pages.

Chu et al., "Preparation of Thermo-Responsive Core-Shell Microcapsules with a Porous Membrane and Poly(N-isopropylacrylamide) Gates," J Membrane Sci, Oct. 15, 2001; 192(1-2):27-39.

Colombo, "The Invatec Bifurcation Stent Solution" Bifurcation Stents: Novel Solutions, TCT 2003, Washington: Sep. 15-19, 2003, 24 pages total.

Cooley et al., "Applications of Ink-Jet Printing Technology to BioMEMs and Microfluidic Systems," Proceedings, SPIE Conference on Microfluidics and BioMEMs, (Oct. 2001).

"Drug Delivery Stent With Holes Located on Neutral Axis" Research Disclosure, Kenneth Mason Publications, Hampshire, CB, No. 429, Jan. 2000, p. 13.

Evans Analytical Group, "Functional Sites on Non-polymeric Materials: Gas Plasma Treatment and Surface Analysis," http://www.eaglabs.com.

Joung et al., "Estrogen Release from Metallic Stent Surface for the Prevention of Restenosis," J Control Release. Sep. 19, 2003;92(1-2):83-91.

Lefevre et al. "Approach to Coronary Bifurcation Stenting in 2003," Euro PCR, (May 2003) 28 pages total.

"Stent". Definitions from Dictionary.com. Unabridged 9v1.01). Retrieved Sep. 22, 2006, from Dictionary.com website: <http://dictionary.reference.com/search?q=stent>.

Stimpson et al., "Parallel Production of Oligonucleotide Arrays Using Membranes and Reagent Jet Printing," BioTechniques 25:886-890 (Nov. 1998).

Tilley, "Biolimus A9-Eluting Stent Shows Promise," Medscape Medical News, Oct. 5, 2004; retrieved from the internet: <http://www.medscape.com/viewarticle/490621>, 2 pages total.

Weir et al., "Degradation of poly-L-lactide. Part 2: increased temperature accelerated degradation," Proc Inst Mech Eng H. 2004;218(5):321-30.

Supplementary European Search Report of EP Patent Application No. 02804509, dated Dec. 13, 2006, 2 pages total.

Supplementary European Search Report of EP Patent Application No. 04749567, dated Sep. 11, 2006, 2 pages total.

(56) References Cited

OTHER PUBLICATIONS

Supplementary European Search Report of EP Patent Application No. 05727731.1, dated Mar. 25, 2008, 2 pages total.

Supplementary European Search Report of EP Patent Application No. 05744136, dated Mar. 26, 2008, 3 pages total.

U.S. Appl. No. 60/336,607, filed Dec. 3, 2001, first named inventor: Bernard Andreas.

U.S. Appl. No. 60/336,767, filed Dec. 3, 2001, first named inventor: Bernard Andreas.

U.S. Appl. No. 60/336,967, filed Dec. 3, 2001, first named inventor: Sunmi Chew.

U.S. Appl. No. 60/364,389, filed Mar. 13, 2002, first named inventor: Sunmi Chew.

U.S. Appl. No. 60/440,839, filed Jan. 17, 2003, first named inventor: Bernard Andreas.

U.S. Appl. No. 60/561,041, filed Apr. 9, 2004, first named inventor: Jeffry Grainger.

U.S. Appl. No. 60/784,309, filed Mar. 20, 2006, first named inventor: Bernard Andreas.

U.S. Appl. No. 60/810,522, filed Jun. 2, 2006, first named inventor: Stephen Kaplan.

U.S. Appl. No. 60/890,703, filed Feb. 20, 2007, first named inventor: Patrick Ruane.

U.S. Appl. No. 09/097,855, filed Jun. 15, 1998, first named inventor: Enrique J. Klein; Abandoned.

U.S. Appl. No. 09/225,364, filed Jan. 4, 1999, first named inventor: Aaron V. Kaplan; Abandoned.

U.S. Appl. No. 10/874,859, filed Jun. 22, 2004, first named inventor: Pablo Acosta; Abandoned.

U.S. Appl. No. 11/462,951, filed Aug. 7, 2006, first named inventor: David Snow; Abandoned.

International Search Report and Written Opinion of PCT Application No. PCT/US2007/086864, mailed May 13, 2008, 13 pages total.

Supplementary European Search Report of EP Patent Application No. 07758831, dated Dec. 14, 2009, 6 pages.

International Search Report and Written Opinion of PCT Application No. PCT/US2008/061041, mailed Nov. 7, 2008, 13 pages total.

The State Intellectual Property Office of the Republic of China, Application No. 200880100150.2, First Office Action date of dispatch Oct. 26, 2011, 11 pages.

The State Intellectual Property Office of the People's Republic of China, Application No. 200880100150.2, Second Office Action date of dispatch Jul. 25, 2012, 23 pages.

Office Action of Japanese Patent Application No. 2006-547139, mailed Jun. 15, 2010, 5 pages total. (English translation included).

The State Intellectual Property Office of the People's Republic of China, 200880100150.2, Third Office Action date of dispatch Apr. 12, 2013, 26 pages.

\* cited by examiner

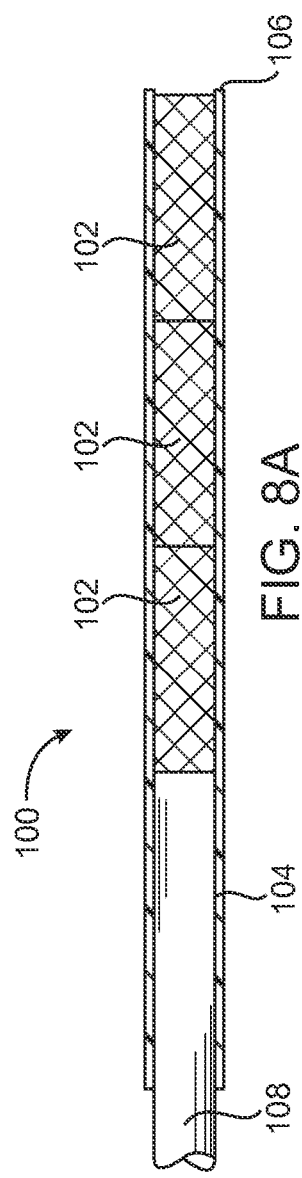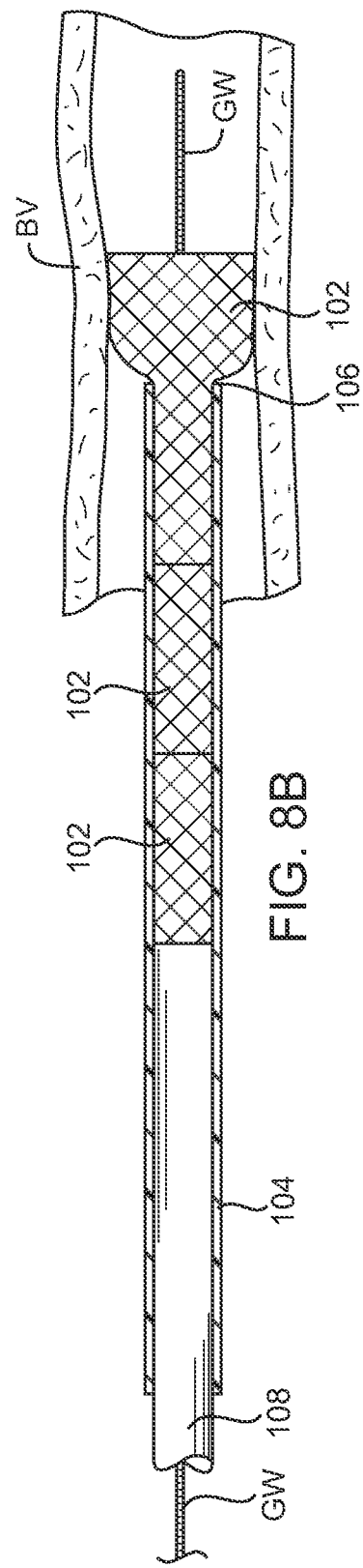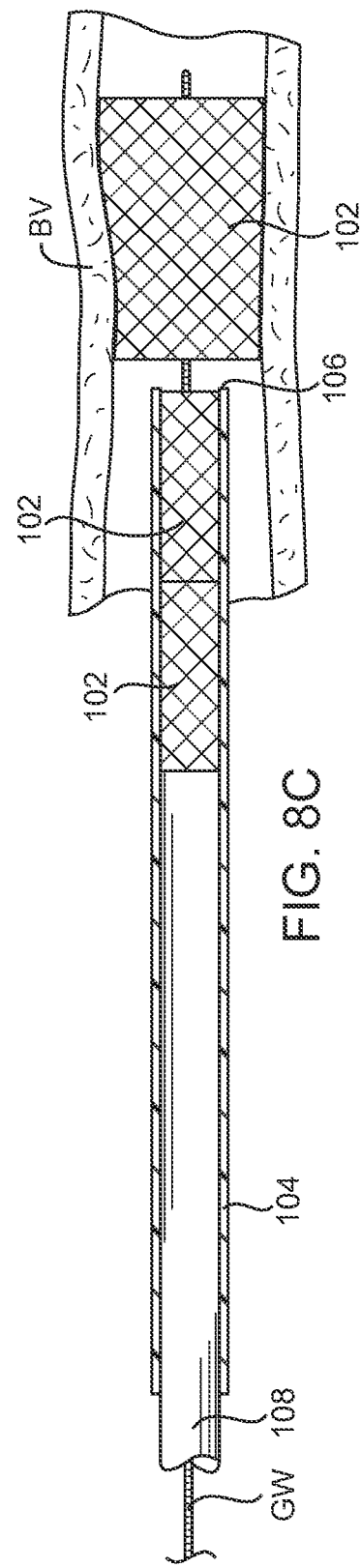

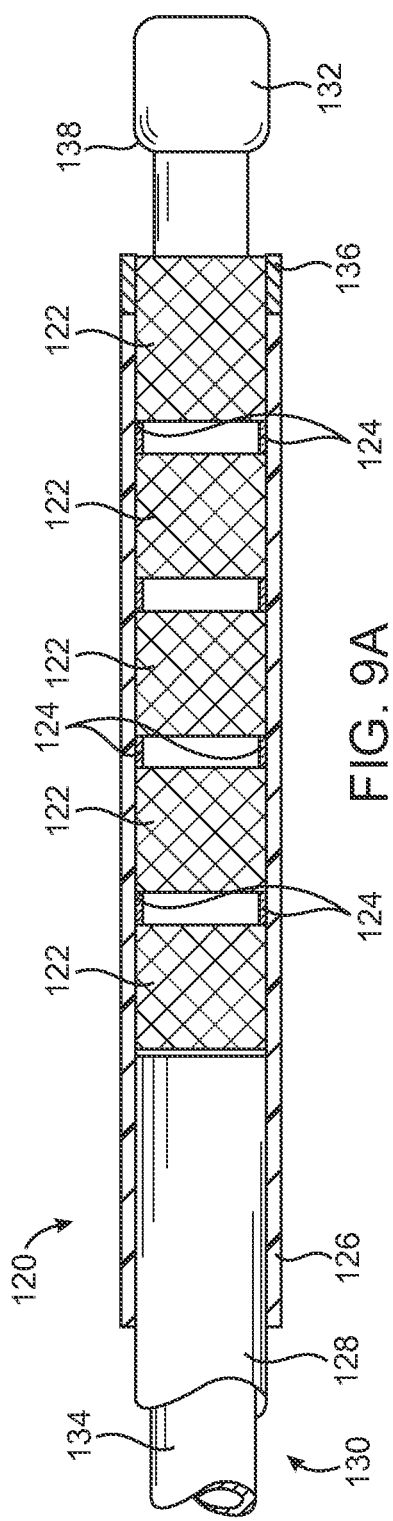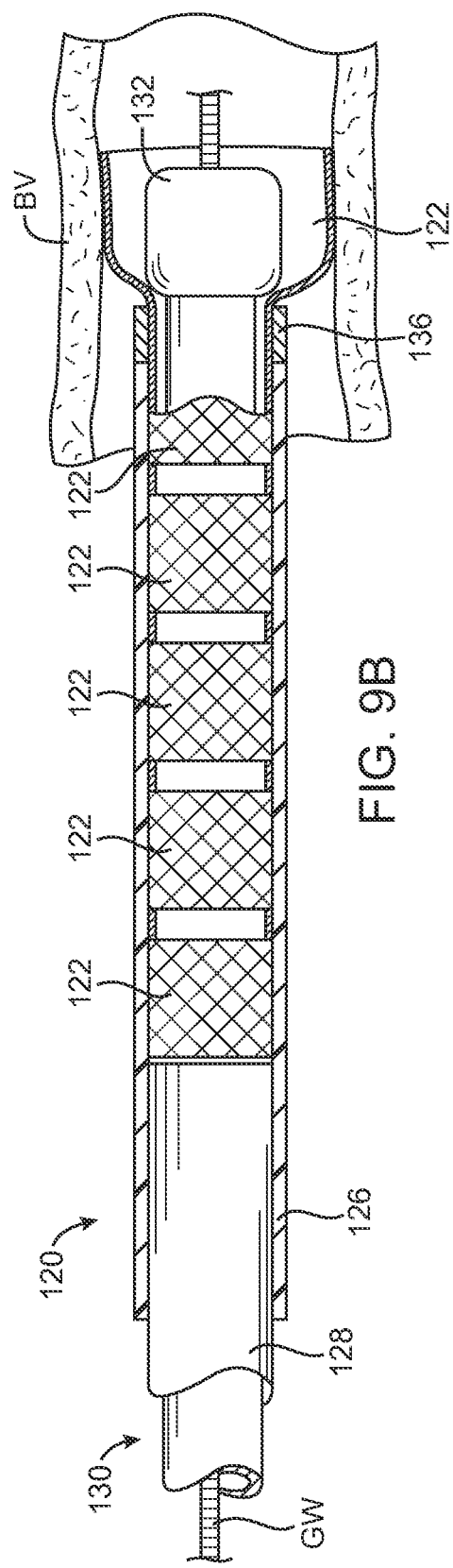

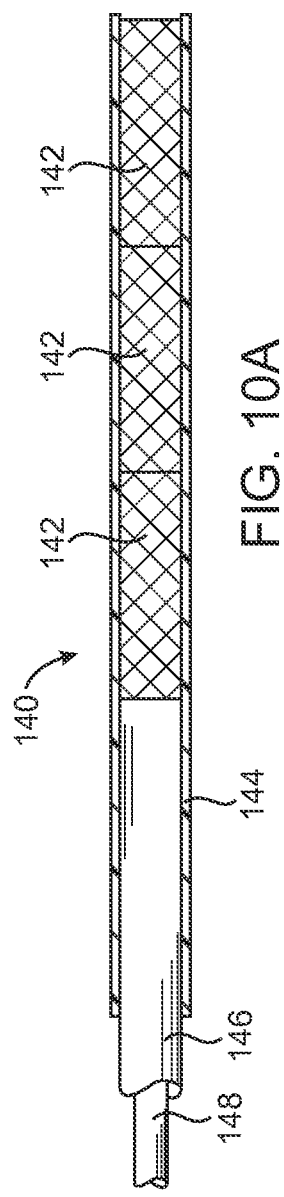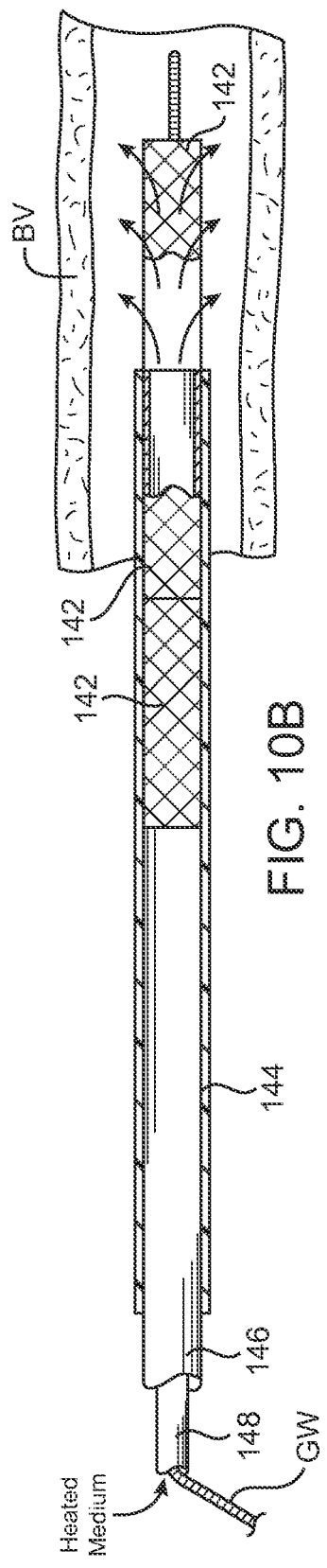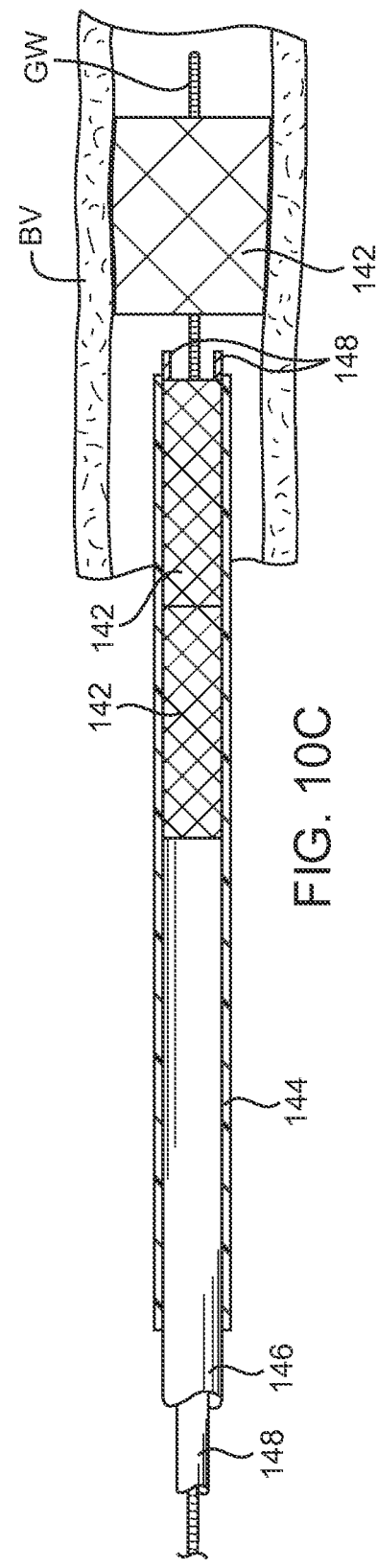

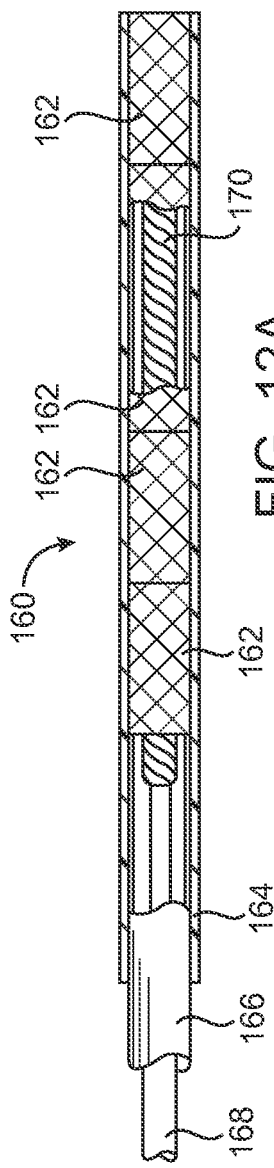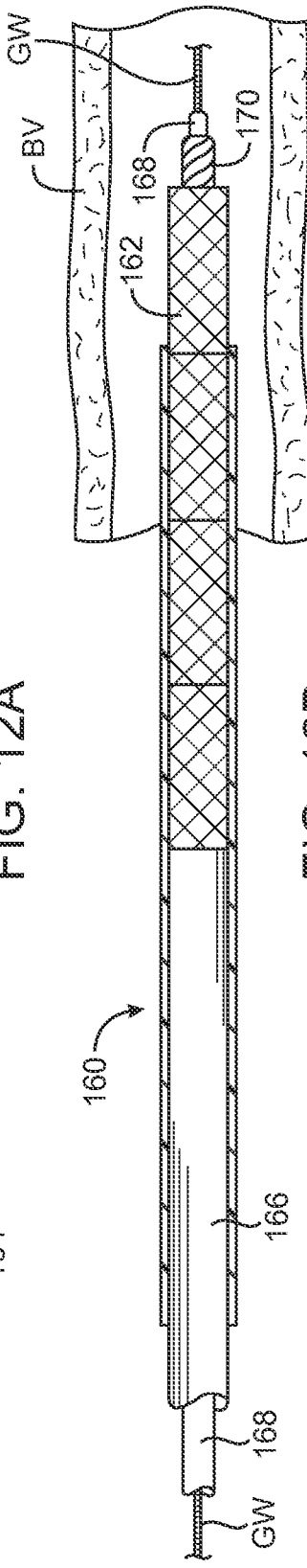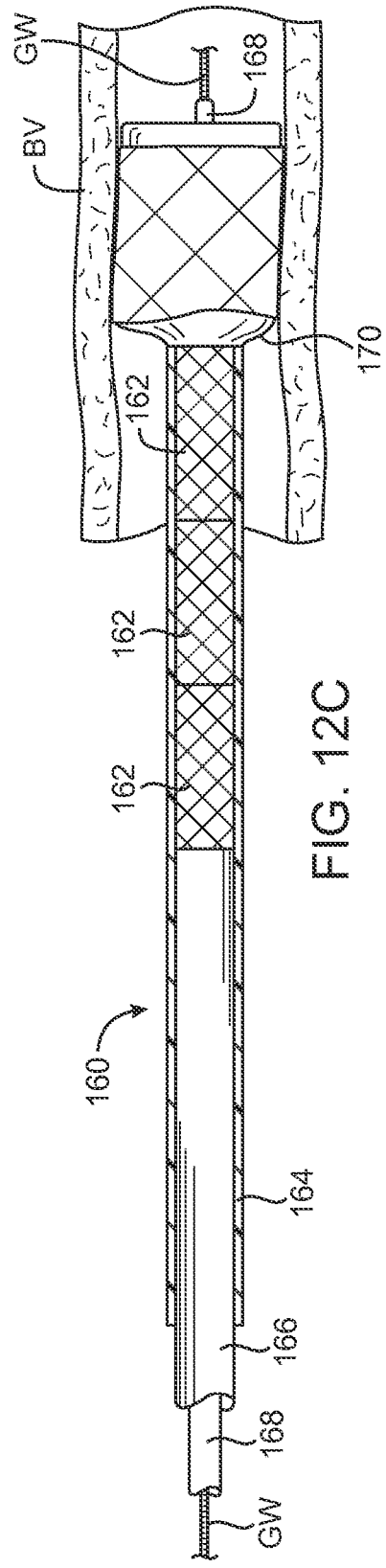
FIG. 12A
FIG. 12B
FIG. 12C

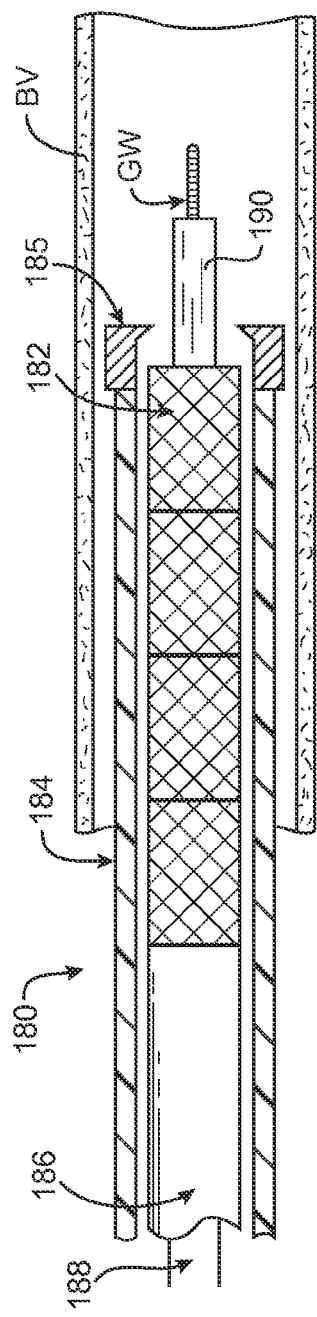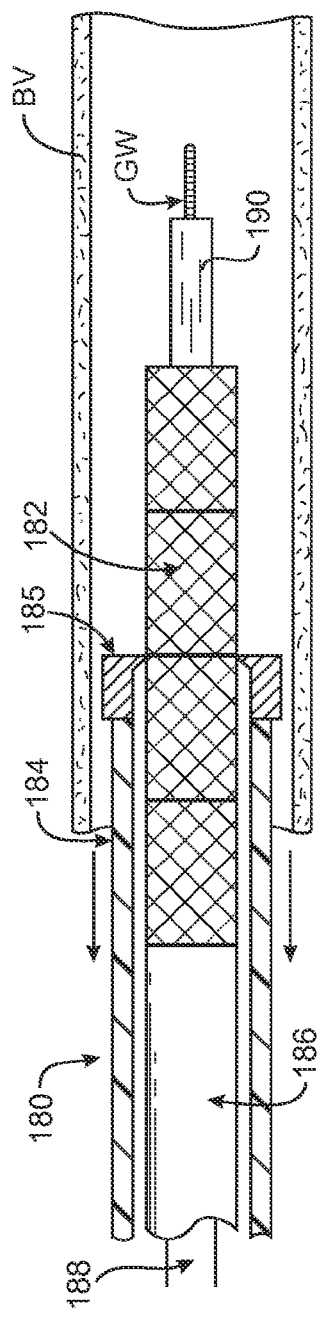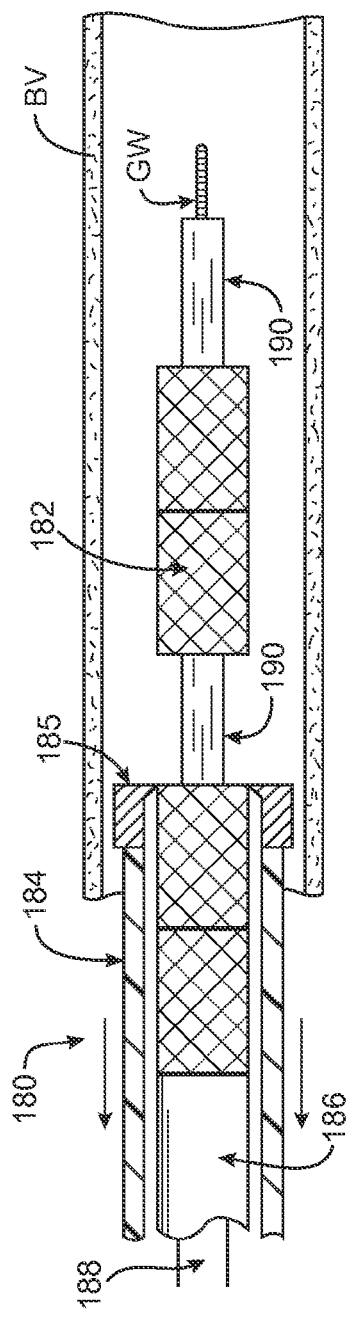

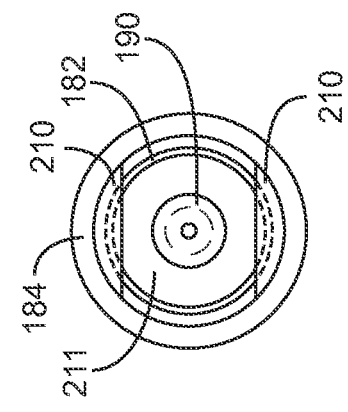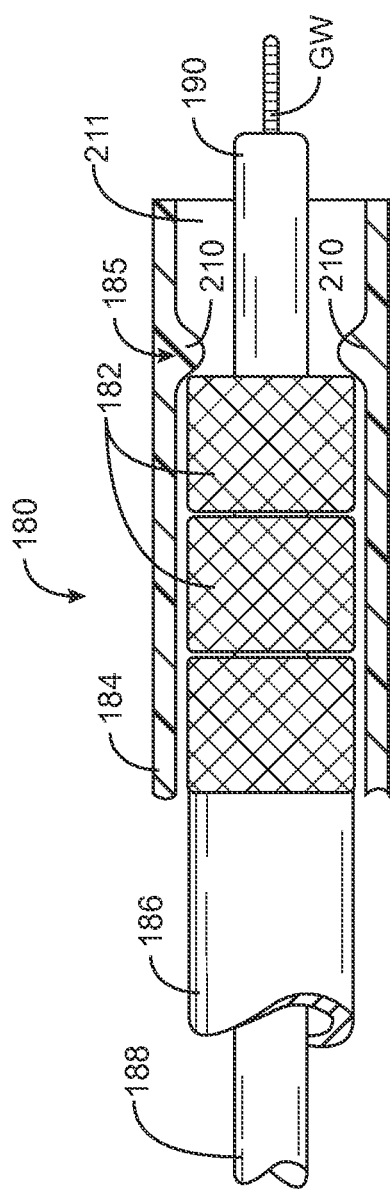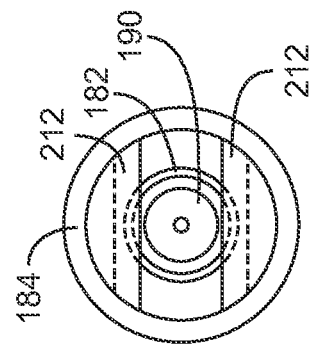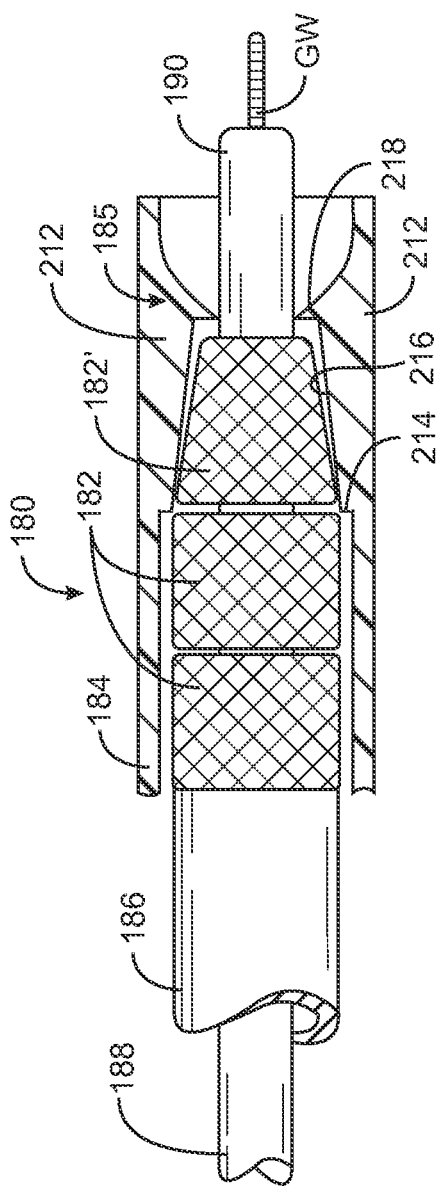

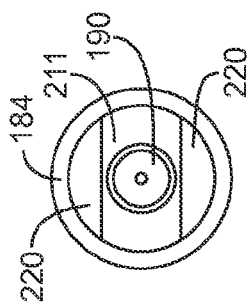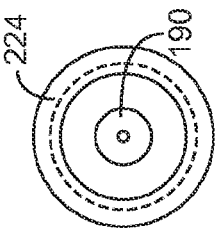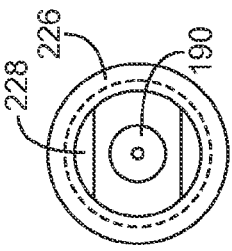
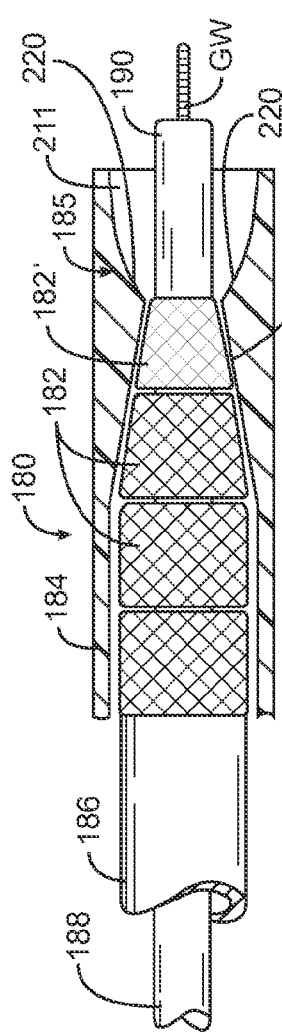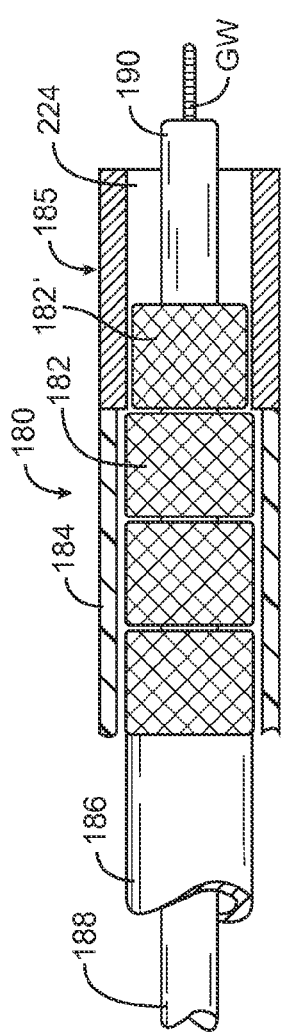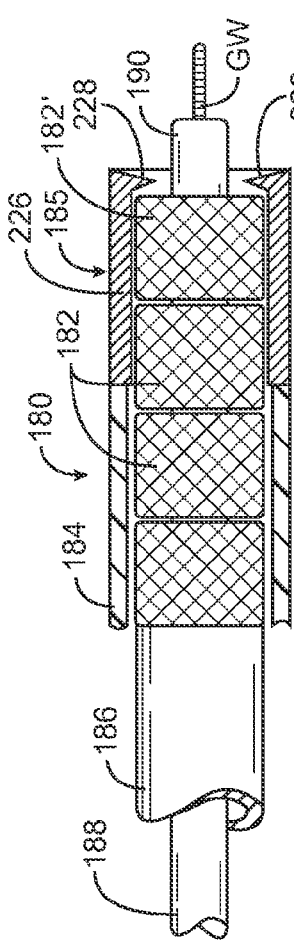

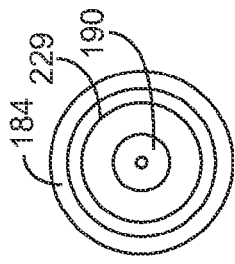 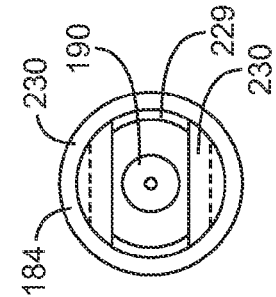 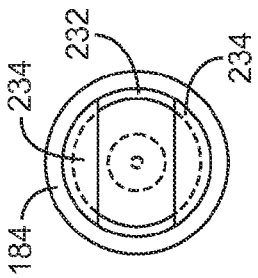
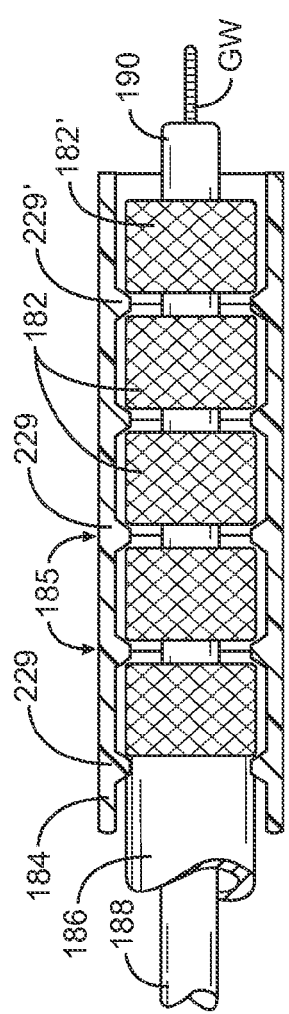 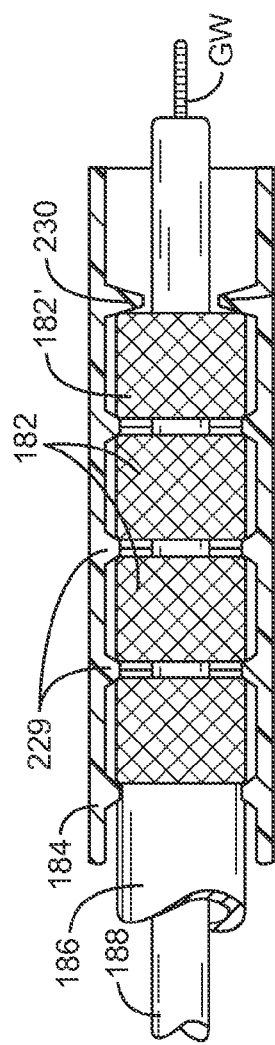 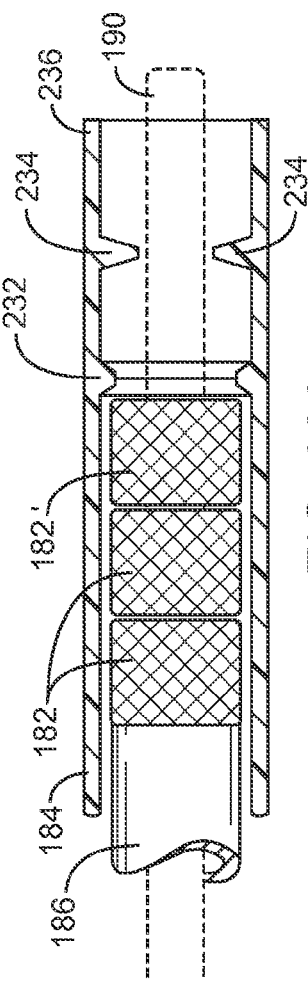

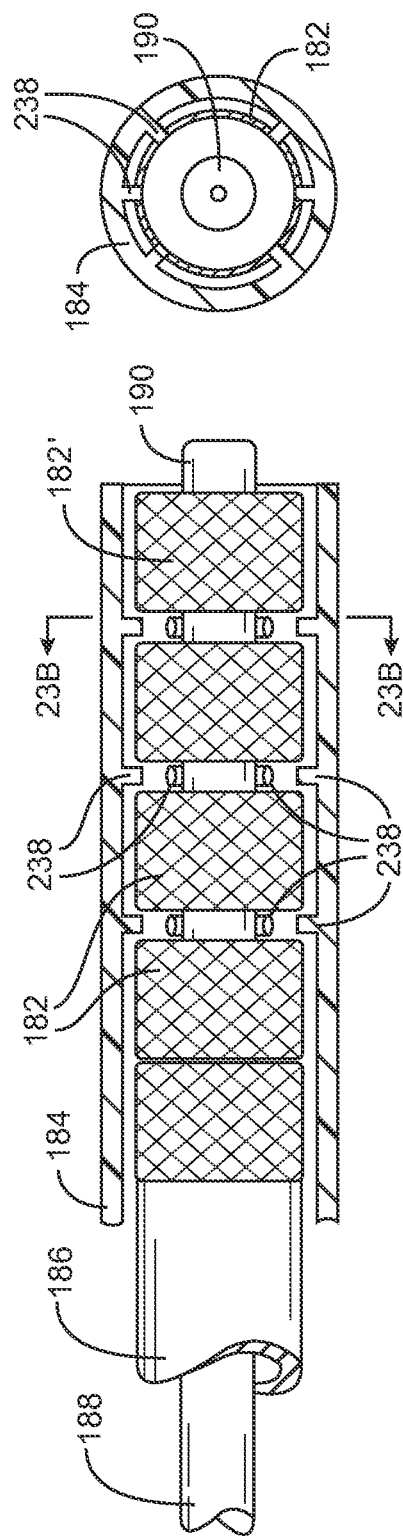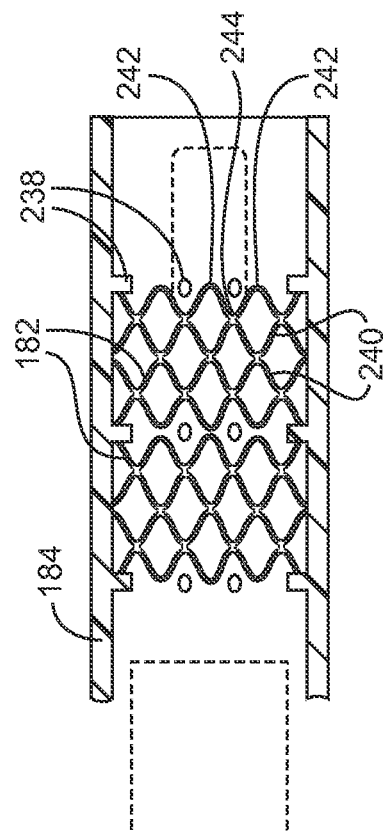

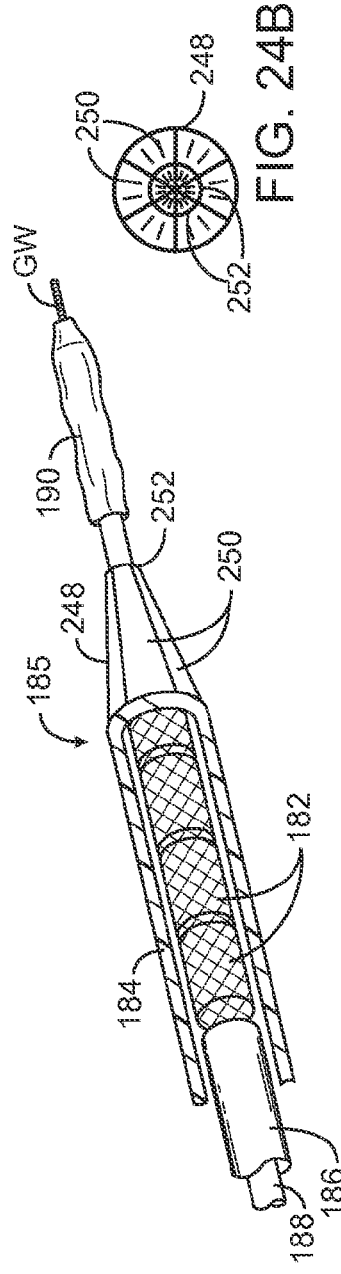
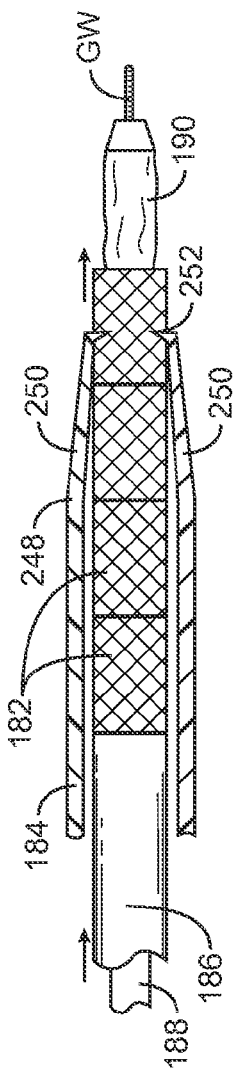
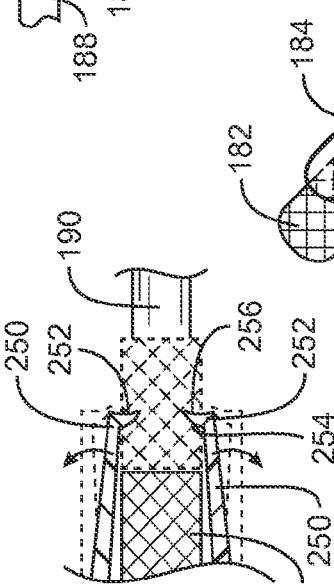
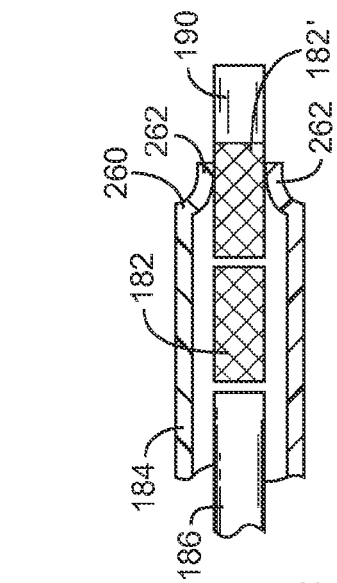
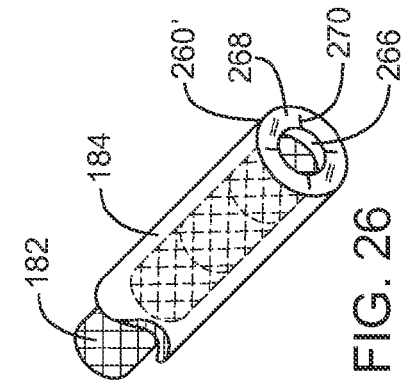

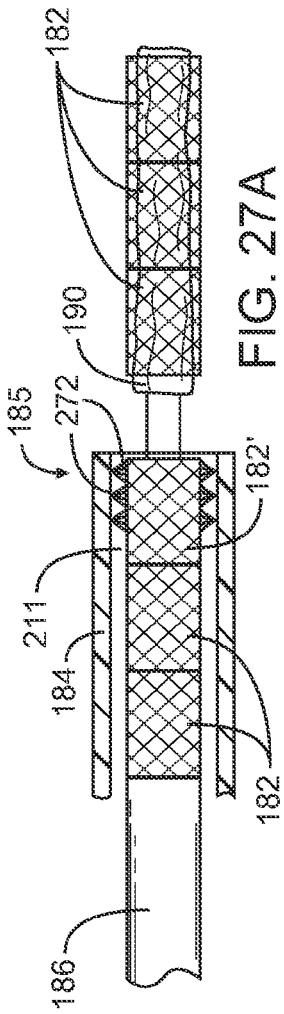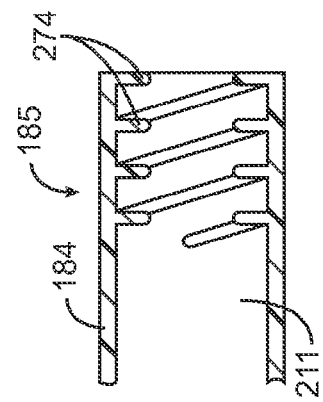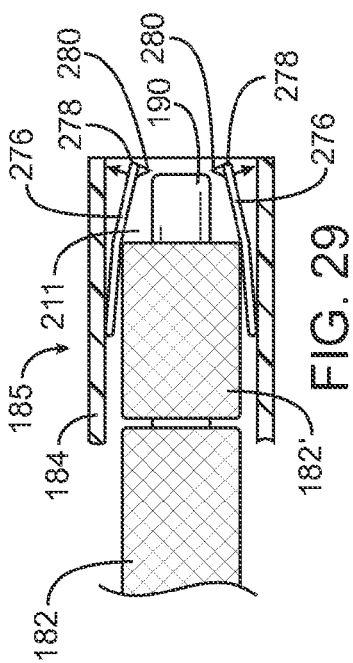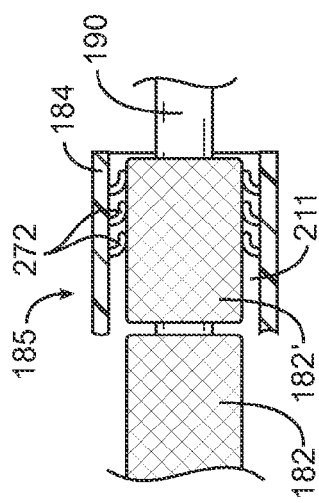

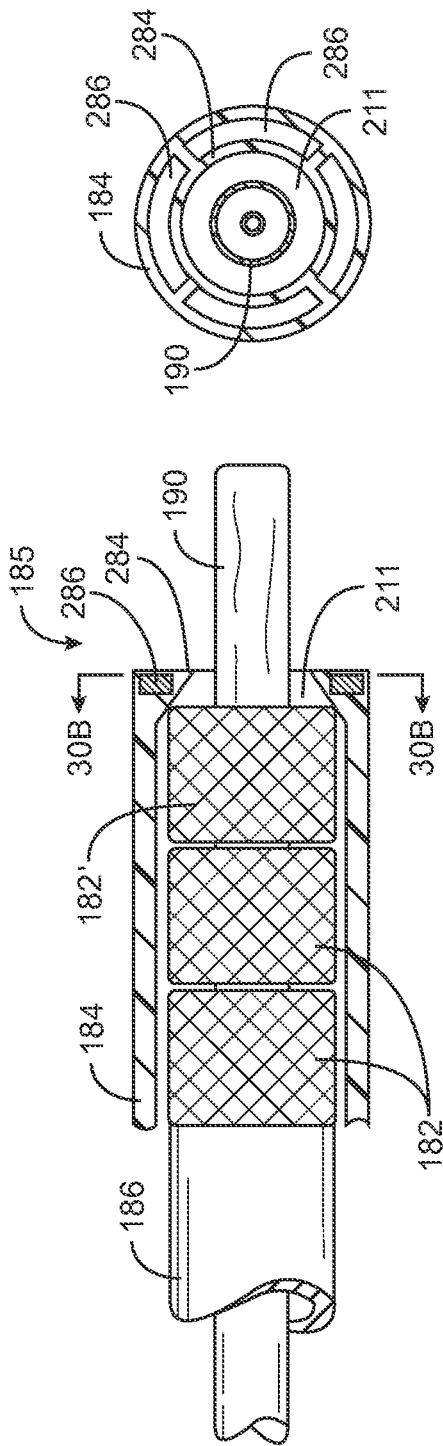
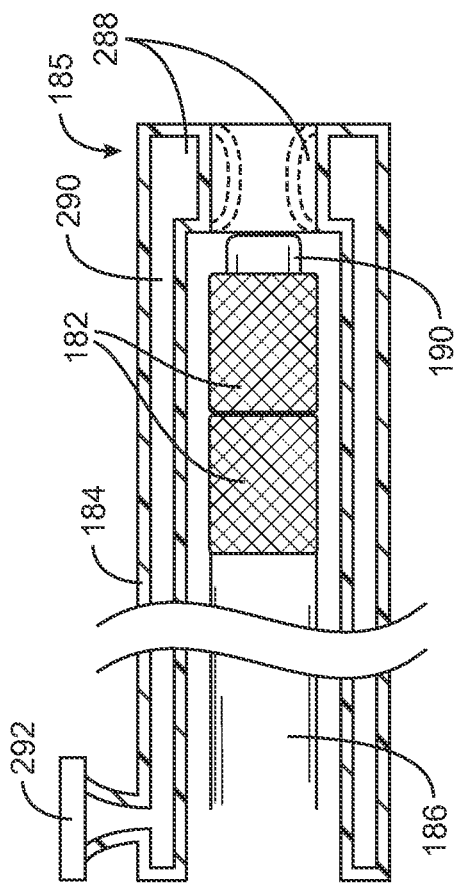

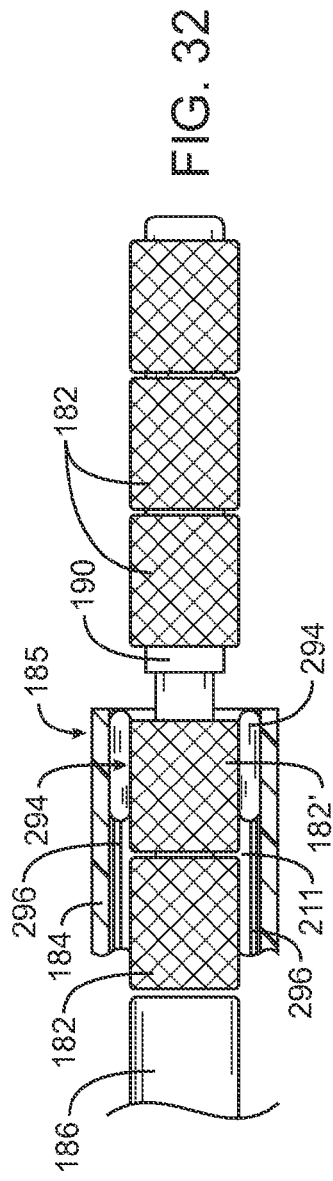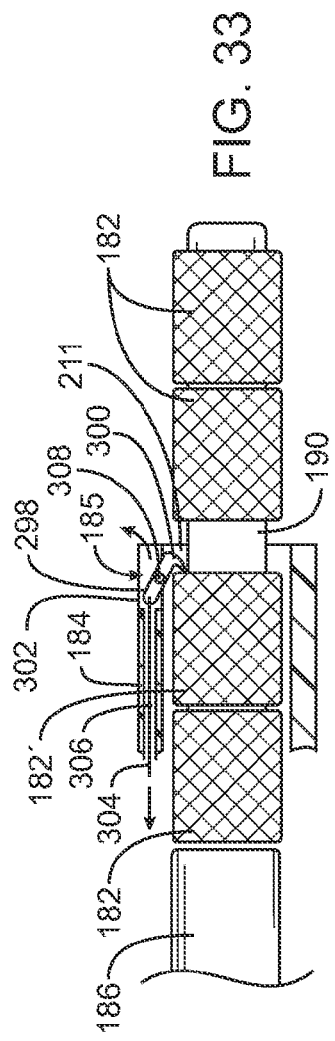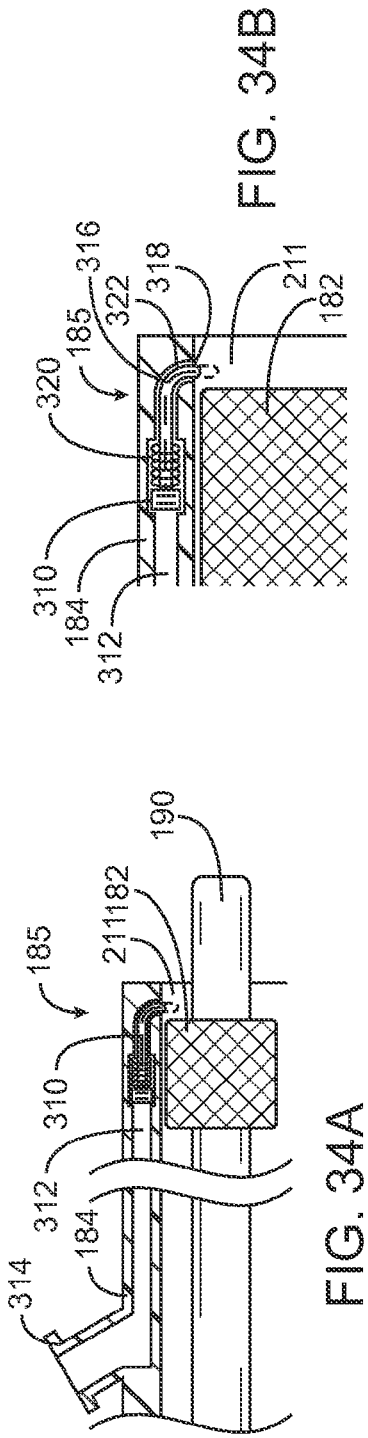

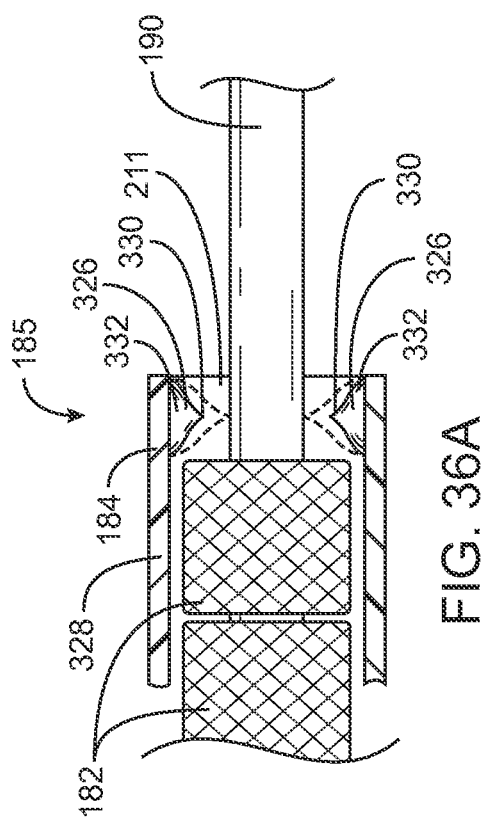
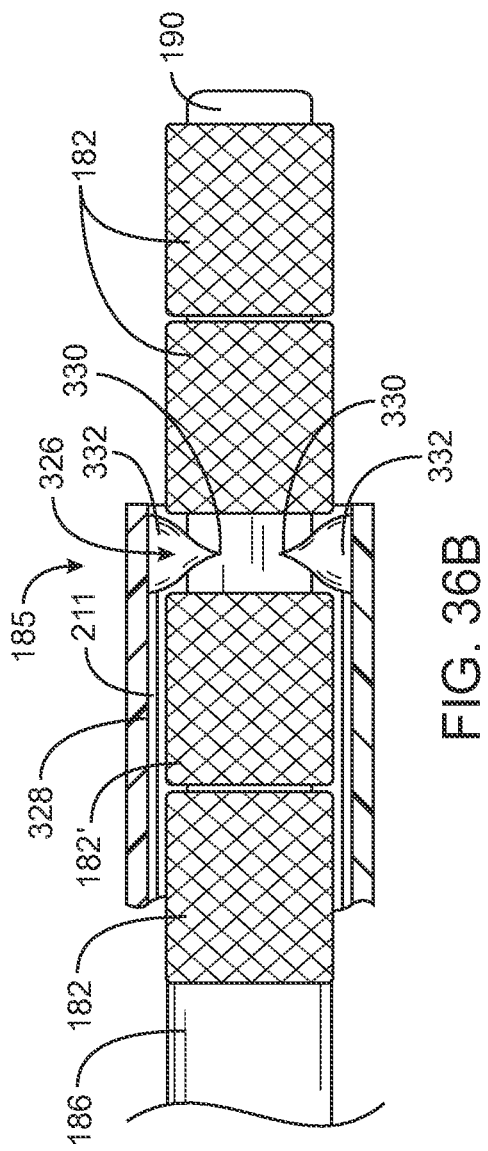
FIG. 36A
FIG. 36B

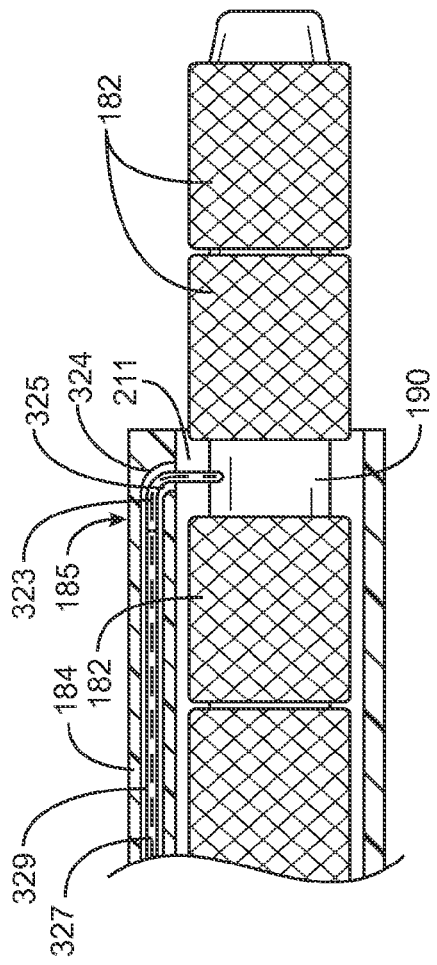
FIG. 35
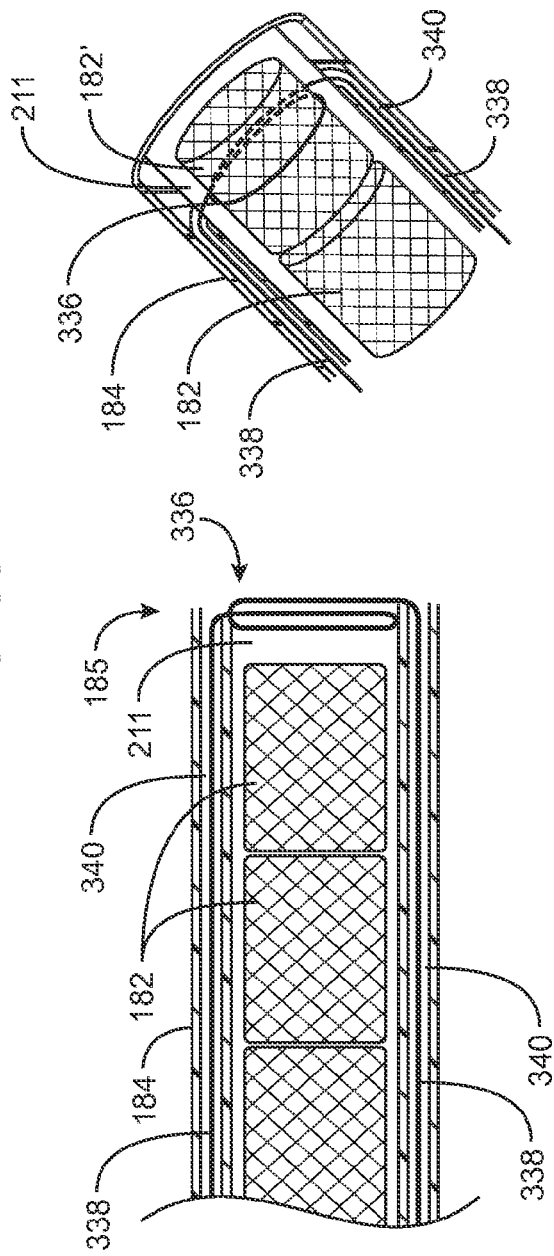
FIG. 37A
FIG. 37B

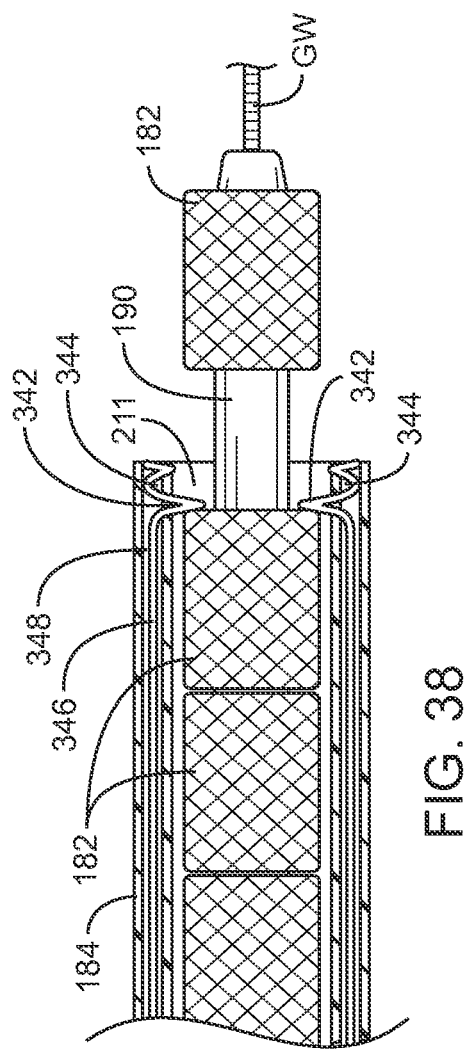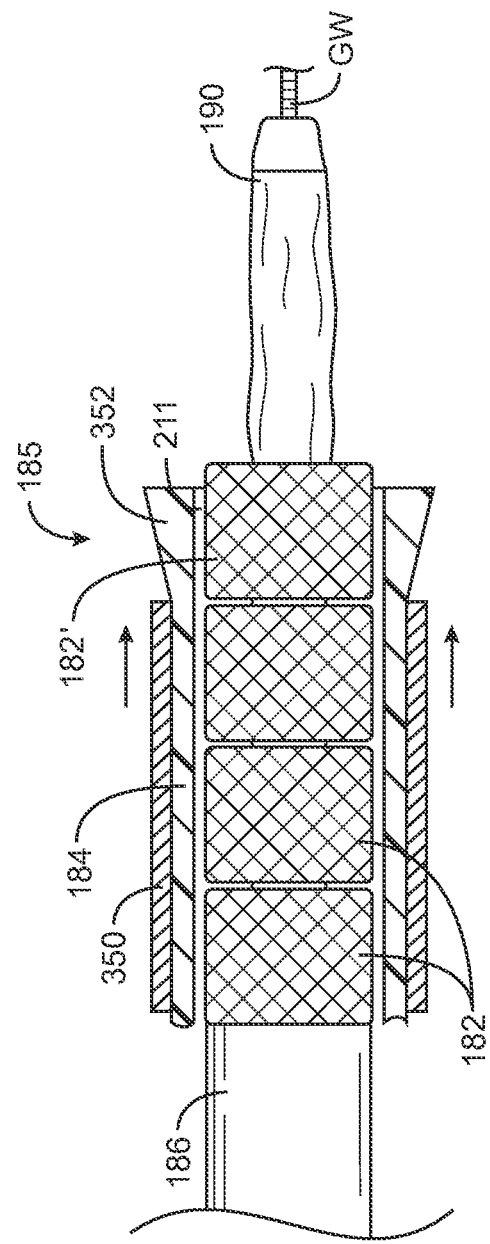

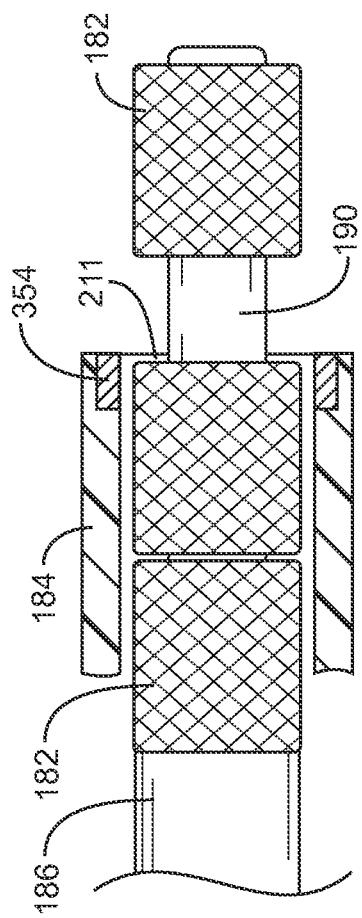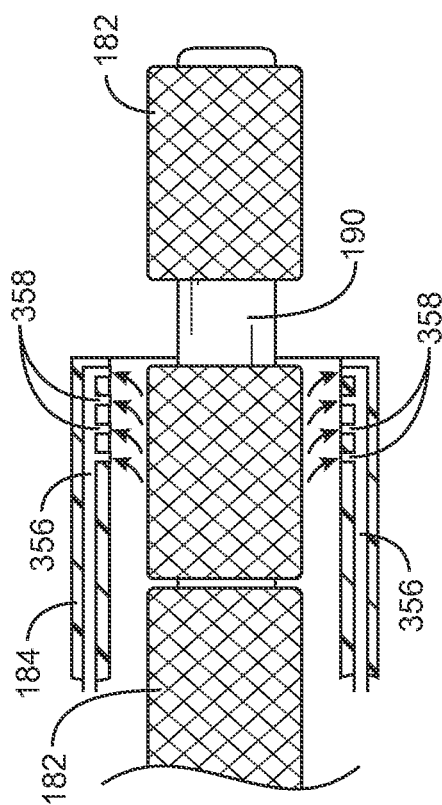

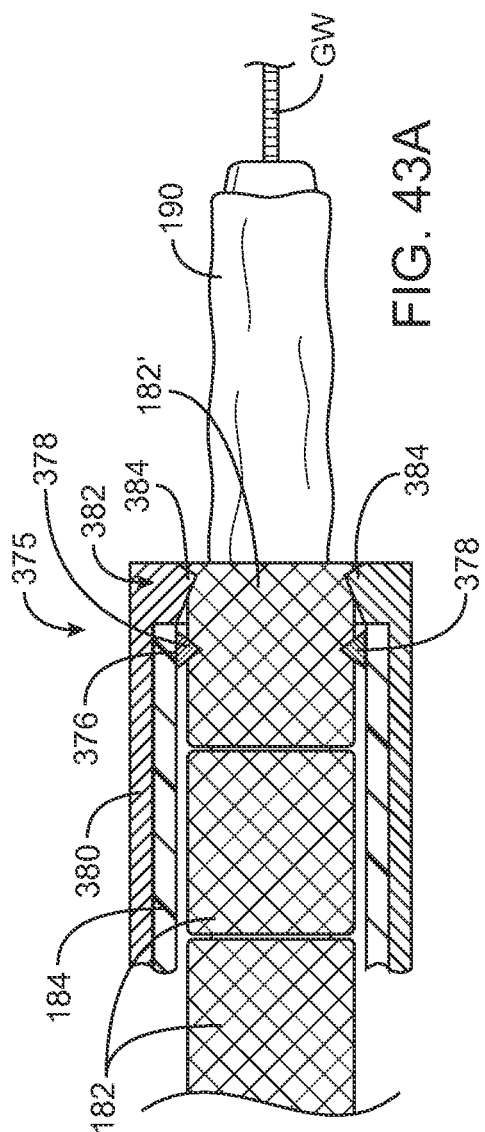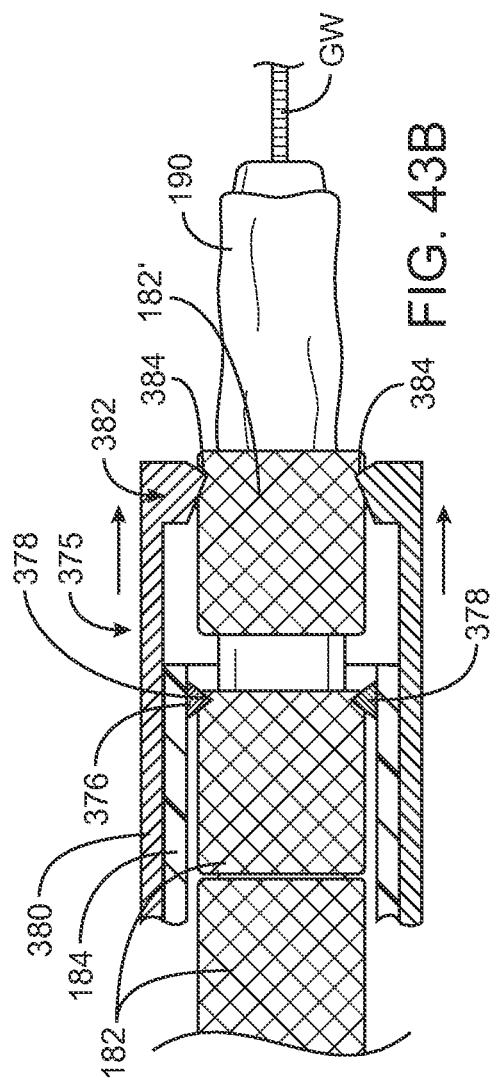

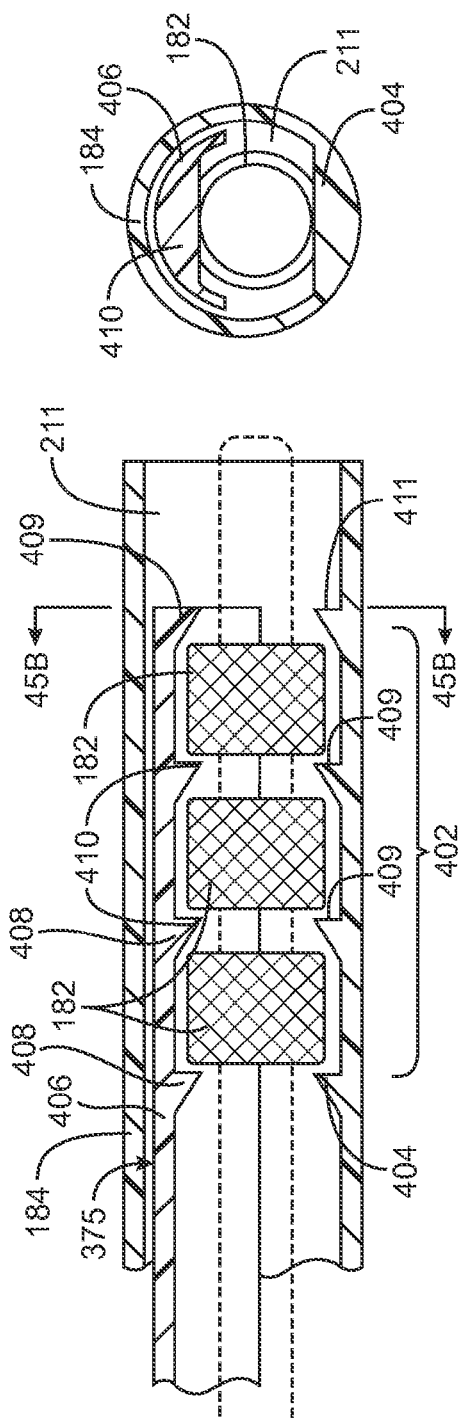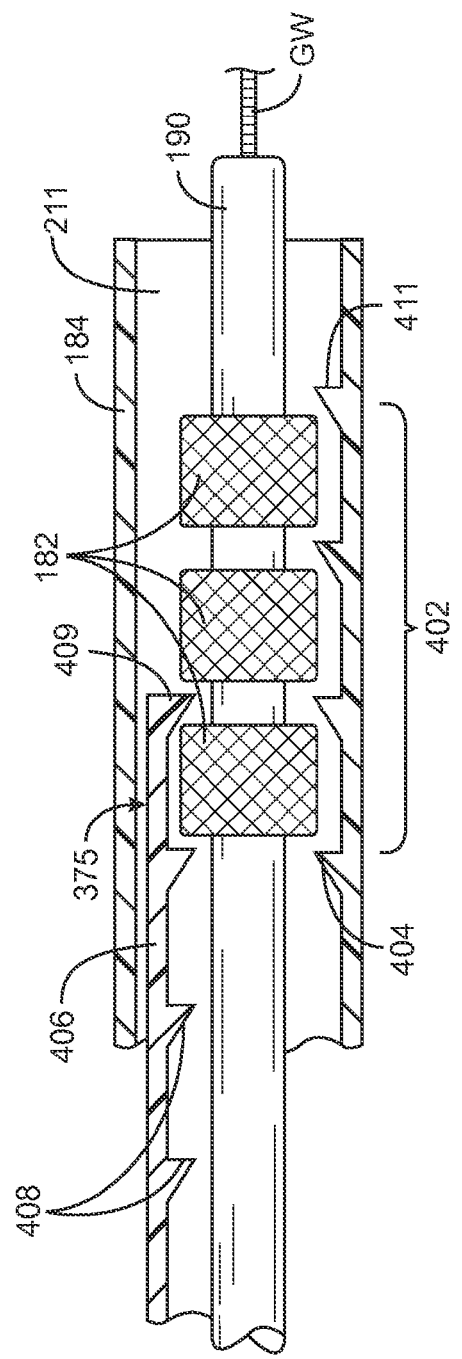

APPARATUS AND METHODS FOR DELIVERY OF MULTIPLE DISTRIBUTED STENTS

CROSS-REFERENCES TO RELATED APPLICATIONS

The present application is a divisional of U.S. patent application Ser. No. 13/037,140 filed Feb. 28, 2011, which is a continuation of U.S. patent application Ser. No. 11/538,904 filed Oct. 5, 2006, which is a divisional of U.S. patent application Ser. No. 10/412,714 filed Apr. 10, 2003, (now U.S. Pat. No. 7,137,993), which is a continuation-in-part of application Ser. No. 10/306,813, filed Nov. 27, 2002, which is a non-provisional of U.S. Patent Application Ser. No. 60/336,967 filed Dec. 3, 2001, and is also a non-provisional of U.S. patent application Ser. No. 60/364,389 filed on Mar. 13, 2002, the full disclosures of which are incorporated herein by reference.

BACKGROUND OF THE INVENTION

1. Field of the Invention

The present invention relates generally to medical devices and methods. More particularly, the present invention relates to apparatus and methods for independently delivering a plurality of luminal prostheses within a body lumen, such as a blood vessel.

Coronary artery disease is the leading cause of death and morbidity in the United States and Western society. In particular, atherosclerosis in the coronary arteries can cause myocardial infarction, commonly referred to as a heart attack, which can be immediately fatal or, even if survived, can cause damage to the heart which can incapacitate the patient.

While coronary artery bypass surgery can be an effective treatment for stenosed arteries resulting from atherosclerosis or other causes, it is a highly invasive, costly procedure, which typically requires substantial hospital and recovery time. Percutaneous transluminal coronary angioplasty, commonly referred to as balloon angioplasty, is less invasive, less traumatic, and significantly less expensive than bypass surgery. Heretofore, however, balloon angioplasty has not been considered as effective a treatment as bypass surgery. The effectiveness of balloon angioplasty, however, has improved significantly with the introduction of stenting which involves the placement of a scaffold structure within the artery which has been treated by balloon angioplasty. The stent inhibits abrupt reclosure of the artery and has some benefit in inhibiting subsequent restenosis resulting from hyperplasia. Recently, experimental trials have demonstrated that the coating of stents using anti-proliferative drugs, such as paclitaxel, can significantly reduce the occurrence of hyperplasia in angioplasty treated coronary arteries which have been stented with the coated stents.

While the combination of balloon angioplasty with drug-coated stents holds great promise, significant challenges still remain. Of particular interest to the present invention, the treatment of extended or disseminated disease within an artery remains problematic. Most stents have a fixed length, typically in the range from 10 mm to 30 mm, and the placement of multiple stents to treat disease over a longer length requires the suggestive use of balloon stent delivery catheters. Moreover, it can be difficult to stent an angioplasty-treated region of a blood vessel with the optimum stent length.

For these reasons, it would be desirable to provide improved stents, stent delivery systems, stenting methods, and the like, for the treatment of patients having coronary artery disease, as well as other occlusive diseases of the vasculature. In particular, it would be desirable to provide stents, delivery systems, and methods for the treatment of disseminated and variable length stenotic regions within the vasculature. For example, it would be desirable to provide a practical method which permits a physician to optimize the length of the treated vessel which is stented according to the nature of the disease. More specifically, it would be desirable to provide apparatus, systems, and methods for facilitating the delivery of multiple stents and other prostheses to blood vessels or other target body lumens. Such apparatus, systems, and methods should be suitable for delivery of individual stents or prostheses having very short lengths, typically as short as 3 mm or shorter, at multiple contiguous and non-contiguous locations within a body lumen for optimized treatment thereof. At least some of these objectives will be met by the inventions described hereinafter.

2. Description of the Background Art

U.S. Pat. No. 6,258,117 B1 describes a stent having multiple sections connected by separable or frangible connecting regions. Optionally, the connecting regions are severed after the stent structure has been implanted in the blood vessel. U.S. Pat. Nos. 5,571,086; 5,776,141; and 6,143,016 describe an expandable sleeve for placement over a balloon catheter for the delivery of one or two stent structures to the vasculature. U.S. Pat. No. 5,697,948 describes a catheter for delivering stents covered by a sheath.

BRIEF SUMMARY OF THE INVENTION

The present invention provides methods and apparatus for prosthesis placement, such as stenting of body lumens, typically blood vessels, and more typically coronary arteries. The methods and systems will also find significant use in the peripheral vasculature, the cerebral vasculature, and in other ducts, such as the biliary duct, the fallopian tubes, and the like. The terms "stent" and "stenting" are defined to include any of the wide variety of expandable prostheses and scaffolds which are designed to be intraluminally introduced to a treatment site and expanded in situ to apply a radially outward force against the inner wall of the body lumen at that site. Stents and prostheses commonly comprise an open lattice structure, typically formed from a malleable or elastic metal. When formed from a malleable metal, the stents will typically be expanded by a balloon which causes plastic deformation of the lattice so that it remains opened after deployment. When formed from an elastic metal, including super elastic metals such as nickel-titanium alloys, the lattice structures will usually be radially constrained when delivered and deployed by releasing the structures from such radial constraint so that they "self-expand" at the target site. When the stent or lattice structures are covered with a fabric or polymeric membrane covering, they are commonly referred to as grafts. Grafts may be used for the treatment of aneurysms or other conditions which require placement of a non-permeable or semi-permeable barrier at the treatment site. The terms "prosthesis" and "prostheses" refer broadly to all radially expansible stents, grafts, and other scaffold-like structures which are intended for deployment within body lumens.

The stents and prostheses of the present invention may have any of a variety of common constructions, including helical structures, counterwound helical structures, expandable diamond structures, serpentine structures, or the like. Such conventional stent structures are well described in the patent and medical literature. Specific examples of suitable stent structures are described in the following U.S. patents, the full disclosures of which are incorporated herein by reference: U.S. Pat. Nos. 6,315,794; 5,980,552; 5,836,964; 5,527,354; 5,421,955; 4,886,062; and 4,776,337, the full disclosures of which are incorporated herein by reference. Preferred structures are described herein with reference to FIGS. 4 and 5.

According to the present invention, the stents which are deployed may have a length of 1 mm or greater, usually 2 mm or greater, and typically of 3 mm or greater, usually being in the range from 1 mm to 100 mm, typically from 2 mm to 50 mm, more typically from 2 mm to 25 mm, and usually from 3 mm to 20 mm. The use of such short stent lengths is advantageous since multiple stents are to be employed.

The methods and apparatus of the present invention will provide for the deployment of a plurality of stents or other prostheses, usually including at least two stents, from a common stent delivery catheter. Usually, the number of delivered stents will be in the range from 2 to 50, typically from 3 to 30, and most typically from 5 to 25. As more stents are placed on the delivery catheter, the individual stent length will often be somewhat less, although this is not necessarily the case in all instances. The multiple prostheses may be deployed individually or in groups of two or more at single or multiple spaced-apart locations in the body lumen or lumens.

In a first aspect of the present invention, a method for stenting an extending length of a body lumen comprises introducing a catheter carrying a plurality of, usually at least two, discrete stents to the body lumen. Usually, the introduction is percutaneous and, in the case of intravascular delivery, uses a conventional introduction technique, such as the Seldinger technique. After reaching a target location, at least a first stent is released from the catheter at that first location. The catheter is then repositioned to a second location, and at least a second stent is released from the catheter at the second location. The catheter is then repositioned to a third location, and at least a third stent is released from the catheter at the third location In addition to deploying stents and other prostheses at spaced-apart locations within a blood vessel or other body lumen, the methods and apparatus in the present invention can be used for delivering one, two, three, or more discrete stents or other prosthesis segments contiguously at a single location within the body lumen. In this way, the length of the prosthesis which is implanted can be selected and modified to accommodate the length of the vessel to be treated. It will be appreciated that with systems which carry 10, 20, 30 or more quite short prostheses or prosthesis segments, the length of the lumen being treated can be tailored very closely from very short to very long with the selectable intervals depending on the length of the prosthesis or prosthesis segment.

The deployment steps can, of course, be repeated a sufficient number of times so that all or at least more of the stents carried by the delivery catheter are delivered to and deployed within the body lumen. A particular advantage of this delivery method is that the discrete stents may be distributed along extended lengths of the body lumen, typically in the range from 1 cm to 2 cm, often in the range from 1 cm to 5 cm, and in many instances even longer. Additionally, the stents may be delivered so as to avoid side branches or other regions where placement of the stent is undesirable. Moreover, with the use of drug-coated stents, it may be possible to place the stents apart by discrete distances, typically from one-half to one millimeter (mm), while still achieving vessel patency and hyperplasia inhibition.

Releasing of the stents from the catheter may be achieved using a balloon to cause balloon expansion of the stent. Alternatively, release of the stent may be achieved by radially constraining an elastic or self-expanding stent within a lumen of the delivery catheter and selectively advancing the stent from the catheter and/or retracting the catheter from over the stent. In one embodiment, a sheath over the stents includes a valve member, or "stent valve," which allows stents to be separated so that a balloon can more accurately inflate deployed stents while other stents remain within the sheath.

In preferred embodiments, the stents are coated with at least one agent, such as an agent which inhibits hyperplasia. The agent may be biologically active or inert. Particular biologically active agents include anti-neoplastic drugs such as paclitaxel, methotrexate, and batimastal; antibiotics such as doxycycline, tetracycline, rapamycin, and actinomycin; immunosuppressant such as dexamethosone, methyl prednisolone, nitric oxide sources such as nitroprussides; estrogen; estradiols; and the like. Biologically inert agents include polyethylene glycol (PEG), collagen, polyglycolic acids (PGA), ceramic material, titanium, gold and the like.

In another aspect, the present invention comprises catheters and apparatus for stenting extended lengths of a body lumen, particularly a blood vessel. The catheters comprise a catheter body having a proximal end and a distal end. At least two discrete stents are carried at or near a distal end of the catheter body. By "discrete," it is meant that the stents are unconnected and can be deployed from the catheter in an unattached manner. (The delivery of attached prostheses is described below.) Deployment of such discrete stents permits the individual stents to be placed at spaced-apart target locations or immediately adjacently within the blood vessel or other body lumen. The catheters further comprise deployment means for deploying the individual stents from the catheter body. For example, the deployment means may comprise one or more balloons for placement and radial expansion of the stents. Alternatively, the deployment means may comprise a pusher or other device for advancing self-expanding stents from the distal end of the catheter body and/or a sheath for selectively retracting over the stents to permit self-expansion. In exemplary embodiments, the catheters will carry at least two discrete stents, at least five discrete stents, and as many as 10 discrete stents, or in some cases, as many as 30 or more discrete stents.

In a particular embodiment, the catheter comprises a single balloon which is reciprocatively mounted within the catheter body and adapted for receiving individual stents thereover. A pusher or other device for successively and controllably loading individual or multiple stents over the balloon is also provided. In this way, the catheter may carry multiple stents and employ the single balloon for positioning and expansion of the stents.

In further embodiments, the stents of the present invention are composed at least partly of a bioabsorbable material, such as polyethylene glycol (PEG), collagen, gelatin, polyglycolic acids (PGA), polylactic acids (PLA), and the like. Optionally, one or more bioactive substances are dispersed in the bioabsorbable material such that the bioactive substance will be released over time as the bioabsorbable material degrades. In a particular embodiment, the bioabsorbable material is formed on or within a scaffold composed on a non-bioabsorbable material, typically stainless steel, Nitinol™, or other conventional stent metal material. Other materials, such as gold (e.g., pure or nearly pure gold), platinum, or the like, may also be used.

In a further aspect of the present invention, a catheter for delivering a plurality of expansible prostheses to a body lumen comprises a catheter body, a sheath, and a plurality of radially expansible prostheses. The catheter body has a proximal end and a distal end, and the sheath is coaxially disposed over the catheter body with the prostheses positionable in an annular space between the inside of the sheath and the exterior of the catheter body. The sheath is preferably retractable relative to the catheter body so that the prostheses may be advanced beyond a distal end of the sheath. Usually, the catheter will further comprise a pusher tube disposed coaxially over the catheter body and within an interior lumen of the sheath. A distal end of the pusher tube will engage a proximal end of the proximal-most prosthesis so that the pusher tube can be distally advanced relative to the sheath to selectively push or deploy individual prostheses from the sheath. Often, such deployment is achieved by holding the pusher tube and prostheses substantially stationary relative to the body lumen while the sheath is retracted proximally to release or deploy the prostheses.

Usually, at least a distal portion of the sheath will have a greater column strength than that of a distal portion of the catheter body. Additionally or alternatively, the pusher tube may also have a greater column strength than a distal portion of a catheter body. By providing column strength in the outer most portion of the catheter, i.e., the sheath, and optionally the pusher tube, the overall column strength of the catheter can be increased with a minimum increase in its diameter or profile. It will be appreciated that low profile catheters are highly advantageous for accessing remote regions of the vasculature, particularly the small coronary and cerebral arteries. Using the preferred constructions of the present invention, catheters having diameters 2 mm or less, and in some instances as low as 1 mm or less, can be achieved. The constructions will, of course, also be suitable for larger diameter catheters for use in the peripheral and other larger blood vessels.

The catheter of the present invention will preferably carry at least two prostheses, more preferably carrying at least three prostheses, and often carrying a greater number of prostheses as set forth above in connection with other embodiments. The prostheses will typically be arranged in an end-to-end manner either with or without a physical linkage therebetween. The physical linkage may comprise a frangible component which must be mechanically broken or alternatively may comprise a pair of coupling elements which fit together and which may be separated without any material breakage. Frangible coupling elements will usually comprise a strut, bar, spring, or similar connecting link and will optionally be scored, notched, or otherwise adapted to break along a particular line when a suitable mechanical force is applied. Exemplary separable coupling elements include male and female elements, such as a rod and tube which may be axially separated, a tab and receptacle which may be radially separated, and the like.

In a specific embodiment of the catheter, the catheter body may comprise an expansion element, such as an inflatable balloon, near its distal end. The expansion element will be positionable distal to the retractable sheath so that it can be used to regularly expand one or more of the prostheses. For example, the inflatable balloon may carry multiple prostheses on its outer surface so that sheath retraction can expose one, two, three, or more of the prostheses. The remaining prostheses will continue to be covered by the sheath. When inflating the balloon, however, only that portion of the balloon and those prostheses carried on the exposed portion of the balloon will be inflated. The remaining (proximal) portion of the balloon will continue to be constrained by the sheath so that neither the balloon nor the prostheses covered by the sheath will be expanded. In this way, any preselected number of the individual prostheses may be expanded at one time, while the remaining prostheses are protected and unexpanded, remaining available for subsequent expansion using the balloon.

Alternatively or in addition to the balloon, the catheter body may comprise a heater for selectively heating prostheses which have been advanced distally beyond the sheath. For example, the catheter body may have a lumen for delivering a heated medium, such as heated saline, intravascularly to heat and expand stents or other prostheses formed from suitable heat memory alloys (as described in more detail below). Alternatively, a separate exterior guide catheter or other tube may be used for delivering such a heated medium to effect expansion of the prostheses. As a third alternative, a powered heating element, such as a radio frequency heater, electrical resistance heater, or laser-heated element, may be provided on the catheter body for directly heating the exposed prostheses.

For the delivery of individual prostheses or stents which are joined by frangible or breakable links, as discussed above, it will often be desirable to provide a shearing mechanism on the catheter. The shearing mechanism will usually be mechanical, but could also be electrolytic, ultrasonic, or chemical. In the exemplary embodiments, the shearing mechanism comprises a first shearing element on a distal region of the catheter body and a second or mating shearing element on a distal region of the sheath. The prostheses may be advanced from the sheath while the shearing mechanism on the catheter body is distally advanced (leaving a space or opening for prosthesis deployment). After a desired number of prostheses have been deployed, the catheter body may be retracted relative to the sheath in order to close the shearing elements to sever the link(s) between the advanced prostheses and those prostheses which remain within the sheath. In other cases, the shearing mechanism could be an electrode for inducing electrolytic breakage of the link, an ultrasonic transducer for mechanically degrading a susceptible link (i.e. a link having a resonant frequency which corresponds to the ultrasonic transducer), a luminal port for releasing a chemical agent selected to chemically degrade the link, or the like.

In a further alternative embodiment, a catheter constructed in accordance with the principles of the present invention comprises a pusher tube, a plurality of radially expansible prostheses arranged end-to-end and extending distally of the distal end of the pusher tube, and a sheath disposed coaxially over the pusher tube and the prostheses. Optionally, but not necessarily, this embodiment will include a catheter body disposed coaxially within the pusher tube and prostheses. By retracting the sheath proximally relative to the pusher tube, individual ones or groups of the prostheses will be exposed and deployed. The catheter body may be used in any of the ways described previously in order to effect or control deployment of the prostheses. Optionally, the pusher tube, the sheath, or both, may have a greater column strength than the catheter body when the catheter body is employed.

The present invention further provides methods for stenting extended lengths of the body lumen, where the methods comprise introducing a catheter carrying a plurality of radially expansible prostheses to a target site within the body lumen. The prostheses are arranged end-to-end and are covered by a sheath. The prostheses are then deployed by retracting the sheath relative to the prostheses by a first preselected distance to uncover a first predetermined number of the prostheses. After retraction of the sheath, a first predetermined number of prostheses, which may be anywhere from one up to the entire number of prostheses being carried, are radially expanded at the target site within the target site of the body lumen.

Prosthesis expansion may be achieved in a variety of ways. In a first instance, the prostheses are expanded by inflating a balloon within the particular prosthesis to be expanded. For example, a single balloon may be disposed under all the prostheses, with the sheath retracted to expose only those prostheses to be deployed. When the balloon is expanded, the balloon will expand the exposed prostheses, with expansion of the prostheses which remain covered being restrained by the sheath. By further retracting the sheath, the previously undeployed prostheses may then be deployed. Optionally, the prostheses are advanced (or at least axially restrained relative to the sheath) by a pusher tube which engages a proximal end of the proximal-most prosthesis.

As an alternative to balloon expansion, the uncovered prostheses may be expanded by exposure to heat. The heat may be applied by directing a heated medium to the prostheses, directing electrical energy through the prostheses, and/or energizing a heating element positioned adjacent to the uncovered prostheses.

In preferred aspects of the methods of the present invention, the body lumen will be a blood vessel, preferably a coronary artery, a cerebral artery, or other small artery. The prostheses will preferably be coated with biologically active or inert agent, such as an agent selected to inhibit hyperplasia, more specifically being any of the particular agents set forth hereinabove.

The invention further provides prosthesis delivery catheters and systems that include valve members to enable the selective deployment of a desired number of prostheses at a treatment site while retaining other prostheses within the device for deployment at other locations. In general, these catheters and systems will include a sheath having a proximal end, a distal end, an opening at the distal end, and a passage in communication with the opening adapted to contain a plurality of prostheses. A valve member is disposed near the distal end of the sheath adapted for selectively retaining at least one prosthesis within the passage.

The valve member may function either actively or passively. In passive configurations, the valve member prevents the prosthesis from exiting the passage under a first force and allows the prosthesis to exit the passage under a second force higher than the first force. In those embodiments for delivering balloon-expandable stents, an expandable member is slidably positioned in the sheath and the prostheses are positionable on the expandable member. Typically, the expandable member is an inflatable balloon mounted to an elongated catheter shaft. A pusher is preferably slidably mounted in the sheath and is adapted to exert a force on the prostheses to advance them distally through the sheath. In preferred embodiments, the valve member will be adapted to prevent the prostheses from being advanced out of the sheath unless sufficient force is exerted on the pusher. The distal movement of the expandable member relative to the prostheses in the sheath will not itself be sufficient to advance the prostheses past the valve member unless the pusher is also pushed against the prostheses. In this way, the desired number of prostheses can be advanced out of the sheath by pushing both the expandable member and the pusher together while holding the sheath in position (or by pulling the sheath back while maintaining the expandable member and the pusher in position). The expandable member and the prostheses to be deployed can then be advanced further relative to the sheath a desired distance without causing additional prostheses to move out of the sheath.

It should be understood that the movements of the sheath, expandable member, pusher tube and prostheses are relative and in most embodiments of the invention, either retracting the sheath proximally relative to the expandable member and pusher tube, or advancing the expandable member and pusher tube distally relative to the sheath, or a combination thereof, may be practiced without departing from the principles of the invention. Therefore, when the movement of one component relative to another component is described herein, it should be interpreted to mean holding one component in position while moving the other, or vice versa, or moving both components relative to each other.

The invention includes various exemplary embodiments of passive valve members. The valve member may comprise one or more pairs of lobes on opposing sides of the passage in the sheath and extending inwardly to engage the prostheses therein. Alternatively, one or more annular or helical ribs may be disposed on the inner wall of the sheath with an inner diameter suitable for engaging the prostheses in the passage. The invention further provides tubular valve elements, both straight and tapered, as well as valve members having a plurality of inwardly-extending projections such as bristles and flexible shafts. In alternative embodiments, the valve member may comprise a diaphragm, duckbill, or other deflectable structure, or may be a magnetic or suction-based mechanism. Multistage valves including pluralities and combinations of these elements axially spaced along the sheath are also provided.

In active embodiments, the valve member is selectively movable between a contracted configuration in which the valve member allows movement of prostheses out of the sheath, and an extended configuration in which the valve member inhibits movement of prostheses out of the sheath. In these embodiments, the valve member may comprise an inflatable member that can be selectively inflated and deflated, a movable pawl that can be extended into and retracted from the passage in the sheath, a hydraulic piston, or a heat-activated shape memory alloy wire that changes shape in response to temperature change. Further, an active valve member may comprise an enlarged portion of the sheath that has a larger outer diameter than the remainder of the sheath, wherein a tubular member is slidably disposed over the sheath and can be moved over the enlarged portion to urge the sheath into engagement with the prostheses.

The active valve member may alternatively comprise a switch having two engagement elements each movable between retracted and extended positions. The first engagement element is axially spaced apart from the second engagement element by a distance of at least about the length of one of the prostheses. The switch has two states: In one state, the first engagement element is in a retracted position and the second engagement element is in an extended position. In the second state, the first engagement element is in an extended position and the second engagement element is in a retracted position. Usually, the first engagement element is near the distal end of the sheath and the second engagement element is spaced proximally about the length of one prosthesis from the first engagement element. In this way, with the first engagement element retracted, the distal-most prosthesis can be deployed from the sheath while the second engagement element retains the remaining prostheses in the sheath. The switch can then be moved to its second state, wherein the second engagement element allows the prostheses to advance to the distal end of the sheath while the first engagement element prevents them from being deployed beyond the distal end.

In a further embodiment, the delivery catheters and systems of the invention include shuttle members for advancing selected numbers of prostheses a selected distance relative to the sheath. The shuttle member may comprise a tubular member slidably mounted over the sheath, the tubular member having an engagement element near its distal end extending inwardly to engage at least one prosthesis distally of the sheath. The shuttle member may alternatively comprise a pusher element slidably disposed within the sheath, the pusher element being configured to engage at least one of the prostheses. In one embodiment, the pusher element has an inner member slidably mounted to an outer member disposed in the sheath proximal to the plurality of prostheses. Preferably, the outer member is movable a preselected limited distance relative to the inner member, usually at least about the length of one of the prostheses. In another embodiment, the pusher element is disposed laterally of the prostheses and has a plurality of engagement elements that extend inwardly into the passage to engage the prostheses. The engagement elements are preferably axially spaced apart a distance of at least about the length of one of the prostheses. The pusher member is movable proximally relative to a selected number of prostheses in the sheath, and the pusher member is movable distally to advance the selected number of prostheses relative to the sheath. In this embodiment, the sheath will usually include engagement structures for maintaining the position of the prostheses as the pusher member moves proximally. The pusher member is configured to advance the selected number of prostheses distally of the valve member in the sheath.

The catheters of the present invention will comprise a number of coaxial components, such as sheaths, pusher tubes, catheter bodies, and the like. While it will often be described that stents or other prostheses are advanced distally from the sheath, such description will apply to sheaths which are retracted proximally relative to the prostheses to effect the release. Thus, all descriptions of direction are meant to be relative.

BRIEF DESCRIPTION OF THE DRAWINGS

FIGS. 8A-8C illustrate a catheter and its use for delivering self-expanding prostheses according to the methods of the present invention.

FIGS. 9A and 9C illustrate an alternative catheter construction intended for delivering self-expanding prostheses according to the methods of the present invention.

FIGS. 10A-10C illustrates use of the catheter for delivering prostheses by a heat-induction method in accordance with the principles of the present invention.

FIGS. 12A-12D illustrate a catheter for delivering multiple prostheses using balloon expansion in accordance with the methods of the present invention.

FIGS. 13A-13D illustrate a catheter including a stent valve for delivering multiple prostheses using balloon expansion in accordance with the methods of the present invention.

FIGS. 15A-15B are side cross-sections and transverse cross-sections, respectively, of a valve member in a delivery catheter according to the invention.

FIGS. 16A-16B are side cross-sections and transverse cross-sections, respectively, of a further embodiment of a valve member in a delivery catheter according to the invention.

FIGS. 17A-17B are side cross-sections and transverse cross-sections, respectively, of a further embodiment of a valve member in a delivery catheter according to the invention.

FIGS. 18A-18B are side cross-sections and transverse cross-sections, respectively, of a further embodiment of a valve member in a delivery catheter according to the invention.

FIGS. 19A-19B are side cross-sections and transverse cross-sections, respectively, of a further embodiment of a valve member in a delivery catheter according to the invention.

FIGS. 20A-20B are side cross-sections and transverse cross-sections, respectively, of a further embodiment of a valve member in a delivery catheter according to the invention.

FIGS. 21A-21B are side cross-sections and transverse cross-sections, respectively, of a further embodiment of a valve member in a delivery catheter according to the invention.

FIGS. 22A-22B are side cross-sections and transverse cross-sections, respectively, of a further embodiment of a valve member in a delivery catheter according to the invention.

FIGS. 23A-23B are side cross-sections and transverse cross-sections, respectively, of a further embodiment of a valve member in a delivery catheter according to the invention.

FIG. 23C is a side cross-section of the catheter and valve member of FIGS. 23A-23B with alternative prostheses therein.

FIG. 24A is a perspective cut-away view, FIG. 24B is a transverse cross-section, and FIG. 24C is a side cross-section of a further embodiment of a valve member in a delivery catheter according to the invention.

FIG. 24D is a close-up view of the valve member of FIGS. 24A-C.

FIG. 25A is a perspective view and FIG. 25B is a side cross-section of a further embodiment of a valve member in a delivery catheter according to the invention.

FIG. 26 is a perspective view of a further embodiment of a valve member in a delivery catheter according to the invention.

FIGS. 27A-27B are side cross-sections of two alternative embodiments of a valve member in a delivery catheter according to the invention.

FIGS. 28A-28B are side cross-sections of two alternative embodiments of a valve member in a delivery catheter according to the invention.

FIG. 29 is a side cross-section of a further embodiment of a valve member in a delivery catheter according to the invention.

FIGS. 30A-30B are side cross-sections and transverse cross-sections, respectively, of a further embodiment of a valve member in a delivery catheter according to the invention.

FIG. 31 is a side cross-section of a further embodiment of a valve member in a delivery catheter according to the invention.

FIGS. 32-33 are a side cross-sections of two further embodiments of a valve member in a delivery catheter according to the invention.

FIG. 34A is a side cross-section of a further embodiment of a valve member in a delivery catheter according to the invention. FIG. 34B is a side close-up view of the valve member of FIG. 34A.

FIG. 35 is a side cross-sections of two further embodiments of a valve member in a delivery catheter according to the invention.

FIGS. 36A-36B are side cross-sections, of a further embodiment of a valve member in a delivery catheter according to the invention.

FIG. 37A is a side cross-section of a further embodiment of a valve member in a delivery catheter according to the invention. FIG. 37B is a perspective cut-away view of the valve member of FIG. 37A.

FIGS. 38-42 are side cross-sections of additional embodiments of a valve member in a delivery catheter according to the invention.

FIGS. 43A-43B are side-cross-sections of valve and shuttle members in a delivery catheter according to the invention in two different positions.

FIGS. 45A-45E are side cross-sections of a further embodiment of valve and shuttle members in a delivery catheter according to the invention in various positions.

DETAILED DESCRIPTION OF THE SPECIFIC EMBODIMENTS

Figure 1:
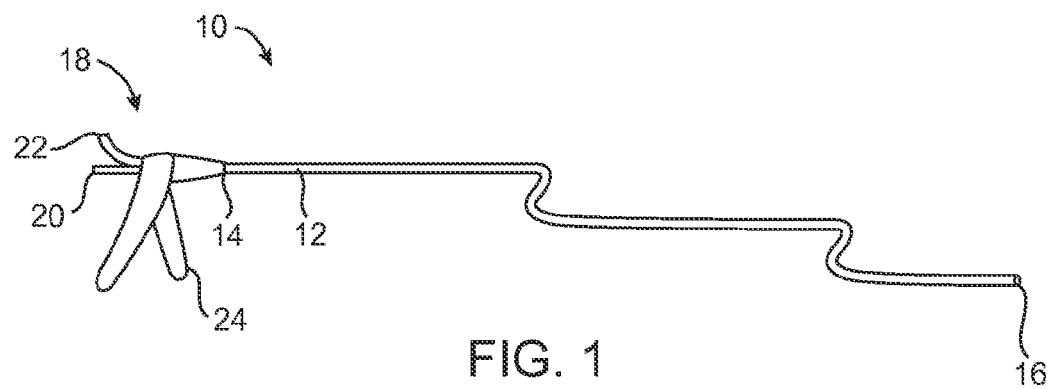
FIG. 1 is a perspective view illustrating a stent delivery catheter constructed in accordance with the principles of the present invention.

Referring now to FIG. 1, the stent delivery catheter 10 comprises a catheter body 12 having a proximal end 14 and a distal end 16. The catheter body is formed from a conventional catheter material, such as braided or coiled stainless steel, a natural or synthetic polymer, including silicone rubber, polyethylene, polyvinylchloride, polyurethane, polyester, polytetrafluoroethylene, nylon, and the like. The body may be formed as a composite having one or more reinforcement layers incorporated within a polymeric shell in order to enhance strength, flexibility, and toughness. For intravascular use, the catheter body will typically have a length in the range from 40 cm to 150 cm, usually being between 40 cm and 120 cm for peripheral blood vessels and between 110 cm and 150 cm for coronary arteries. The outer diameter of the catheter body may vary depending on the intended use, typically being between 3 French and 15 French, usually from 5 French to 9 French.

Figure 2:
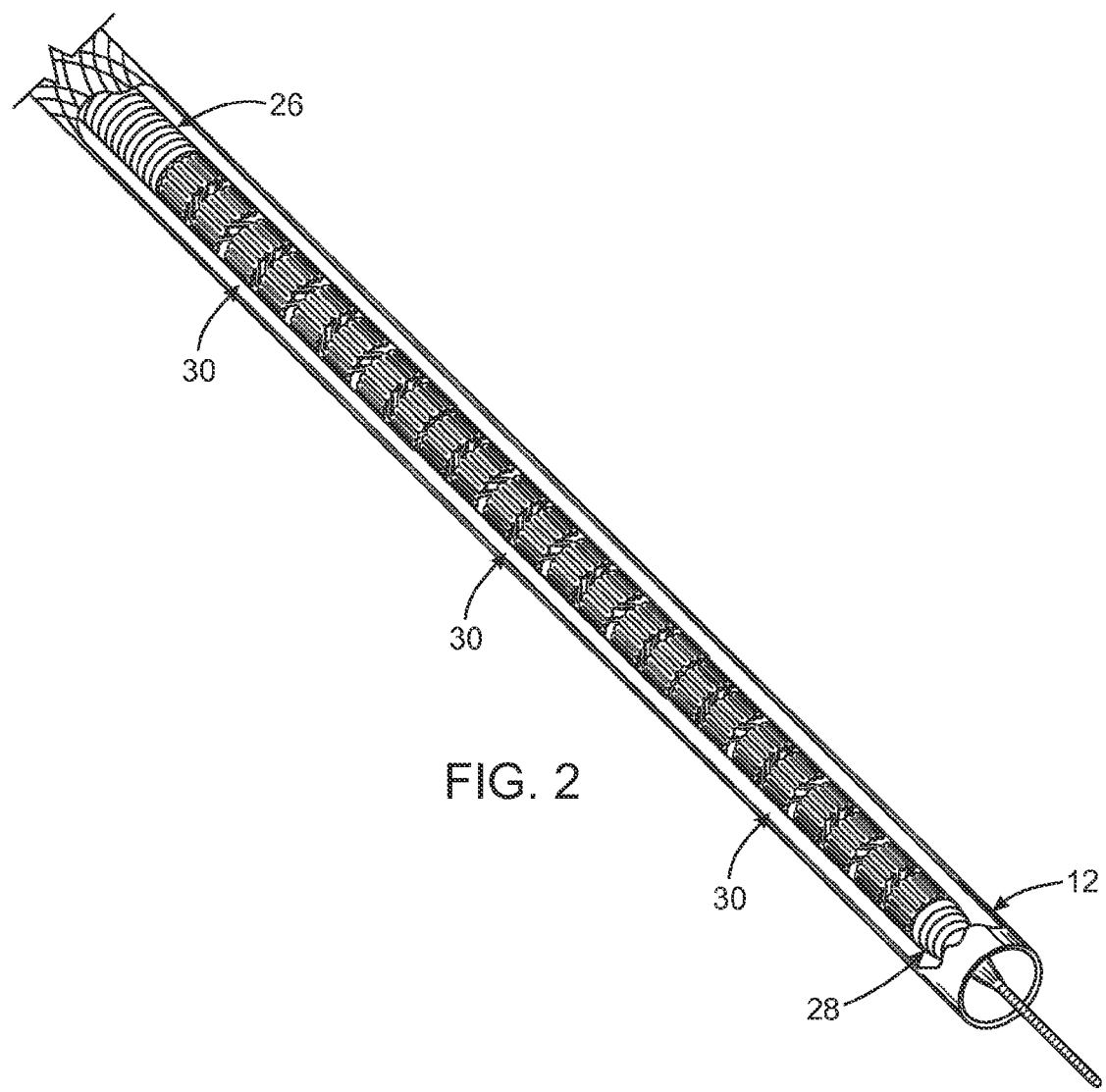
FIG. 2 is a detailed view of the distal end of the catheter of FIG. 1 with portions broken away.

Catheter 10 will include a handle 18 at its proximal end 14. The handle may include a guidewire port 20 and a balloon inflation port 22, as well as a handle grip 24 which advances a pusher shaft whose distal end 26 is shown in FIG. 2. Additionally, the handle permits reciprocation of a catheter delivery balloon 28, also shown in FIG. 2.

A plurality of stents 30 are carried in a lumen of the catheter body 12, as shown in FIG. 2. While three stents 30 are shown, it will be appreciated that additional stents may be carried generally within the ranges disclosed above. The illustrated stents comprise a plurality of serpentine ring structures joined by offset struts. It will be appreciated, however, that a wide variety of stent structures could be carried by the catheter 10, generally as described above.

Figure 3A:
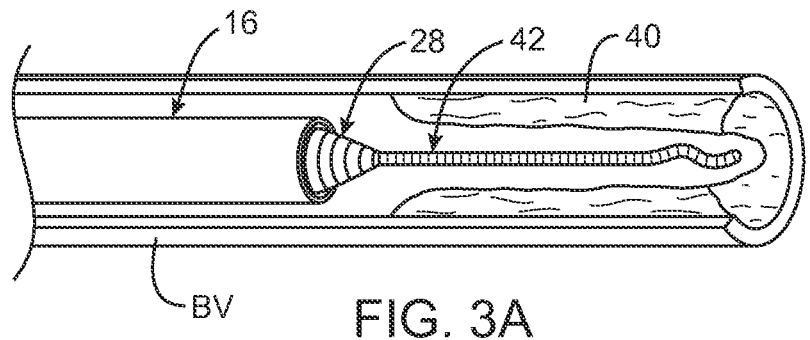
FIGS. 3A-3F illustrate use of the catheter of FIG. 1 for deploying a plurality of stents using balloon expansion.
Figure 3B:
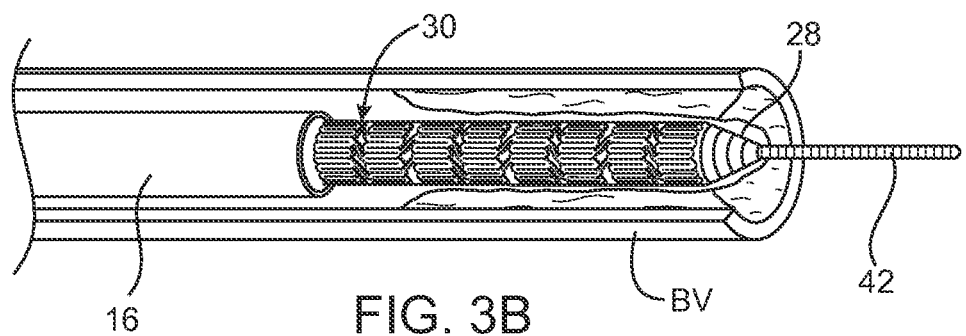
Figure 3C:
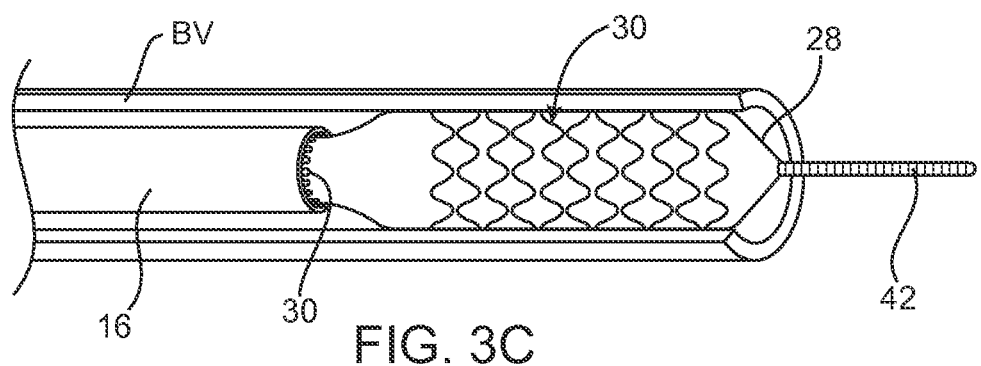

Referring now to FIGS. 3A-3F, the distal end 16 of the catheter 10 is advanced to target location 40 within a diseased blood vessel (BV) over a guidewire 42, as illustrated in FIG. 3B. Balloon 28 carries a first of the three stents 30, and is advanced distally from the catheter to deploy the stent within the treatment region 40, as illustrated in FIG. 3B (optionally by retracting the catheter body 12 proximally relative to balloon 28). Once the stent 30 is properly located, the balloon 28 is inflated to deploy the stent (and optionally dilate the treatment region), as illustrated in FIG. 3C.

Figure 3D:
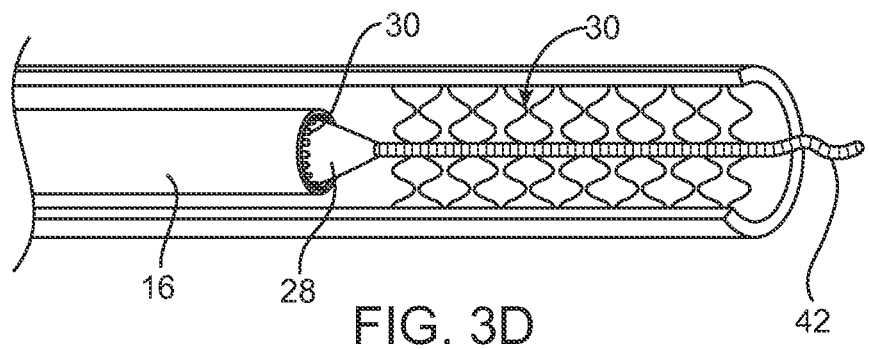
Figure 3E:
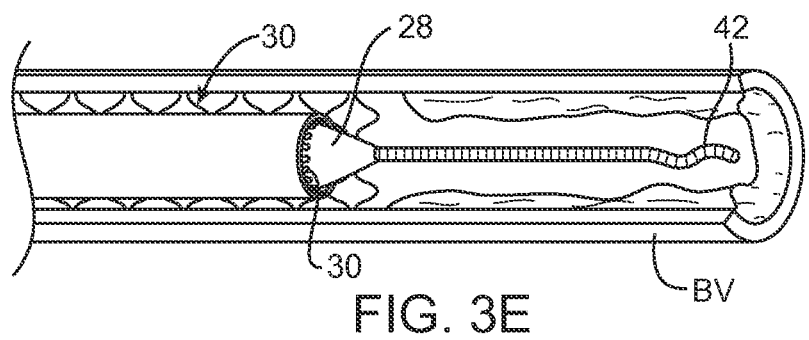
Figure 3F:
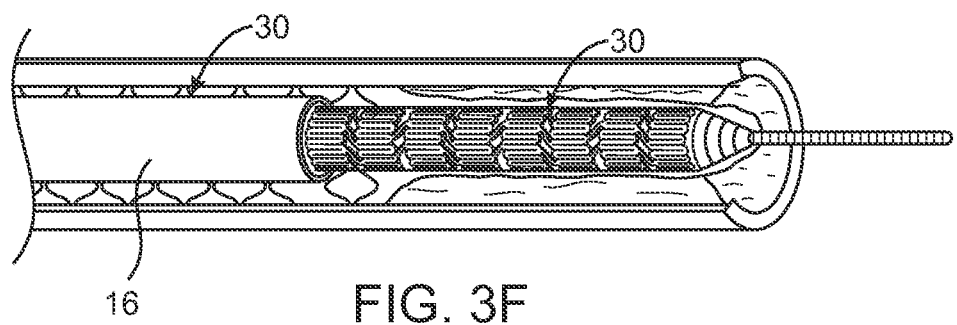

The balloon is then deflated, and retracted back into the distal end of the catheter 16, as illustrated in FIG. 3D. The expanded stent is left in place. The balloon 28 is retracted back to within the second stent 30, as illustrated in FIG. 3E. The second stent has been advanced using the pusher 26 so that it is properly located over the balloon 28, and the distal end of the catheter 16 may then be advanced so that the second stent 30 is located within a second treatment region spaced apart from the first treatment region. As illustrated in FIG. 3F, the treatment regions are adjacent to each other. It will be appreciated, however, that the second treatment region could be spaced a substantial distance from the first treatment region. Deployment of the second stent 30 is then completed in the same manner as described above for the first stent. Similarly, deployment of third, fourth, fifth, and additional stents 30 may be effected in the same manner. In this way, it will be appreciated that relatively lengthy and/or disseminated regions within a blood vessel may be treated.

Figure 4:
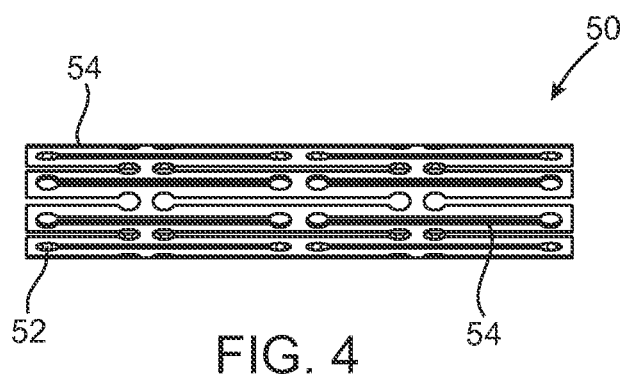
FIG. 4 illustrates an exemplary prosthesis constructed in accordance with the principles of the present invention.

Referring now to FIG. 4, an exemplary prosthesis 50 constructed in accordance with the principles of the present invention is illustrated. The prosthesis has a tubular body 52 having a plurality of axial slots 54, typically formed by laser cutting or chemical etching a tubular stock, such as stainless steel or nickel-titanium hypotube. Prosthesis 50, which may be delivered in groups of two, three, four, or more in accordance with the principles of the present invention, will have a length within the ranges set forth above. The diameter, prior to expansion, will typically be below 2 mm, preferably being below 1 mm, although in some instances much larger diameters can be used. The diameter of the prosthesis 50 upon expansion, of course, will be much greater, typically being at least twice as large, sometimes being at least three times as large, or even larger.

Figure 5A:
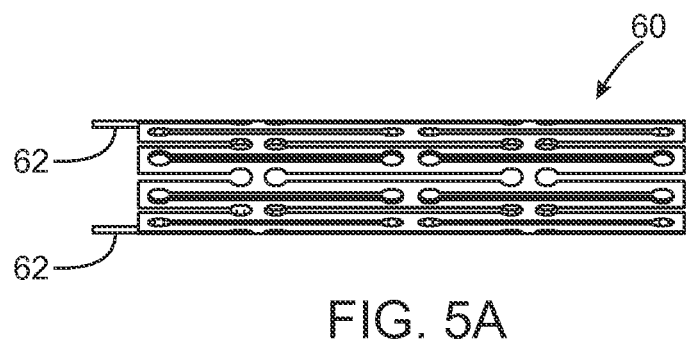
FIGS. 5A and 5B illustrate a prosthesis similar to that shown in FIG. 4, but further including coupling elements for permitting detachable coupling of adjacent prostheses.
Figure 5B:
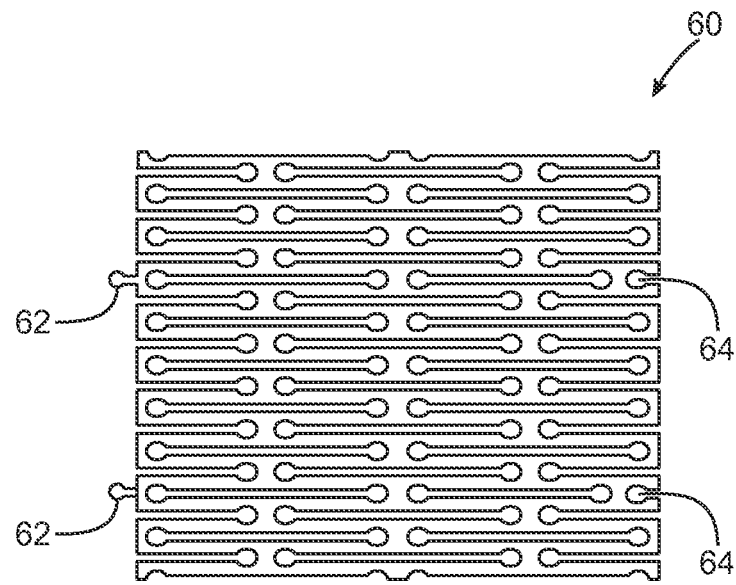

Referring now to FIGS. 5A and 5B, a prosthesis 60, similar to prosthesis 50, includes a pair of coupling elements 62 which are received in mating slots 64. FIG. 5B is a "rolled-out" view of the "rolled-out" view of the prosthesis 60 for better illustrating the coupling element 62 and slots 64 of the prosthesis 60.

Figure 5C:
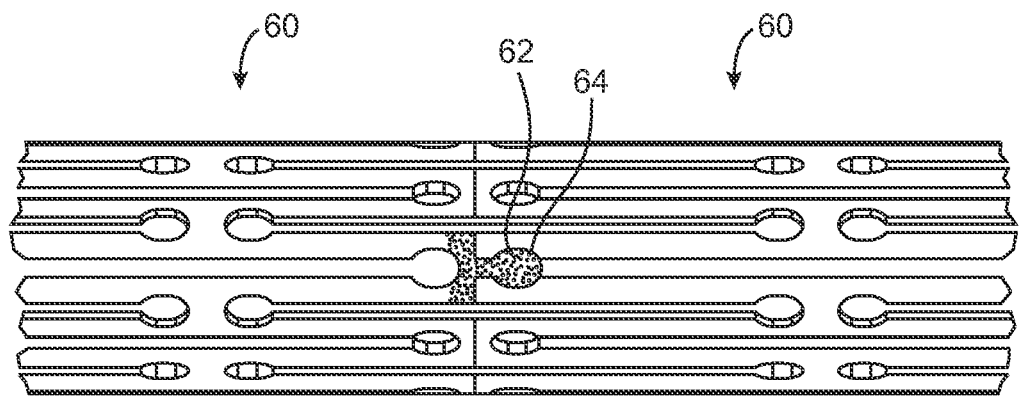
FIG. 5C illustrates a pair of prostheses, as shown in FIG. 5A and FIG. 5B, joined together by the coupling elements.

As shown in FIG. 5C, pairs of prosthesis 60 may be joined or coupled by circumferentially aligning the coupling element 62 with the slot 64. Although only a single coupling element 62 and slot 64 is visible in FIG. 5C, it will be appreciated that the second coupling element and slot will be located on the opposite side of the illustrated pair of prostheses.

Figure 5D:
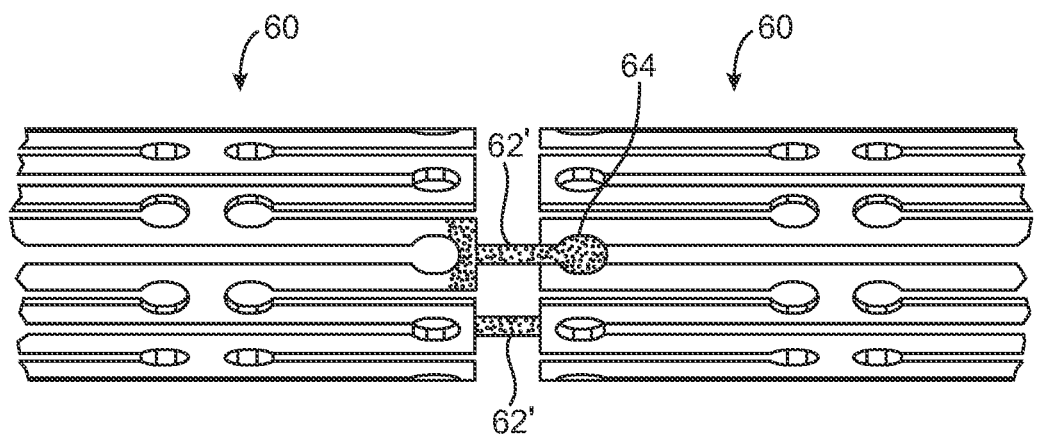
FIG. 5D illustrates a pair of adjacent prostheses coupled by a modified coupling element.

In FIG. 5C, the two prosthesis 60 are abutted directly against each other. Such a configuration is advantageous in that it provides for a substantially continuous stent or graft structure when the pair is expanded together in a body lumen. The structure, however, is disadvantageous in that it does not provide for flexibility at the point where the two prostheses meet. In order to provide for greater flexibility, as shown in FIG. 5D, a coupling element 62' can have an elongated shank to provide for a desired offset, typically in the range from 0.05 mm to 1 mm, preferably from 0.1 mm to 0.5 mm.

Figure 5E:
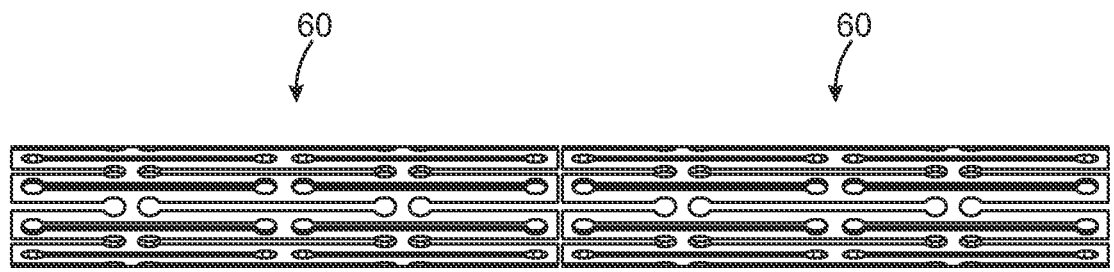
FIGS. 5E and 5F illustrate radial separation of the adjacent prostheses of FIG. 5C.
Figure 5F:
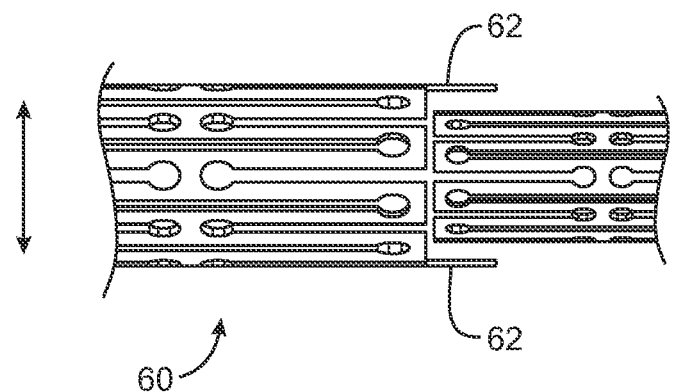

Referring now to FIGS. 5E and 5F, axial separation of the prostheses 60 is achieved by differential radial expansion of at least one of the prostheses. For example, when both prostheses 60 are in their unexpanded configurations, as shown in FIG. 5E, the coupling elements 62 are constrained by the slots 64, as previously described. By radially expanding the left-hand prostheses 60, as shown in FIG. 5F, the coupling elements 62 will be moved radially outwardly from the slots so that the two prostheses are no longer axially linked. It will be appreciated, however, that the two prostheses 60 may be radially expanded together (as described in more detail hereinafter) in a manner which preserves the link created by the coupling elements 62 and slots 64 so that combinations of two, three, four, or more prostheses may be delivered simultaneously and, in effect, provide a continuous prosthesis having a length which is some multiple of the length of each individual prostheses 60. The combined prostheses may then be separated from any additional prostheses (which remain in a delivery catheter as described below) by the radial expansion of those prostheses which are to be deployed. In this way, stents, grafts, or other prostheses may be delivered to the body lumen in both different lengths (by properly selecting the number of individual prostheses 60) and at different locations (by releasing individual or multiple prostheses 60 at different portions of the body lumen).

Figure 6A:
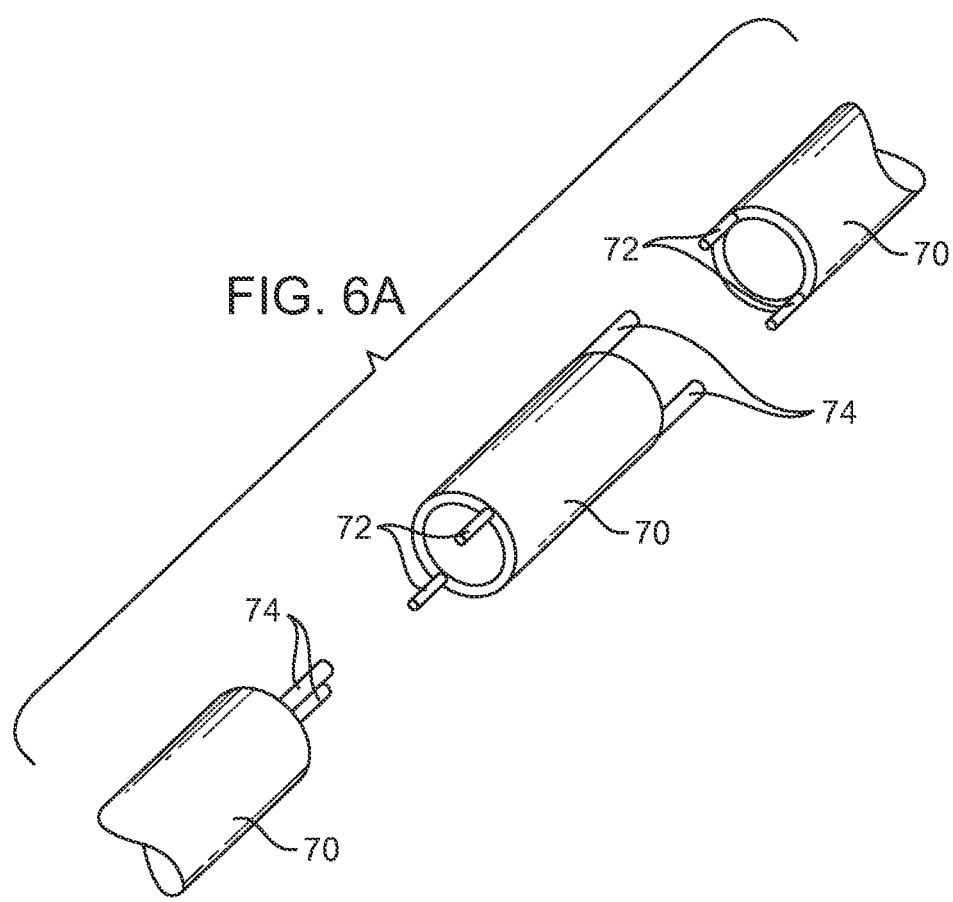
FIGS. 6A and 6B illustrate a second coupling mechanism constructed in accordance with the principles of the present invention.
Figure 6B:
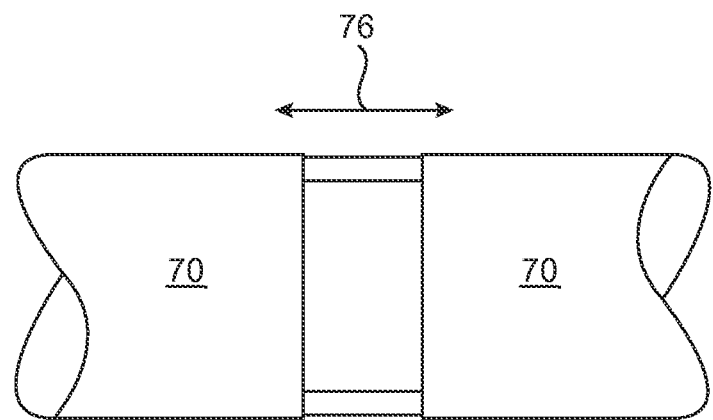

Axially separable coupling elements may also be provided, as illustrated in FIGS. 6A and 6B. Each prosthesis 70 includes a pair of male coupling elements 72 at one end and a pair of female coupling elements 74 at the other end. The male coupling elements 72 are typically short rods which extend axially from the periphery of the prosthesis end and the female coupling elements are typically short tubes having hollow interiors which detachably receive the male coupling elements. Thus, the prostheses 70 may be joined in an end-to-end manner, as shown in FIG. 6B. The prostheses are separated by pulling them in an axial direction, as shown by arrow 76, but will remain linked under axial compression as well as when exposed to a substantial bending moment. Thus, the axially separable coupling structures of FIGS. 6A and 6B are advantageous in that they remain linked during deployment of the prostheses 70, even when deployment involves significant bending and radial stress. Separation may be effected by pullback on the delivery catheter in order to disengage the coupling elements 72 and 74.

Figure 7:
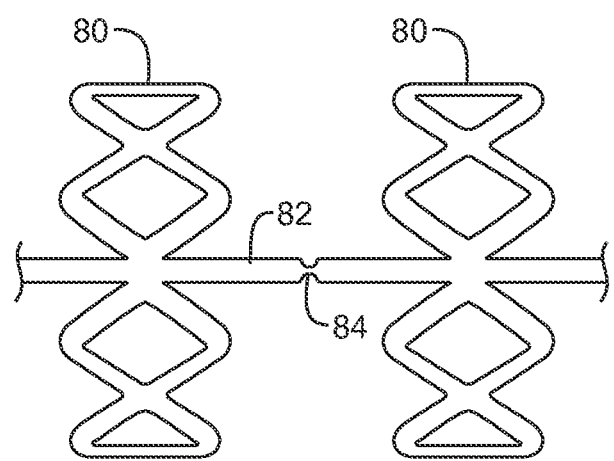
FIG. 7 illustrates a frangible linkage for joining a pair of adjacent prostheses.

A third approach for detachably coupling adjacent prostheses 80 is illustrated in FIG. 7. Each prosthesis 80 comprises an expansible ring of diamond-shaped members. Other conventional stent or prostheses structures, however, could also be used. The adjacent prostheses 80 are joined by an axial beam 82 which preferably includes a weakened segment 84 near its midpoint. The use of such a joining structure, which will require physical breakage (as opposed to the simple detachment characteristic of the embodiment of FIGS. 5 and 6) is advantageous in that it provides a very strong linkage which permits both the application of axial compression and axial tension without decoupling. The disadvantage of such a linkage is that it usually requires some mechanism or capability to be incorporated in the delivery catheter to permit selective breakage of the couple.

Referring now to FIGS. 8A-8C, a catheter 100 suitable for delivering a plurality of self-expanding prostheses 102 will be described. Catheter 100 comprises a sheath 104 having an axial lumen which carries the prostheses 102 near its distal end 106. A pusher tube 108 is also positioned in the lumen and is located proximally of the proximal most prosthesis 102. The individual prostheses 102 may be delivered into a body lumen, typically a blood vessel BV, as illustrated in FIG. 8B. The catheter is introduced over a guidewire GW to a desired target site in the blood vessel BV. When at the target site, a first of the prostheses 102 is deployed by axially advancing the pusher tube 104 so that the line of prostheses 102 is axially advanced, with the distal-most prostheses being released from the distal end 106 of the catheter. As it is released, the distal-most prostheses 102 expands since it is being released from the radial constraint provided by the sheath 104.

Figure 9C:
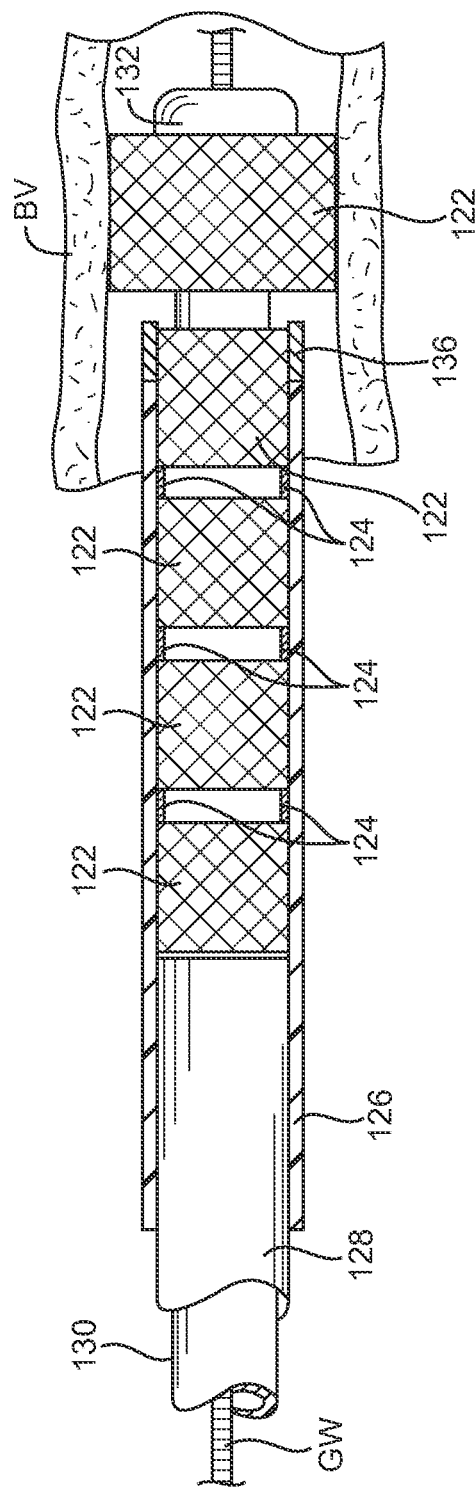

Catheter 100 of FIGS. 8A-8C is intended for delivering prostheses which abut each other in an end-to-end manner, but which are otherwise unconnected. A catheter 120 intended for releasing self-expanding prostheses 122 which are mechanically linked by frangible coupling elements 124 is illustrated in FIGS. 9A-9C. The prostheses 122 and coupling elements 124 may be similar to the prosthesis structure shown in FIG. 7, or may comprise other linked prosthesis or stent structures, for example as shown in U.S. Pat. No. 6,258,117, the disclosure of which is incorporated herein by reference.

Catheter 120 comprises a sheath 126, a pusher tube 128, and a catheter body 130 having a shearing element 132 at its distal end. Conveniently, the pusher tube 128 is coaxially received over a shaft 134 of the catheter body 130. In this way, the pusher tube may be used to axially advance each prosthesis 122 by pushing on the proximal end of the proximal-most prosthesis, as shown in FIG. 9B.

The catheter 120 is advanced over a guidewire GW to a desired target site in a blood vessel BV. After reaching the target site, at least a first prosthesis 122 is advanced from the distal end of the sheath so that it radially expands to engage an inner wall of the blood vessel. After the at least one prosthesis 122 is advanced sufficiently far, the frangible coupling elements 124 will reach a shearing element 136, typically a metal ring, disposed at the distal end of the sheath 126. By then axially retracting the catheter body 130, a chamfered surface 138 of the shearing element 132 is engaged against the shearing element 136 in order to shear the links 122, releasing the prosthesis 122, as illustrated in FIG. 9C. After deployment and release of the first prosthesis 122, additional prosthesis 122 may be released adjacent to the first prosthesis or at different, axially spaced-apart locations within the blood vessel.

Referring now to FIGS. 10A-10C, a catheter 140 for delivering a plurality of heat expansible prostheses 142 is illustrated. The prostheses 142 are composed of a heat memory alloy, such as a nickel titanium alloy, which has been programmed to remain in an unexpanded configuration when maintained at body temperature or below, and to assume an expanded configuration when exposed to temperatures above body temperature, typically temperatures above 43° C., often above 45° C. The prostheses will have coupling members which anchor successive prostheses 142 together, typically the radially separating anchors illustrated in FIGS. 5A-5F.

The catheter 140 includes a sheath 144 and a pusher tube 146. The catheter 140 is advanced to a desired target site within the blood vessel BV over a guidewire GW in a conventional manner. After the distal-most prostheses 142 has been fully advanced from the sheath 144 (usually by retracting the sheath 144 while the prostheses are held stationary relative to the blood vessel BV using the pusher tube 146), as shown in FIG. 10B, it will remain both unexpanded and attached to the next proximal prosthesis 142 which remains within the sheath. It is important that the advanced prosthesis 142 be anchored or tethered to the remaining prostheses since it has not yet been expanded and it would otherwise be lost into the lumen of the blood vessel.

After the uncovered prosthesis is properly positioned, a heated medium may be introduced through a lumen of the catheter body 148 so that it flows outwardly through the interior of the distal-most prosthesis 142. By properly selecting the temperature of the heated medium, the prosthesis to be deployed can be heated sufficiently to induce radial expansion, as illustrated in FIG. 10C. By positioning the catheter body 148 so that its distal tip is coterminous with the distal tip of the sheath 144, inadvertent heating of the prostheses 142 which remain within the sheath can be avoided. After the prosthesis 142 has radially expanded, it will separate from the coupling elements 148 located on the next prosthesis which remains within the sheath 144. Additional ones or groups of prostheses 142 may then be deployed, either at the same target site or at a different target site axially spaced-apart within the lumen of the blood vessel BV.

Figure 11:
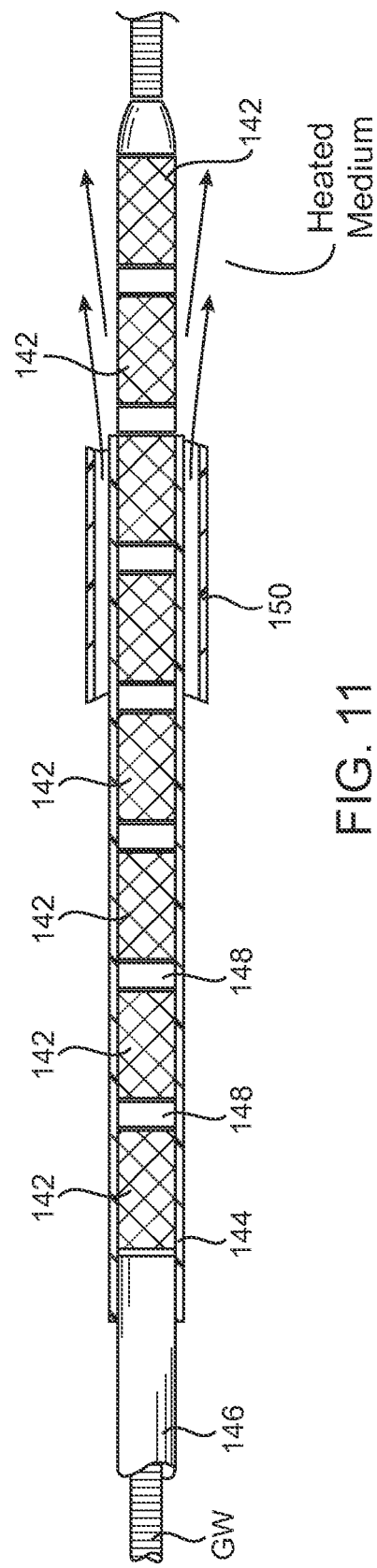
FIG. 11 illustrates an alternative catheter construction for delivering multiple prostheses via a heat-induction protocol in accordance with the principles of the present invention.

As illustrated in FIG. 11, instead of using an internal catheter body 148, as illustrated in FIGS. 10A-10C, an external sheath 150 may be used to deliver the heated medium around one or more deployed prostheses 142. Other aspects of the construction of catheter 140 may remain the same. Optionally, if prosthesis is martensitic at body temperature, further radial expansion can be achieved by internal balloon expansion.

Figure 12D:
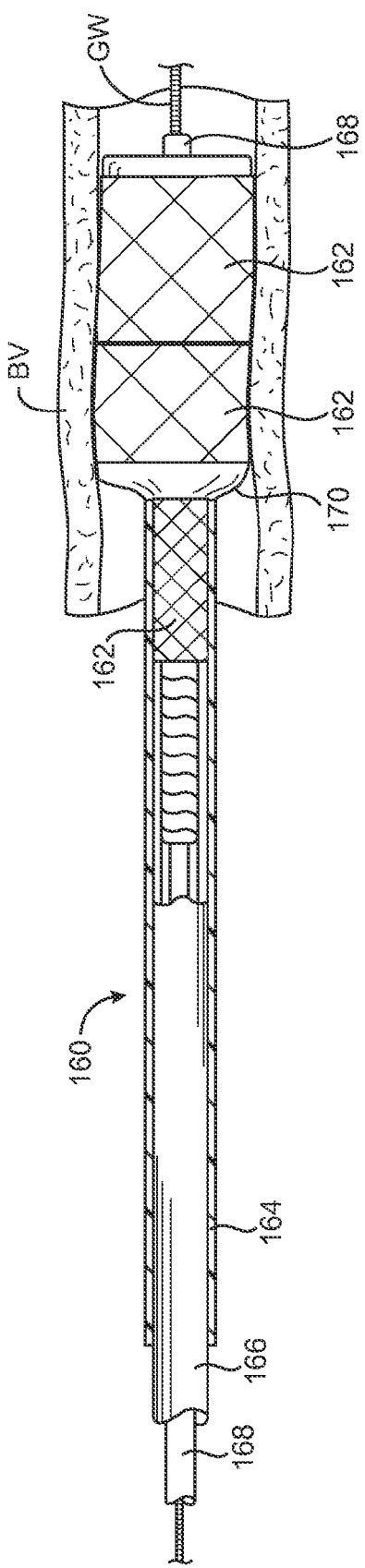

Referring now to FIGS. 12A-12D, catheter 160 intended for delivery of multiple prostheses 162 by balloon deployment is illustrated. Catheter 160 comprises a sheath 164, pusher tube 166, and a catheter body 168. The catheter body 168 includes an expansible balloon 170 over its distal portion. Individual prostheses 162 are deployed, as illustrated in FIGS. 12B and 12C, by crossing the target area with catheter 160 and then retracting sheath 164. A distal portion of the balloon 170 lies within the distal-most deployed prosthesis 162, as shown in FIG. 12B. The remaining proximal portion of the balloon 170 will, of course, remain within the other prostheses 162 which themselves remain within the sheath 164. The balloon 170 is then inflated, but only the distal portion of the balloon beyond the sheath inflates within the distal prosthesis 162, as illustrated in FIG. 12C. Expansion of the remaining proximal portion of the balloon is prevented by the sheath 164. Similarly, the remaining prostheses 162 remain unexpanded since they remain within the sheath 164. After deployment of prostheses 162, balloon 170 may be deflated and retracted into sheath 164 and remaining prostheses 162.

Referring now to FIG. 12D, additional prostheses 162 may be deployed, either at the same target location within the blood vessel or at a different, spaced-apart locations within the blood vessel. Deployment of two prostheses 162 is illustrated. The two prostheses 162 are axially exposed as the sheath is retracted over the stents which are positioned over the uninflated balloon 170. The balloon 170 is then inflated, as illustrated in FIG. 12D, thus expanding the prostheses 162 within the blood vessel BV. It will be appreciated that the catheter 160 could carry many more than the four illustrated prostheses 162, and three, four, five, ten, and even 20 or more individual prostheses could be deployed at one time, with additional single prostheses or groups of prostheses being deployed at different times and/or at different locations within the blood vessel.

Figure 13D:
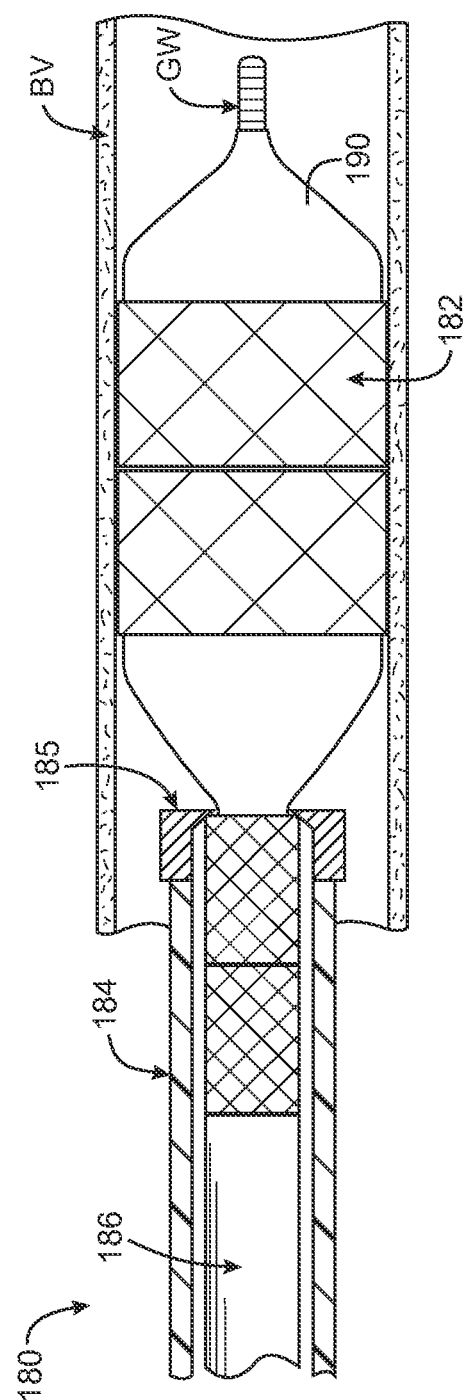

Referring now to FIGS. 13A-13D, another embodiment of a catheter 180 intended for delivery of multiple prostheses 182 by balloon deployment is illustrated. In this embodiment, catheter 180 comprises a sheath 184 having a valve member 185 at its distal end, a pusher tube 186, and a catheter body 188. The catheter body 188 includes an expansible balloon 190 over its distal portion. To deploy prostheses 182, as illustrated in FIG. 13B, a predetermined number of prostheses 182 is first exposed by retracting sheath 184 proximally (arrows) while holding pusher tube 186 in place. As shown in FIGS. 13B and 13C, valve member 185 may be used to engage a distal end of one of the prostheses 182 and the sheath 184 and the pusher tube may be retracted proximally together (arrows in FIG. 13C) to separate a proximal number of prostheses 182 from a distal number of prostheses 182. The distal portion of the balloon 190 lies within the distal, deployed prostheses 182. The remaining proximal portion of the balloon 190 will remain within the other prostheses 182 which themselves remain within the sheath 184. The balloon 190 is then inflated, as shown in FIG. 13D, but only the distal portion of the balloon inflates within the distal prostheses 182, as illustrated in FIG. 12C. Expansion of the remaining proximal portion of the balloon is prevented by the sheath 184. Similarly, the remaining prostheses 182 remain unexpanded since they remain within the sheath 184.

Referring now to FIG. 13D, single or multiple prostheses 182 may be deployed at the same target location within the blood vessel. Additional prostheses 182 may also be deployed at different, spaced-apart locations within the blood vessel. Deployment of two prostheses 182 is illustrated at one location in FIG. 13D. It will be appreciated that the catheter 180 could carry many more than the four illustrated prostheses 182, and three, four, five, ten, and even 20 or more individual prostheses could be deployed at one time, with additional single prostheses or groups of prostheses being deployed at different times and/or at different locations within the blood vessel.

Figure 14:
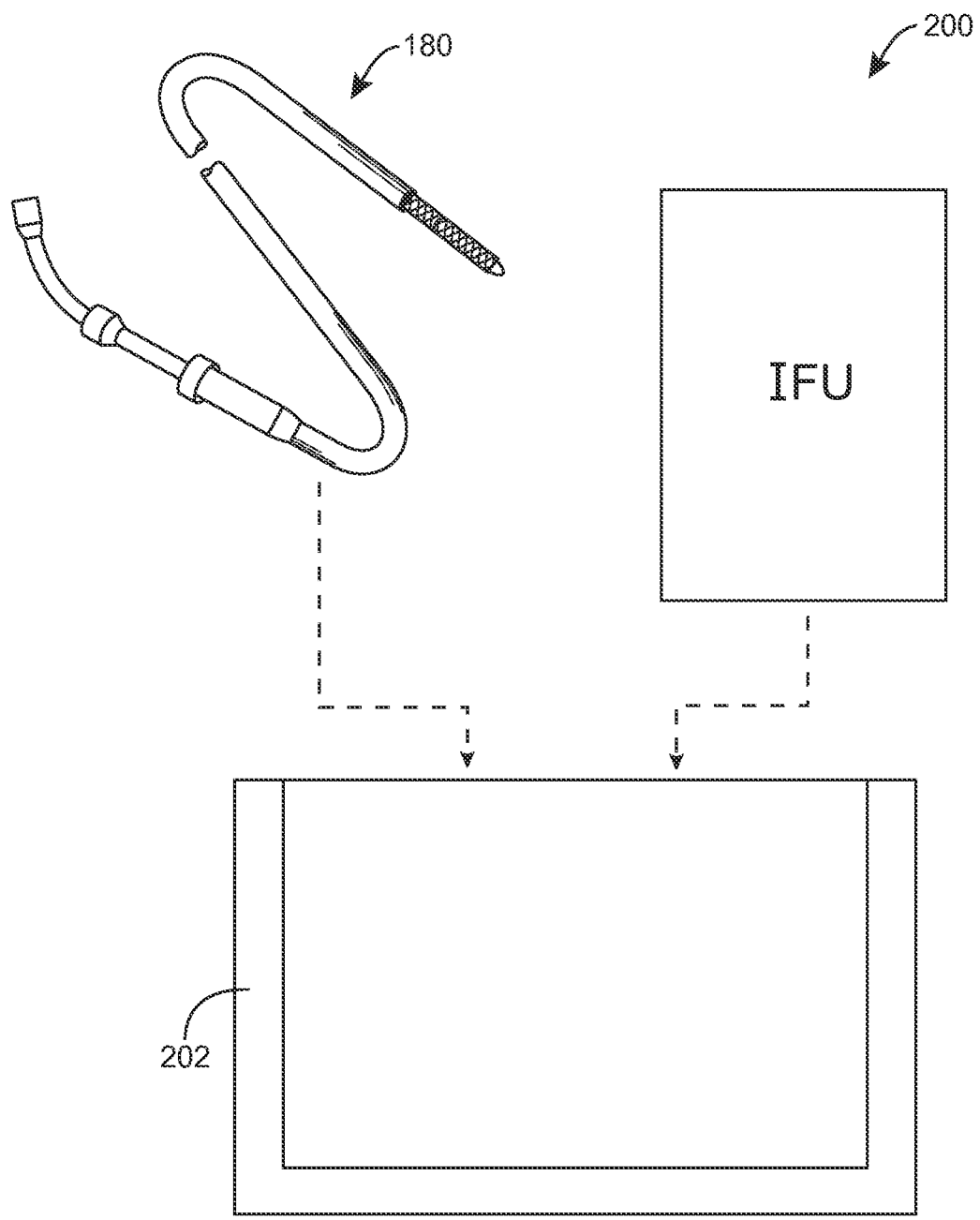
FIG. 14 illustrates an exemplary kit constructed in accordance with the principles of the present invention.

Referring now to FIG. 14, kits 200 according to the present invention comprise a catheter 160 (or any other of the illustrated catheters of the present invention) in combination with instructions for use IFU. The instructions for use set forth any of the methods of the present invention, and in particular set forth how the catheter 180 may be used to implant single or multiple prostheses within a blood vessel or other body lumen. The catheter 180 and instructions for use will typically be packaged together, for example within a conventional package 202, such as a box, tube, pouch, tray, or the like. Catheter 160 will typically be maintained in a sterile condition within the package 202. The instructions for use may be provided on a package insert, may be printed in whole or in part on the packaging, or may be provided in other ways, such as electronically over the internet, on an electronic medium, such as a CD, DVD, or the like.

Referring now to FIGS. 15-45, further embodiments of a valve member 185 adapted to facilitate selective deployment of one or more prostheses at a target site will be described. FIGS. 15A-15B illustrate a valve member 185 having a pair of lobes 210 extending from the inner wall of sheath 184 radially inward into the passageway 211 in sheath 184. Lobes 210 are configured to engage the distal edge of prosthesis 182 and inhibit its movement distally out of the sheath until sufficient force is exerted upon pusher tube 186. Lobes 210 are preferably integrally formed with the wall of sheath 184, but alternatively may be separate components that are fixed with adhesive or by other means to sheath 184. In an exemplary embodiment, lobes 210 are each in the shape of a rounded linear ridge transverse to the axial direction and are generally parallel to each other on opposite sides of passageway 211. Lobes 210 may have alternative shapes as well, such as having angular, non-rounded walls, walls sloping to a peak along the radially inner edge, and/or a curvature about the axial direction. Lobes 210 are sufficiently lubricious, flexible, and/ or shaped to allow prostheses 182 to pass over them without excessive interference. In some cases, lobes 210 may be of sufficient height to deflect and even deform prostheses 182 as they are advanced past lobes 210, but any such deformation will not be so great as to inhibit advancement of prostheses 182 over balloon 190. Alternatively, lobes 210 may be sufficiently flexible and resilient so as to deflect when engaged by prostheses 182, rather than causing deformation of the prostheses.

FIGS. 16A-16B illustrate another embodiment of valve member 185 which has a pair of lobes 212 each having a curb 214, a sloping inner surface 216, and a lip 218. Again, lobes 212 may be formed integrally with the walls of sheath 184 or fixed thereto as one or more separate components. Lobes 212 are made with a shape and material that will allow prostheses 182 to be advanced across lobes 212 without damage or excessive deformation, preferably being a biocompatible polymer with flexibility, resiliency and lubricity. Prostheses 182 engage curb 214 initially, and further advancement is prevented without exerting greater force upon pusher tube 186. This provides to the user an initial indication that the prostheses 182 are against the proximal edge of valve 185. When additional force is applied, prostheses 182 are then pushed through the tapered passage 220 between inner surfaces 216, causing the prostheses to deflect or deform. The distal prosthesis 182 then engages lip 218 and is again stopped from further advancement without exerting more force on pusher tube 186. This provides to the user a second indication that the distal-most prosthesis 182' has reached the distal end of valve 185 and is ready for deployment. Further, when the distal-most prosthesis 182' is advanced across lip 218, the user can feel when the next prosthesis in line has engaged lip 218, thus indicating that the distal-most prosthesis 182' is fully released from valve 185. In this way the user can count the number of prostheses 182 that have been advanced beyond the valve 185. When balloon 190 along with the desired number of prostheses has been extended beyond the distal end of sheath 184, the force against pusher tube 186 may be reduced and balloon 190 may be advanced further distally to deploy the prostheses at the treatment site. Lip 218, along with inner surfaces 216, retain the next prosthesis 182 within sheath 184 as the balloon is advanced, thus separating the distal prosthesis 182' from the remaining prostheses 182.

FIGS. 17A-17B illustrate an alternative embodiment of valve member 185 similar to that of FIGS. 16A-16B, but without curb 214 or lip 218. Valve member 185 comprises a pair of tapered lobes 220 having sloping inner surfaces 222. In a preferred embodiment, inner surfaces 222 slope at an angle of approximately 10-40° such that the distance between opposing inner surfaces 222 is about 0.7-1.5 mm at the proximal end of valve 185 and is about 0.5-1.3 mm at the distal end of valve 185. When prostheses 182 engage inner surfaces 222, the user must exert more force on pusher tube 186 to advance prostheses 182 distally. As the prostheses 182 are advanced through valve member 185 they are deformed into a flattened configuration, with inner surfaces 222 applying a frictional force against the outer surface of prostheses 182. Distal force may be applied to pusher tube 186 until the desired number of prostheses is advanced with balloon 190 distally of sheath 184. The force on pusher tube 186 may then be relaxed, and balloon 190 moved further distally relative to sheath 184 to separate the stents to be deployed from the those remaining in the sheath. Valve 185 exerts sufficient force on the remaining prostheses 182 in sheath 184 so that they remain in place in sheath 184 while the balloon is advanced the desired distance.

FIGS. 18A-18B illustrate a further embodiment of a valve member 185 according to the invention. Valve member 185 comprises a tubular member 224 having an inner diameter that is less than the inner diameter of sheath 184. In an exemplary embodiment suitable for coronary applications, the tubular member 224 has an inner diameter about 0.05-0.3 mm less than that of sheath 184. Tubular member 224 may be a polymer or metal and is either fixed to the end of sheath 224 in a butt joint as shown, or positioned within the interior of sheath 224 and fixed to its inner wall. Tubular member 224 may be either constant diameter across its length, or it may taper from a wider to narrower diameter across all or part of its length. Usually, tubular member 224 will have a length sufficient to retain at least one prosthesis 182 therein. In this way, prostheses 182 may be advanced until the distal-most prosthesis 182' reaches tubular member 224. The user then will be required to exert more force on pusher tube 186 to advance prostheses 182 to the distal end of tubular member 224. Balloon 190 is then advanced distally relative to sheath 184, with the user continuing to exert the same force on pusher tube 186, until balloon 190 with the desired number of prostheses is exposed beyond the distal end of sheath 184. Force on pusher tube 186 is then relaxed and balloon 190 is extended further from sheath 184 to separate the prostheses to be deployed from those remaining in sheath 184. Balloon 190 may then be expanded to deploy the prostheses in the vessel.

FIGS. 19A-19B illustrate an embodiment of valve member 185 that combines aspects of the embodiments of FIGS. 18A-18B and FIGS. 15A-15B. Valve member 185 comprises a tubular body 226 and a pair of distal lobes 228. As in the embodiment of FIGS. 18A-18B, tubular body 226 has an inner diameter that is less than the inner diameter of sheath 184 so as to frictionally engage the outer surfaces of prostheses 182. Tubular body 226 may be joined to the distal end of sheath 184, or mounted to its interior wall near its distal end. In cross-section, lobes 228 are preferably peaked as shown, but alternatively may be rounded, flattened, trapezoidal, or other shapes. Lobes 228 may be either a polymer or metal and may be hard and inflexible, resilient and flexible, lubricious, or frictional, depending upon the geometry of lobes 228, the prostheses used, the desired release force, and other factors. Further, as an alternative to lobes 228, an annular rib may extend circumferentially around the inner wall of tubular body 226, the annular rib extending radially inward to engage prostheses 182. Lobes 228 or the annular rib may be integrally formed with tubular body 226 or may be one or more separate components fixed thereto with adhesive or other means. In an exemplary embodiment, tubular body 226 has an inner diameter about 0.0-0.2 mm less than the inner diameter of sheath 184, and lobes 228 (or annular rib) extend inwardly about 0.2-0.4 mm from the inner wall of tubular body 226. Valve 185 operates much like the embodiments described above.

FIGS. 20A-20B, an additional embodiment of valve 185 is illustrated wherein a plurality of annular ribs 229 extend circumferentially around the inner wall of sheath 184 and extend radially inward therefrom to engage prostheses 182. Annular ribs 229 are disposed along the distal extremity of sheath 184 and are preferably spaced apart a distance equal to or just larger than the length of one of prostheses 182, in an exemplary embodiment being about 1-10 mm apart, depending upon the length of the prostheses used. In this way, one prosthesis 182 fits snugly between two annular ribs 229. Annular ribs 229 have an inner diameter smaller than the inner diameter of sheath 184, usually being about 0.2-0.4 mm smaller for coronary applications. In use, prostheses 182 are advanced distally by pushing on pusher tube 186. Pusher tube 186 engages the most proximal prosthesis 182, which is urged past the first annular rib 229 until it engages the next prosthesis 182, which is then pushed past the next annular rib 229, and so on until the distal-most prosthesis 182' is pushed past the last annular rib 229'. Balloon 190 may be advanced distally along with the prostheses 182 so that balloon 190 and prostheses 182 mounted thereon extend beyond the distal end of sheath 184. Force on pusher tube 186 is then relaxed and balloon 190 and the prostheses 182 to be deployed are advanced a desired distance beyond the sheath 184. Annular ribs 229 engage those prostheses 182 remaining in sheath 184 so that they remain in place as balloon 190 is advanced. Because multiple annular ribs 229 are used to engage multiple prostheses 182, the retention force is distributed among many or all of the prostheses, thus being more effective in retaining the prostheses in the sheath as the balloon is advanced.

An alternative to the embodiment of FIGS. 20A-20B is shown in FIGS. 21A-21B. This embodiment includes a plurality of spaced-apart annular ribs 229 as in the foregoing embodiment, but adds a pair of lobes 230 near the distal end of sheath 184 much like lobes 228 of FIGS. 19A-19B. Lobes 230 extend radially inward from the wall of sheath 184 a greater distance than annular ribs 229, and, as in earlier embodiments, may be flexible or rigid, rounded or angular, smooth or frictional, depending upon the degree of force to be exerted on prostheses 182. In any event, lobes 230 are configured to require a higher distal force to be exerted upon prostheses 182 to cross lobes 230 than is required to cross annular ribs 229. In this way, the force required to restrain prostheses 182 within sheath 184 is partially distributed among multiple prostheses 182 by annular ribs 229, as in the previous embodiment. However, the addition of lobes 230 creates an additional threshold force that must be applied to actually deploy one of prostheses 182 from the distal end of sheath 184. Thus, by applying a medium amount of force to pusher 186, the user can advance prostheses 182 up to lobes 230 without deploying them out of sheath 184. By applying additional force, a desired number of prostheses 182 may be advanced distally past lobes 230 to allow deployment in the vessel.

It should be understood that in either of the foregoing embodiments illustrated in FIGS. 20A-20B and FIGS. 21A-21B, a plurality of lobe pairs like lobes 228 of FIG. 19A may be used in place of annular ribs 229. In the embodiment of FIGS. 21A-21B, such lobe pairs will preferably extend radially inward a smaller distance than the larger distal lobe 230 so that the force required to deploy prostheses 182 out of sheath 184 is greater than that required to advance prosthesis 182 though sheath 184 up to lobes 230.

The embodiment of valve 185 shown in FIGS. 22A-22B is similar to the embodiment of FIGS. 21A-21B, combining a single annular rib 232 spaced proximally from the distal end 236 of sheath 184, with a pair of lobes 234 closer to distal end 236. The primary difference in this embodiment is the use of a single annular rib 232 rather than the multiple ribs used in earlier embodiments. Thus, lobes 234 act as a primary valve while annular rib 232 functions as a secondary valve. The relative sizes of the primary and secondary valves may be selected to achieve the optimal degree of force required advance prostheses 182 up to lobes 234 and that required to advance the distal prosthesis 182' across lobes 234 to exit sheath 184. It will be appreciated that a second pair of lobes of smaller size may be used as a secondary valve in place of annular rib 232, and similarly, an annular rib of larger size may be used as the primary valve in place of lobes 234.

Referring now to FIGS. 23A-23C, a further embodiment of a valve member 185 according to the invention will be described. In this embodiment, valve member 185 comprises a plurality of projections 238 extending radially inward from the inner wall of sheath 184 a sufficient distance to engage prostheses 182. Projections 238 are arranged in a series of annular rows, each row preferably being axially spaced apart a distance approximately equal to the length of one of prostheses 182. Each annular row may have from 2 to 12 or more projections 238, the embodiment illustrated having 6 projections 238, which are spaced evenly around the interior circumference of sheath 184. Projections 238 may be rigid such that prostheses 182 deflect or deform as they are advanced, or projections 238 may be flexible and resilient so as to deflect as the prostheses 182 are advanced and then resiliently return to their original position. Projections 238 may have pointed, rounded or flat tips, and may be very thin and flexible or thick and rigid depending upon the characteristics desired.

In a preferred embodiment, projections 238 are configured to extend through spaces in the walls or along the edges of prostheses 182 to keep the prostheses spaced apart and rotationally oriented about the longitudinal axis of sheath 184. In an exemplary embodiment, as shown in FIG. 23C, prostheses 182 comprise a series of sinusoidal struts 240 joined together at the apices or peaks 242 of the sinusoidal pattern. The proximal and distal ends of prostheses 182 thus have a series of peaks 242 and troughs 244. Maintaining the rotational alignment of adjacent prostheses can be important in some circumstances. For this purpose, projections 238 are configured to be disposed in troughs 244 (between peaks 242) at the proximal and distal ends of prostheses 182, thus restricting rotation of prostheses 182 within sheath 184. Each time a prosthesis 182 is advanced distally across projections 238, the prosthesis is rotationally indexed by the placement of projections 238 between the peaks, thus maintaining the rotational alignment of adjacent prostheses. It will be understood that the geometry of prosthesis 182 in FIG. 23C is merely illustrative, and that a variety of prosthesis geometries may be utilized wherein the rotational alignment provided by projections 182 is useful.

Referring now to FIGS. 24A-24D, in a further embodiment valve member 185 comprises a tapered nosecone 248 fixed to the distal end of sheath 184. Nosecone 248 is divided into a plurality of deflectable sections 250 having distal tips 252 biased inwardly toward each other. In an undeflected configuration, tips 252 may be in engagement with each other at the central axis of sheath 184, or may be separated from each other to provide an opening at the distal end of nosecone 248. Tips 252 are deflectable outwardly in response to distal pressure exerted against the inner (proximal) surfaces of sections 250 by balloon 190 or prostheses 182 as they are advanced distally from sheath 184 (as shown in phantom in FIG. 24D). The resiliency of sections 250 urges tips 252 against prostheses 182. The shape of tips 252 and the resiliency of sections 248 will be selected to allow prostheses 182 to pass through nosecone 248 to the distal end of balloon 190 when force is exerted upon pusher tube 186. However, when no force is exerted upon pusher tube 186, sections 248 will force tips 252 against prostheses 182 with sufficient force to prevent prostheses 182 from moving distally through nosecone 248, even if balloon 190 is being advanced distally through sheath 184 and any prostheses 182 remaining within sheath 184. Tips 252 preferably taper to a point suitable for engaging the surface of prostheses 182 to facilitate retaining the prostheses in sheath 184. Tips 252 may further be configured to fit within openings or gaps on the surfaces of prostheses 182 to provide further retention force. In an exemplary embodiment, tips 252 have a sloping proximal surface 254 to allow prostheses 182 to move distally through nosecone 248, but have an abrupt distal surface 256 at least about perpendicular to the lateral surface of prostheses 182 that prevents movement of prostheses 182 in the proximal direction, as shown in FIG. 24D.

FIGS. 25A-25B illustrate another embodiment in which valve member 185 comprises an elastic diaphragm valve 260 mounted to the distal end of sheath 184. Diaphragm valve 260 comprises a pair of resilient, deflectable flaps 262 separated by a slit 264. Slit 264 can be so narrow as to allow flaps 262 to engage one another, or can be wider to provide a slot-like opening in diaphragm valve 260. The resiliency of the flaps and the width of slit 264 are selected to provide the optimal retention force upon prostheses 182. In use, balloon 190 is positioned so that its distal end is within sheath 184. Force is then exerted upon pusher tube 186 while advancing balloon 190 distally so that prostheses 182 and balloon 190 both move together. The prostheses 182 engage diaphragm valve 260 and deflect flaps 262 distally, allowing prostheses 182 and balloon 190 to pass through diaphragm valve 260. When the desired number of prostheses 182 on balloon 190 has been advanced distally of diaphragm valve 260, force is released from pusher tube 186 and balloon 190 is advanced slightly further distally relative to sheath 184 in order to separate the prostheses to be deployed from the distal end of sheath 184. The engagement of flaps 262 against the distal-most prosthesis 182' in sheath 184 prevents the prostheses 182 remaining in the sheath from moving distally with balloon 190. Prostheses 182 on balloon 190 outside sheath 184 may then be deployed in the vessel.

FIG. 26 illustrates another embodiment of a valve member 185 that includes a diaphragm valve 260' similar to diaphragm valve 260 of FIGS. 25A-25B. In this embodiment, diaphragm valve 260' is again constructed of a resilient elastic material, but includes a central opening 266 that is preferably round to provide symmetrical engagement of prostheses 182. This defines an annular diaphragm 268 that is deflectable under the force exerted by prostheses 182 as they are pushed distally. Optionally, one or more slits 270 may be provided around the periphery of opening 266 to facilitate deflection of diaphragm 268. In use, diaphragm valve 260' operates in a similar manner to diaphragm valve 260 of FIGS. 25A-25B, described above.

In a further embodiment, valve member 185 comprises, as shown in FIGS. 27A-27B, a plurality of projections 272 attached to the inner wall of sheath 184 and projecting inwardly into the passageway 211 therein. Projections 272 are flexible and adapted to bend or deflect when engaged by prostheses 182. In FIG. 27A, projections 272 comprise a plurality of flexible bristles, preferably mounted in groups or clumps to sheath 184. In FIG. 27B, projections 272 comprise bendable poles, shafts, or teeth. Projections 272 may be mounted only at the distal end of sheath 184 to engage only the distal edge of the distal-most prosthesis 182', or they may be arranged in axial rows to engage a larger portion of the length of one or more prostheses 182. Projections 272 may be an elastomeric polymer, metallic wire, or other biocompatible material having sufficient flexibility to deflect when engaged by prostheses 182 but sufficient stiffness to retain prostheses 182 within sheath 184 as balloon 190 is advanced distally relative to prostheses 182. Bumps, nubs, foam, gauze, or fabric padding mounted to the inner wall of passageway 211 so as to engage prostheses 182 are alternative structures that can be used.

FIGS. 28A-28B illustrate further embodiments of valve member 185 in which one or more annular ribs 274 are disposed on the inner wall of sheath 184. In the example of FIG. 28A, ribs 274 are arranged in a continuous helical pattern around a distal portion of passageway 211 in sheath 184. In FIG. 28B, ribs 274 are separate annular rings. In either case, ribs 274 extend inwardly into passageway 211 so as to engage prostheses 182 (not shown in FIGS. 28A-28B) and thereby retain them within sheath 184 as balloon 190 is advanced distally relative thereto. Preferably, ribs 274 are made of a flexible elastomeric polymer so as to bend or deflect when engaged by prostheses 182. Alternatively, ribs 274 may be constructed of a more rigid polymer or metal that is relatively inflexible and which causes prostheses 182 to deflect inwardly when they contact ribs 274. Ribs 274 may be disposed only at the distal end of sheath 184 to engage only the distal edge of the distal-most prosthesis therein, or may be distributed over a longer length of sheath 184 to engage a greater surface area of the distal-most prosthesis or to engage multiple prostheses. As a further alternative, not illustrated, ribs 274 may be elastomeric O-ring structures mounted within annular grooves or channels in the inner wall of sheath 184. The O-ring structures may roll within their respective channels as prostheses 182 are advanced through them, facilitating movement of prostheses 182 through sheath 184, while providing sufficient inward force against the prostheses to retain them in the sheath as balloon 190 is advance distally relative thereto.

Turning to FIG. 29, in a further embodiment valve member 185 comprises one or more leaf springs 276 cantilevered from the inner wall of sheath 184. Preferably, two leaf springs on opposing sides of passageway 211 are provided, but three, four, or more leaf springs 276 may be included. Leaf springs 276 are resiliently flexible and have distal tips 278 biased inwardly to a position in which they will engage prostheses 182 within passageway 211. When engaged by prostheses 182, leaf springs 276 are deflected outwardly and exert an inward force against prostheses 182 to retain them within sheath 184 as balloon 190 is advanced distally relative thereto. Distal tips 278 preferably have points 280 directed radially inwardly to engage prostheses 182 and thereby facilitate retention of the prostheses as balloon 190 is retracted proximally within prostheses 182. Points 280 are preferably configured to fit within openings within the sidewalls of prostheses 182 or between the ends of adjacent prostheses 182. Multiple points 280, bumps, or other friction-enhancing structures may alternatively be provided along the inner surfaces of leaf springs 276 to enhance engagement with prostheses 182.

FIGS. 30A-30B illustrate another embodiment of a valve member 185 according to the invention. In this embodiment, valve member 185 comprises an annular rib 284 fixed to the inner wall of sheath 184 and extending radially into passageway 211 sufficiently to engage prostheses 182. Annular rib 284 is preferably integrally formed with the wall of sheath 184 and is composed of the same polymer as sheath 184. In order to increase the rigidity of rib 284 so as to increase the retention force against prostheses 182, a stiffener 286 is mounted within rib 284. Stiffener 286 may comprise a plurality of separate curved elements disposed about the circumference of rib 284, or a single continuous ring embedded within rib 284. Stiffener 286 is preferably composed of a material more rigid than that of rib 284, such as a rigid polymer or metal.

In FIG. 31, a further embodiment of valve member 185 has an inflatable bladder 288 fixed to the inner wall of sheath 184. An inflation lumen 290 is in communication with bladder 288 and extends through sheath 184 from an inflation port 292 at the proximal end thereof. Bladder 288 may be single continuous annular ring or torroidal member extending around the entire circumference of sheath 184, or may have a plurality of separate inflatable sections disposed about the circumference passageway 211. When uninflated, bladder 288 contracts to a position in which prostheses 182 can pass freely out of passageway 211 in sheath 184. When filled with an inflation fluid such as saline, bladder 288 expands to a shape in which it engages prostheses 182 with sufficient force to retain them within sheath 184 as balloon 190 is advanced distally relative to the sheath and prostheses therein. Bladder 288 is constructed of a flexible polymer, and will usually be a distensible elastomer that resiliently recoils from its inflated shape to its uninflated, contracted shape when evacuated of fluid.

FIG. 32 illustrates an alternative embodiment of an inflatable valve member 185 that includes a plurality of inflatable members 294 attached to the inner wall of sheath 184. Each inflatable member 294 is in communication with an inflation lumen 296 extending to an inflation port (not shown) at the proximal end of sheath 184. The inflatable members 294 can be inflated to engage prostheses 182 in passageway 211. As in the embodiment of FIG. 31, inflatable members 294 are preferably constructed of a resilient elastomer so as to elastically expand during inflation and recoil to a collapsed configuration when evacuated of fluid. Inflatable members 294 may be sized so as to contact all or part of only the distal-most prosthesis 182', or may be longer so as to contact multiple prostheses 182. As a further alternative, rather than inflating inflatable members 294 each time prostheses 182 are to be retained in sheath 184, a passive approach may be used wherein inflatable members 294 are maintained in a fully or partially inflated condition so as to frictionally engage prostheses 182. The level of inflation is maintained such that prostheses 182 can be advanced through inflatable members 294 when sufficient force is exerted on pusher tube 186, but in the absence of force on pusher tube 186, prostheses 182 are retained in sheath 184, even as balloon 190 is advanced distally. In such a passive embodiment, inflatable members 294 could be permanently filled with a fluid and require no inflation lumens 296. The fluid can be a liquid such as saline, a gas such as air or helium, or a semi-solid gel.

FIG. 33 illustrates an additional embodiment of an active valve member 185 which comprises a pawl 298 pivotably coupled to sheath 184 near the distal end of passageway 211. Pawl 298 has a distal end 300 configured to engage prostheses 182 and a proximal end 302 coupled to a pull wire 304 extending through a lumen 306 in sheath 184. A coil spring 308 biases pawl 298 such that distal end 300 extends into passageway 211 to engage the distal end of prosthesis 182'. Exerting tension on pull wire 304 pivots pawl 298 so as to retract distal end 300 from passageway 211, allowing prostheses 182 to advance distally under the force of pusher tube 186. When the desired number of prostheses have been advanced, tension is released from pullwire 304 so that distal end 300 engages distal-most prosthesis 182'. Balloon 190 may then be pushed further distally relative to sheath 184 without further movement of prostheses 182.

An alternative embodiment of an active valve member 185 is illustrated in FIGS. 34A-34B. In this embodiment, valve member 185 comprises a piston 310 slidably disposed in a channel 312 in sheath 184 that extends to a fluid port 314 at the proximal end of sheath 184. A pin 316 is attached to piston 310 and extends through an opening 318 into passageway 211 in sheath 184, such that slidable movement of piston 310 moves pin 316 into and out of passageway 211. A spring 320 biases piston 310 in the proximal direction so that pin 316 is refracted from passageway 211. In an exemplary embodiment, pin 316 is flexible and extends through a curved passage 322 in sheath 184 that deflects pin 316 through opening 318. By delivering fluid through fluid port 314, channel 312 is pressurized so as to drive piston 310 distally, extending pin 316 into passageway 211 and preventing prostheses 182 from exiting sheath 184. Relieving fluid pressure from channel 312 allows piston 310 to return to its proximal position, retracting pin 316 so that prostheses 182 can advance distally with balloon 190.

FIG. 35 illustrates an alternative embodiment of an active valve member 185 similar to that of FIGS. 34A-34B. A flexible pin 323 is slidably disposed in a curved passage 324 in sheath 184 and is extendable through an opening 325 into passageway 211. Instead of being actuated by a hydraulic piston as in FIGS. 34A-34B, a rod 327 extends through a channel 329 to the proximal end of sheath 184 and is slidable distally and proximally to extend or retract pin 323 to engage or release prostheses 182.

FIGS. 36A-36B illustrate alternative embodiments of an inflatable valve member 185. Valve member 185 includes at least two tapered balloons 326 disposed on opposing sides of passageway 211 in sheath 184. Tapered balloons 326 are each in communication with an inflation lumen 328 in sheath 184. Tapered balloons 326 taper to a narrow ridge or pointed tip 330 configured to be positioned between the ends of adjacent prostheses 182 when inflated. Tapered balloons 326 have a wider base portion 332 that is configured to collapse to a narrow configuration when deflated and to bulge outwardly when inflated. In this way, when the desired number of prostheses 182 have been advanced distally with balloon 190 out of sheath 184, tapered balloons 326 are inflated sufficiently to extend tips 330 in between the distal-most prosthesis 182' within sheath 184, and the adjacent prosthesis outside of sheath 184. As balloons 326 are fully inflated, base portions 332 bulge outwardly, separating the prostheses to be deployed from those remaining in sheath 184, as shown in FIG. 36B. This separation protects prostheses 182 within the sheath from being expanded by balloon 190 as the other prostheses are deployed in the vessel.

Referring to FIG. 37, still another embodiment of valve member 185 of the invention will be described. In this embodiment, valve member 185 comprises a loop 336 of a heat-activated shape memory alloy such as Nitinol extending around the circumference of passageway 211 near the distal end of sheath 184. A wire 338 extends from loop 336 through channels 340 to the proximal end of sheath 184 for the delivery of electrical current to loop 336. Loop 336 is has an expanded shape at body temperature that is sufficiently large to allow prostheses 182 to pass through loop 336 distally and to exit sheath 184. When current is delivered to loop 336, it rises in temperature and contracts to a contracted shape in which it engages the sidewalls of the distal-most prosthesis 182', as shown in FIG. 37B. In this way, prostheses 182 may be advanced on balloon 190 (not shown) with loop 336 in the expanded shape until the desired number of prostheses has been moved distally of sheath 184. Current may then be delivered to loop 336 so that it contracts around the distal-most prosthesis 182', preventing the remaining prostheses from exiting the sheath as balloon 190 is advanced further for deployment.

FIG. 38 illustrates an alternative embodiment of a valve member 185 utilizing heat-activated shape-memory alloy. Valve member 185 includes at least two loops 342 extending partially into passageway 211 from openings 344 in the inner sidewall of sheath 184. Loops 342 are connected to wires 346 extending to the proximal end of sheath 184 through channels 348. Loops 342 are again composed of heat-activated shape memory alloy material, and have a contracted shape at body temperature in which loops 342 are retracted into openings 344 and do not inhibit movement of prostheses 182 distally through passageway 211. When current is delivered to loops 342, they are heated and expand to an expanded shape in which they engage prostheses 182 within passageway 211, preventing them from advancing distally with balloon 190.

FIG. 39 illustrates yet another embodiment of an active valve member 185, wherein an outer sheath 350 is slidably disposed over sheath 184. Sheath 184 has a flared distal end 352 having an outer diameter that gradually increases as the distal end is approached. As the outer sheath 350 slides distally relative to sheath 184, the inner wall of outer sheath 350 engages the flared distal end 352 of sheath 184, collapsing sheath 184 around prostheses 182 therein. This frictional engagement with prostheses 182 prevents them from moving distally through passageway 211 while allowing balloon 190, along with any prostheses outside sheath 184, to be advanced distally relative to sheath 184. To facilitate the collapse of distal end 352, one or more axial slits (not shown) may be provided in the sidewall of sheath 184 along tapered distal end 352.

FIG. 40 illustrates a further embodiment of a passive valve member 185 according to the invention. In the embodiment of FIG. 40, one or more magnets 354 are mounted to sheath 184 near its distal end. Magnet 354 may be a single annular structure disposed about the circumference of passageway 211, or may comprise a plurality of separate magnets mounted at various positions around the circumference of passageway 211. Magnet 354 has a magnetic attraction to the metallic material of prostheses 182 so as to resist passage of prostheses 182 out of sheath 184. The strength of magnet 354 is selected to allow prostheses 182 to pass out of sheath 184 when being pushed by pusher tube 186, but to prevent prostheses 182 from advancing out of sheath 184 when only balloon 190 is being moved distally.

In the embodiment of FIG. 41, valve member 185 comprises a lumen 356 in sheath 184 that is in communication with passageway 211 through a plurality of suction ports 358. By applying suction through lumen 356, negative pressure is applied to passageway 211 thereby resisting the advancement of prostheses 182 beyond suction ports 358. The number and configuration of suction ports 358, as well as the strength of suction applied, is selected to allow prostheses 182 to pass out of sheath 184 when being pushed by pusher tube 186, but to prevent prostheses 182 from advancing out of sheath 184 when only balloon 190 is being moved distally. In this embodiment, valve member 185 can operate in an active manner, wherein suction is applied only when prostheses 182 are to be retained in sheath 184, or in a passive manner, wherein suction is applied continuously.

Figure 42:
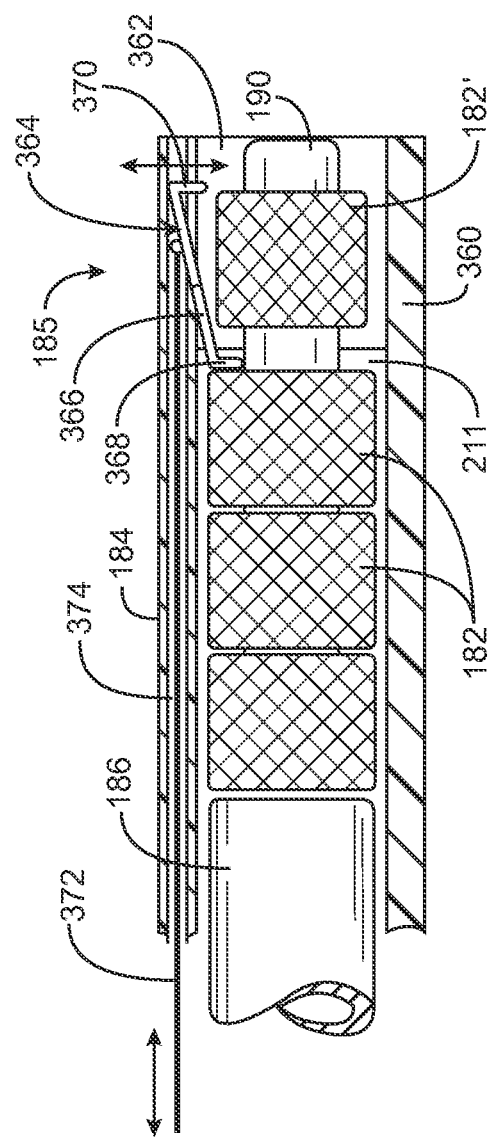

FIG. 42 illustrates a further embodiment of a valve member 185 according to the invention. In this embodiment, a tubular garage member 360 is mounted to the distal end of sheath 184. Garage member 360 has an inner chamber 362 that communicates with passageway 211 in sheath 184 and has a length preferably equal to or slightly larger than one of prostheses 182. A binary switch 364 is mounted to sheath 184 and/or garage member 360 and is movable between two states: (1) garage member open, sheath closed; and (2) garage member closed, sheath open. In an exemplary embodiment, binary switch 364 comprises a rocker arm 366 pivotally mounted to garage member 360. Rocker arm 366 has a proximal end extension 368 which extends into passageway 211 in sheath 184, and a distal end extension 370 which extends into chamber 362 of garage member 360. A rod 372 is coupled to rocker arm 366 and is slidably disposed in a channel 374 extending to the proximal end of sheath 184. FIG. 42 illustrates binary switch 364 in the first state in which distal end extension 370 is retracted from chamber 362 and proximal end extension 368 is extended into passageway 211. In this state, the distal-most prosthesis 182' within garage member 360 is able to be advanced distally out of chamber 362 with balloon 190, while the remainder of prostheses 182 in sheath 184 are retained in passageway 211. If additional prostheses 182 are to be deployed along with distal-most prosthesis 182', binary switch 364 can be moved to the second state by pushing rod 372, extending distal end extension 370 into chamber 362 and retracting proximal end extension 368 from passageway 211. In this state, an additional prosthesis 182 in sheath 184 can be advanced over balloon 190 into garage member 360 until it engages distal end extension 370. Binary switch 364 can then be returned to the first state, retracting distal end extension 370 from chamber 362 and extending proximal end extension 368 into passageway 211, engaging the distal prosthesis 182 therein. Balloon 190 can then be advanced distally relative to sheath 184, carrying with it the additional prosthesis 182 from chamber 362. It will be understood to those of skill in the art that the embodiment of binary switch 364 illustrated in FIG. 42 is merely exemplary, and a variety of structures and mechanisms may be employed to perform the same function, including hydraulic, inflatable, as well as mechanical mechanisms.

A further embodiment of catheter 10 according to the invention is illustrated in FIGS. 43A-43B in which a shuttle member 375 is provided for advancing prostheses 182 a preselected distance relative to sheath 184. In this embodiment, sheath 184 has a first valve structure 376 near the distal end of passageway 211. First valve structure 376 may be constructed like any of the embodiments of valve member 185 described above, including, for example, a pair of lobes 378 similar to those described in connection with FIG. 15A. Shuttle member 375 comprises an outer sheath 380 slidably disposed over sheath 184. Outer sheath 380 has a second valve structure 382 extending radially inwardly and configured to engage the distal-most prosthesis 182'. Second valve structure 382 may be also be similar to any of the embodiments of valve member 185 described above, including, for example, a pair of lobes 384 extending inwardly from opposing sides of outer sheath 380. Lobes 384 are configured to engage prosthesis 182' by friction or by extending through openings in the sidewall of prosthesis 182' so as to facilitate moving prosthesis 182' distally relative to balloon 190 and sheath 184. In this way, prostheses 182 can be advanced through sheath 184 using pusher tube 186 (not shown) until the distal-most prosthesis 182' is positioned in engagement with second valve structure 382 as shown in FIG. 43A. Outer sheath 380 is then pushed distally relative to sheath 184 without moving pusher tube 186 so that the distal-most prosthesis 182' is advanced over balloon 190 outside of sheath 184 as shown in FIG. 43B. Outer sheath 380 is then retracted, wherein lobes 384 slide proximally over prosthesis 182', leaving it in place on balloon 190. If additional prostheses 182 are to be deployed, pusher tube 186 is pushed to advance prostheses 182 in sheath 184 until the most distal prosthesis is in engagement with lobes 384, and the process is repeated.

In an alternative method of using the embodiment of FIGS. 43A-43B, balloon 190 can first be retracted into sheath 184 so that distal-most prosthesis 182' is positioned near the distal end of balloon 190. Pusher tube 186 and balloon 190 are then advanced distally relative to sheath 184 and outer sheath 380, so as to advance the desired number of prosthesis 182' out of sheath 184. At this point, it will often be desirable to create separation between the prostheses 182 to be deployed, and those to remain within sheath 184. For this purpose, outer sheath 380 and balloon 190 can be advanced distally relative to sheath 184 (without pushing pusher tube 186), thereby pushing distally those prostheses 182 to be deployed, separating them from the prostheses 182 to remain within sheath 184. First valve structure 376 retains the prostheses 182 within the sheath as balloon 190 is advanced.

Figure 44:
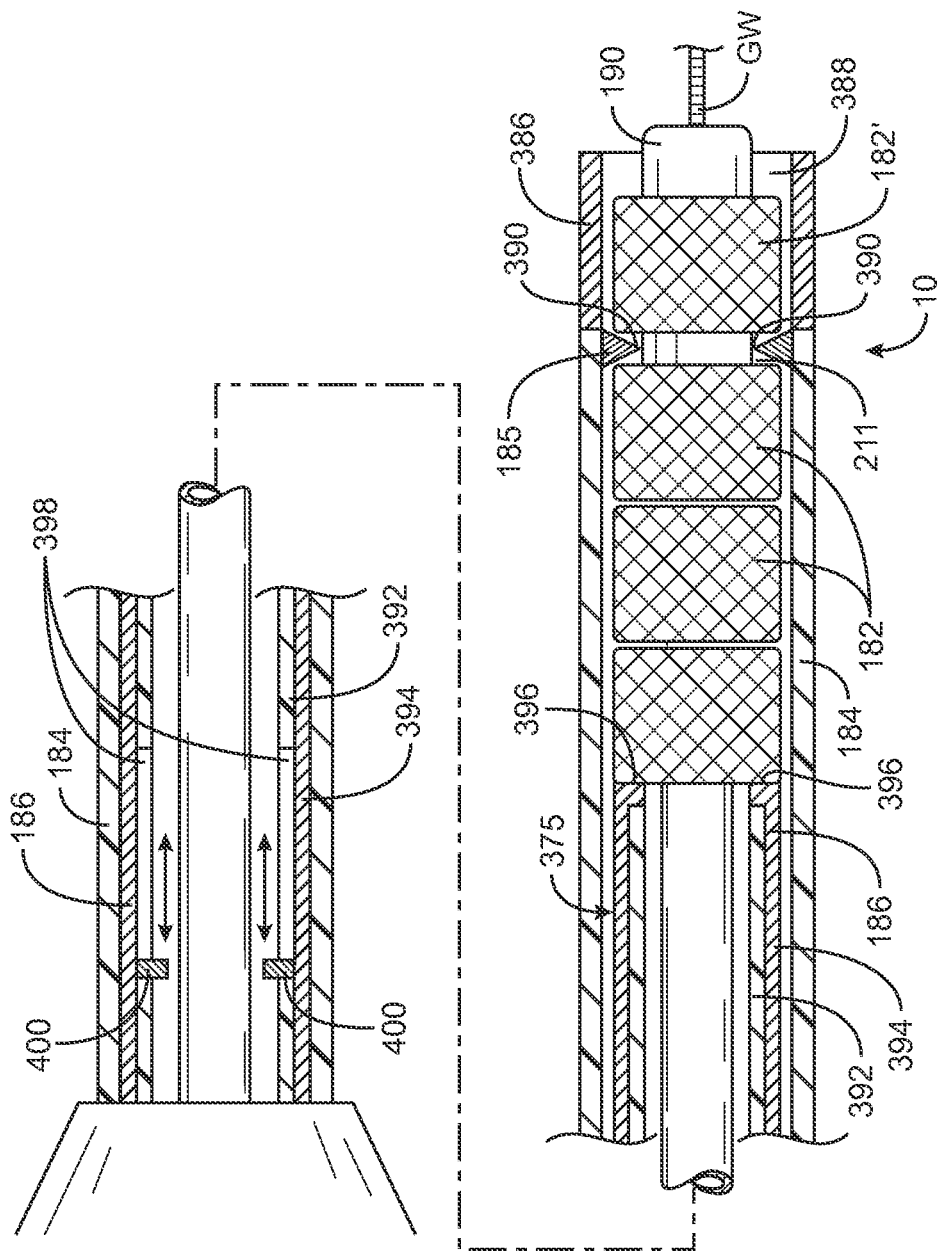
FIG. 44 is a side cross-section of a further embodiment of valve and shuttle members in a delivery catheter according to the invention.

FIG. 44 illustrates a further embodiment of a delivery catheter 10 and shuttle member 375 according to the invention. In this embodiment, a garage member 386 is mounted to the distal end of sheath 184. Garage member 386 has an interior chamber 388 in communication with passageway 211 in sheath 184, and preferably has a length equal to or slightly larger than one of prostheses 182. Valve member 185 is disposed at or near the distal end of sheath 184 and may be similar to any of the embodiments described above. For example, a pair of lobes 390 similar to those described above in connection with FIGS. 15A-15B may be used. In this embodiment, shuttle member 375 comprises a telescoping pusher tube 186 slidably disposed within sheath 184. Pusher tube 186 includes an inner tube 392 and an outer tube 394 slidably disposed over inner tube 392. Outer tube 392 has a widened rim 396 at its distal end configured to engage prostheses 182 to advance them distally through sheath 184. Inner tube 392 has one or more axial slots 398 that have a length at least equal to the length of one of prostheses 182 (or equal to the length of garage member 396). Pins 400 are fixed to outer tube 394 and extend inwardly through slots 398 so as to be axially slidable therein.

In use, balloon 190 is positioned so that its distal end is within garage member 386. Inner tube 392 and outer tube 394 are both pushed distally relative to sheath 184 to advance prostheses 182 until the distal-most prosthesis 182' engages valve member 185 at the distal end of sheath 184. Outer tube 394 is then pushed distally relative to inner tube 392 and sheath 184, pushing the distal-most prosthesis 182' over balloon 190 into garage member 386. The engagement of pins 400 with the distal ends of slots 398 ensures that only one prosthesis 182' is advanced past valve member 185. Balloon 190 along with prosthesis 182' can then be moved distally out of chamber 388. If additional prostheses are to be deployed with prosthesis 182', both parts of pusher tube 186 can be used to push prostheses 182 up to valve member 185, and the process then repeated to advance an additional prosthesis 182 into garage member 386 and onto balloon 190 behind prosthesis 182'.

Figure 45D:
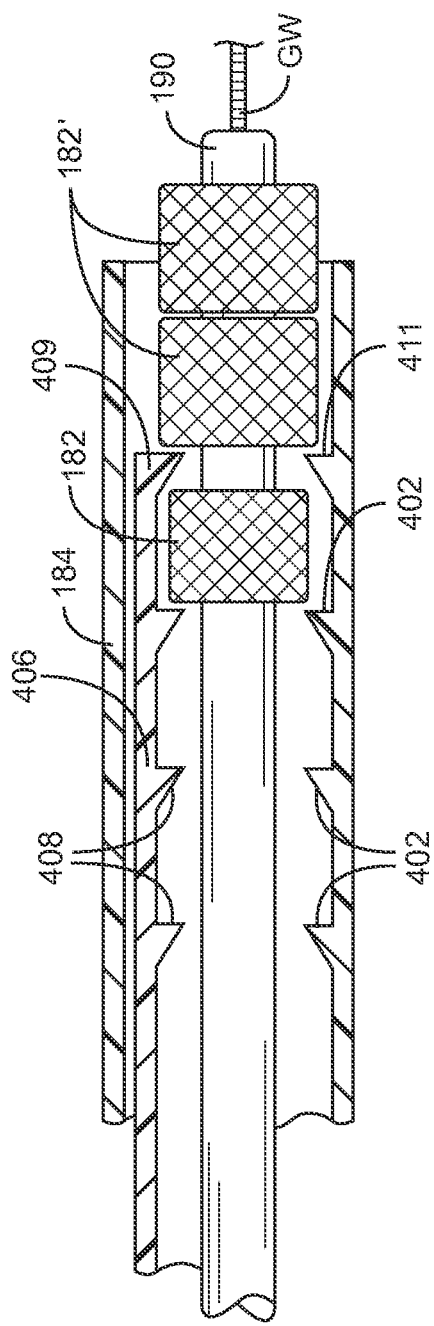
Figure 45E:
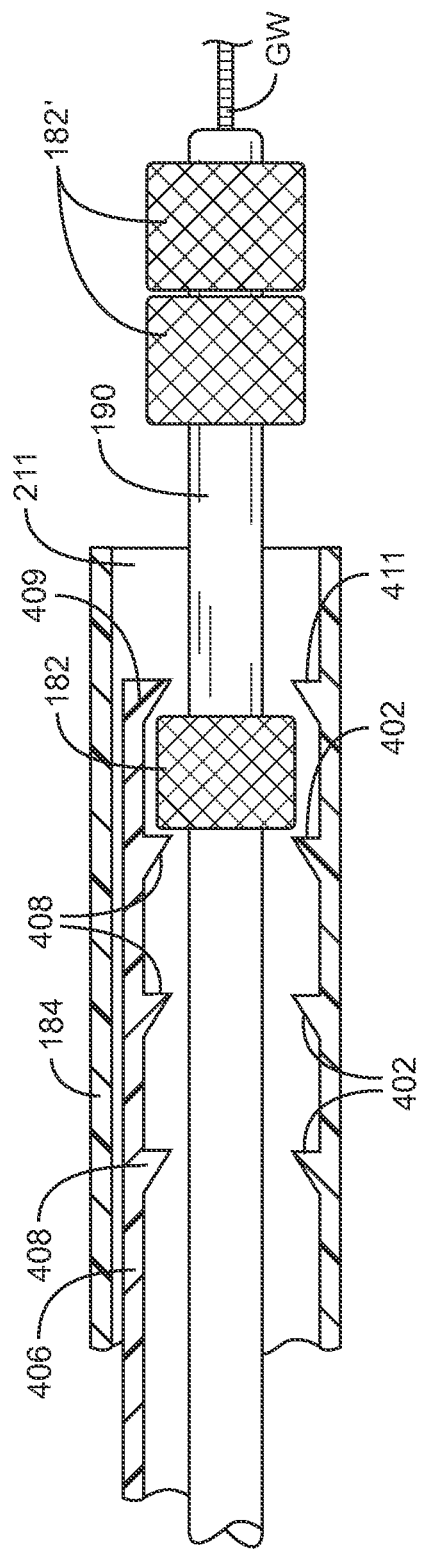

In a further embodiment of catheter 10, shown in FIGS. 45A-45E, a plurality of fixed engagement elements 402 are disposed along the inner wall of sheath 184, preferably spaced apart a distance of about the length of one prosthesis. Fixed engagement elements 402 comprise, in an exemplary embodiment, lobes 404 extending radially inwardly so as to engage prostheses 182 and inhibit their distal movement through passageway 211. Shuttle member 375 comprises a semitube 406 slidably positioned within sheath 184 and having a plurality of engagement structures 408 on its inner wall that are configured to engage prostheses 182 opposite fixed engagement elements 402. Engagement structures 408 may be any of a variety of structures, but in an exemplary embodiment comprise lobes 410 similar to fixed engagement elements 402. In use, semitube 406 is retracted until the distal engagement structure 409 is proximal to the number of prostheses 182 to be deployed, two in the example of FIG. 45C. As semitube 406 is retracted, fixed engagement elements 402 prevent prostheses 182 from being pulled proximally through sheath 184. Semitube 406 is then pushed distally, wherein engagement structures 408 advance prostheses 182 distally through sheath 184. The prostheses 182' to be deployed are advanced distally of the most distal fixed engagement element 411 and up to the distal end of balloon 190, as shown in FIG. 45D, the remaining prostheses 182 remaining proximal to the distal fixed engagement element 411. Balloon 190, carrying prostheses 182', can then be advanced the desired distance distally beyond sheath 184 as shown in FIG. 45E, with fixed engagement elements 402 and engagement structures 408 retaining the remainder of prostheses 182 within sheath 184.

The preferred embodiments of the invention are described above in detail for the purpose of setting forth a complete disclosure and for the sake of explanation and clarity. Those skilled in the art will envision other modifications within the scope and sprit of the present disclosure. For example, while the invention has been described as being useful for the deployment of balloon-expandable prostheses, it should be understood that the principles of the invention are equally applicable to other types of prostheses including self-expanding stents made of Nitinol or other resilient or shape memory materials. Further, the invention will find use not only for deployment of prostheses in the coronary arteries, but in other anatomical locations as well, including the carotid, femoral, and iliac arteries, and other arterial and venous locations. Therefore, the above description should not be taken to limit the scope of the invention, which is defined by the appended claims.

What is claimed is:

1. A method of delivering a stent to a treatment site, the method comprising:
    providing a catheter comprising:
        a sheath having a proximal end, a distal end, an opening at the distal end, and a passage in communication with the opening, the stent being movably disposed in the passage;
        an elongate inner shaft disposed within the sheath, the stent being positionable over the elongate inner shaft, wherein the stent comprises a plurality of axially coupled stent segments; and
        a valve member near the distal end of the sheath adapted for selectively retaining a first stent segment within the passage while allowing a second stent segment to be deployed outside the passage;
    positioning the distal end of the sheath at the treatment site;
    decoupling the second stent segment and the first stent segment; and
    proximally retracting the sheath relative to a distal end of the elongate inner shaft to move the valve member and thereby cause the second stent segment to pass through the opening of the sheath while retaining the first stent segment within the sheath;
    wherein the second stent segment and first stent segment are axially coupled via a coupling member; and
    wherein decoupling the second stent segment and the first stent segment comprises breaking the coupling member.

2. The method of claim 1, wherein the second stent segment is decoupled from the first stent segment by the valve member as the sheath is proximally retracted.

3. The method of claim 1, wherein decoupling the second stent segment and the first stent segment comprises radially expanding the second stent segment while retaining the first stent segment in an unexpanded configuration.

4. The method of claim 1, wherein either or both the first stent segment or the second stent segment comprises a plurality of stent segments.

5. The method of claim 4, wherein the plurality of stent segments of either or both the first stent segment or the second stent segment remain axially coupled after the second stent segment is decoupled from the first stent segment.

6. The method of claim 1, wherein the elongate inner shaft comprises an expandable member near the distal end of the sheath.

7. A method of delivering a stent to a treatment site, the method comprising:
providing a catheter comprising:
a sheath having a proximal end, a distal end, an opening at the distal end, and a passage in communication with the opening, the stent being movably disposed in the passage;
an elongate inner shaft disposed within the sheath, the stent being positionable over a distal end of the elongate inner shaft, wherein the stent comprises a plurality of axially arranged stent segments; and
a valve member near the distal end of the sheath adapted for selectively retaining a first stent segment within the passage while allowing a second stent segment to be deployed outside the passage, wherein the second stent segment and the first stent segment are axially coupled via a coupling member;
positioning the distal end of the sheath and the distal end of the elongate inner shaft at the treatment site; and
proximally retracting the sheath relative to the distal end of the elongate inner shaft to move the valve member and decouple the second stent segment and the first stent segment by breaking the coupling member and to cause the second stent segment to be proximally moved relative to the first stent segment and cause the second stent segment to pass through the opening of the sheath while retaining the first stent segment within the sheath.

8. The method of claim 7, wherein the second stent segment and the first stent segment are decoupled by the valve member as the sheath is proximally retracted.

9. The method of claim 8, wherein breaking the coupling member comprises radially expanding the second stent segment while retaining the first stent segment in an unexpanded configuration.

10. The method of claim 7, wherein either or both the first stent segment or the second stent segment comprises a plurality of stent segments.

11. The method of claim 7, wherein the elongate inner shaft comprises an expandable member positioned near the distal end of the sheath.

12. A method of delivering one or more prostheses to a treatment site, the method comprising:
providing a catheter comprising:
an elongate flexible catheter shaft;
a sheath at least partially disposed over the elongate flexible catheter shaft, the sheath having a proximal end, a distal end, an opening at the distal end, and an interior passage in communication with the opening, the one or more prostheses being movably disposed in the passage; and
a valve member near the distal end of the sheath adapted for selectively retaining at least one prosthesis within the passage;
positioning the distal end of the sheath at the treatment site; and
proximally retracting the sheath to move the valve member and thereby retain the at least one prosthesis within the passage while allowing at least one other prosthesis to pass through the opening of the sheath;
wherein the at least one prosthesis and the at least one other prosthesis are initially axially coupled, and
wherein the at least one prosthesis and the at least one other prosthesis are decoupled by breaking a coupling member that couples the at least one prosthesis and the at least one other prosthesis.

13. The method of claim 12, wherein either or both the at least one prosthesis or the at least one other prosthesis comprises a plurality of stent segments.

14. The method of claim 12, wherein the elongate flexible catheter shaft comprises an expandable member positioned near the distal end of the sheath.

15. The method of claim 12, wherein the valve member is actuatable from the proximal end of the sheath between a first configuration which inhibits movement of the at least one other prosthesis from the passage, and a second configuration which allows movement of the at least one other prosthesis from the passage and through the opening.

\* \* \* \* \*